(12) United States Patent
Seo et al.

(10) Patent No.: US 10,388,900 B2
(45) Date of Patent: Aug. 20, 2019

(54) LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Tsunenori Suzuki, Kanagawa (JP); Yusuke Takita, Kanagawa (JP); Naoaki Hashimoto, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 5 days.

(21) Appl. No.: 15/658,622

(22) Filed: Jul. 25, 2017

(65) Prior Publication Data

US 2018/0033993 A1 Feb. 1, 2018

(30) Foreign Application Priority Data

Jul. 28, 2016 (JP) .................. 2016-148511

(51) Int. Cl.
*H01L 51/00* (2006.01)
*H01L 51/50* (2006.01)
*H01L 51/56* (2006.01)

(52) U.S. Cl.
CPC ........ *H01L 51/5016* (2013.01); *H01L 51/006* (2013.01); *H01L 51/0008* (2013.01); *H01L 51/0052* (2013.01); *H01L 51/0058* (2013.01); *H01L 51/0059* (2013.01); *H01L 51/0072* (2013.01); *H01L 51/0074* (2013.01);
(Continued)

(58) Field of Classification Search
CPC ............. H01L 51/0072; H01L 51/5016; H01L 51/5056; H01L 2251/552
See application file for complete search history.

(56) References Cited

U.S. PATENT DOCUMENTS 6,589,673 B1 7/2003 Kido et al.
8,203,262 B2 6/2012 Seo et al.
(Continued)

FOREIGN PATENT DOCUMENTS

| JP | 2009-177157 A | 8/2009 |
|---|---|---|
| JP | 2011-009498 A | 1/2011 |
| JP | 2014-167946 A | 9/2014 |
| WO | WO 2011/065136 A1 | 6/2011 |

*Primary Examiner* — Zandra V Smith
*Assistant Examiner* — John M Parker
(74) *Attorney, Agent, or Firm* — Husch Blackwell LLP

(57) ABSTRACT

A novel light-emitting element is provided. A light-emitting element with a long lifetime is provided. A light-emitting element with high emission efficiency is provided. In the light-emitting element, an EL layer includes a hole-injection layer, a first hole-transport layer, a second hole-transport layer, a third hole-transport layer, a light-emitting layer, a first electron-transport layer, and a second electron-transport layer in this order; the hole-injection layer includes an organic acceptor; the LUMO level of the host material is higher than that of the first electron-transport layer; the LUMO level of the second electron-transport layer is higher than that of the first electron-transport layer; the host material is a substance including a condensed aromatic ring skeleton; and the first and second electron-transport layers each include a substance having a heteroaromatic ring skeleton.

22 Claims, 34 Drawing Sheets

(52) U.S. Cl.
CPC .......... *H01L 51/5012* (2013.01); *H01L 51/56* (2013.01); *H01L 51/508* (2013.01); *H01L 51/5056* (2013.01); *H01L 51/5064* (2013.01); *H01L 51/5072* (2013.01); *H01L 51/5088* (2013.01); *H01L 2251/552* (2013.01)

(56) References Cited

U.S. PATENT DOCUMENTS

| | | |
|---|---|---|
| 8,841,655 B2 | 9/2014 | Okamoto |
| 9,343,681 B2 | 5/2016 | Suzuki et al. |
| 2001/0046611 A1 | 11/2001 | Kido et al. |
| 2002/0050786 A1 | 5/2002 | Yamazaki et al. |
| 2004/0245542 A1 | 12/2004 | Kim |
| 2006/0008740 A1 | 1/2006 | Kido et al. |
| 2008/0006821 A1 | 1/2008 | Suzuki et al. |
| 2011/0127510 A1* | 6/2011 | Seo .................... H01L 51/0054 257/40 |
| 2011/0240967 A1* | 10/2011 | Lee .................... H01L 51/5004 257/40 |
| 2014/0084273 A1 | 3/2014 | Nakayama et al. |
| 2014/0339524 A1 | 11/2014 | Shitagaki et al. |
| 2014/0340888 A1* | 11/2014 | Ishisone ............. H01L 51/5016 362/231 |
| 2015/0041795 A1 | 2/2015 | Suzuki et al. |
| 2015/0188057 A1 | 7/2015 | Itoi et al. |
| 2016/0336519 A1 | 11/2016 | Sea et al. |
| 2017/0062734 A1* | 3/2017 | Suzuki ............... H01L 51/0072 |
| 2017/0222156 A1* | 8/2017 | Kawakami ........... C07D 307/77 |
| 2017/0309852 A1 | 10/2017 | Seo et al. |

\* cited by examiner

LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, an imaging device, a method for driving any of them, and a method for manufacturing any of them.

2. Description of the Related Art

Light-emitting elements (organic EL elements) including organic compounds and utilizing electroluminescence (EL) have been put to more practical use. In the basic structure of such a light-emitting element, an organic compound layer containing a light-emitting material (an EL layer) is provided between a pair of electrodes. Carriers are injected by application of voltage to the element, and light emission can be obtained from the light-emitting material by using the recombination energy of the carriers.

The light-emitting elements are self-luminous elements and thus have advantages over liquid crystal displays, such as high visibility and no need for backlight when used in pixels of a display, and are suitable as flat panel display elements. In addition, it is also a great advantage that a display including such light-emitting elements can be manufactured as a thin and lightweight display. Furthermore, an extremely high response speed is also a feature thereof.

In such light-emitting elements, light-emitting layers can be successively formed two-dimensionally, so that planar light emission can be obtained. This feature is difficult to realize with point light sources typified by incandescent lamps and LEDs or linear light sources typified by fluorescent lamps. Thus, light-emitting elements also have great potential as planar light sources applied to lighting devices and the like.

Displays or lighting devices including light-emitting elements can be suitably used for a variety of electronic devices as described above, and research and development of light-emitting elements have progressed for higher efficiency or longer lifetime.

An organic acceptor is a material for a hole-injection layer that is used to facilitate the injection of carriers, particularly holes, into an EL layer. The organic acceptor can be easily deposited by evaporation and thus is suitable for mass production and has become widely used. However, the injection of holes into an EL layer is difficult when the LUMO level of the organic acceptor is distanced from the HOMO level of an organic compound included in a hole-transport layer. In contrast, when a substance with a shallow HOMO level is used as the organic compound included in the hole-transport layer so that the HOMO level of the organic compound included in the hole-transport layer is closer to the LUMO level of the organic acceptor, the difference between the HOMO level of the light-emitting layer and the HOMO level of the organic compound included in the hole-transport layer is large, causing difficulty in hole injection from the hole-transport layer into a host material in the light-emitting layer even when holes can be injected into the EL layer.

In addition, the organic acceptor has a low hole-injection capability, which sometimes decreases the lifetime or causes a roll-off at a high-luminance side.

In a structure disclosed in Patent Document 1, a hole-transport material whose HOMO level is between the HOMO level of a first hole-injection layer and the HOMO level of a host material is provided between a light-emitting layer and a first hole-transport layer in contact with the hole-injection layer.

Patent Document 2 discloses a light-emitting element that achieves a long lifetime by including an electron-transport layer to which a substance having an electron-trapping property is added.

Although the characteristics of light-emitting elements have been improved considerably as described above, advanced requirements for various characteristics including efficiency and durability are not yet satisfied.

REFERENCE

Patent Document

[Patent Document 1] PCT International Publication No. WO2011/065136
[Patent Document 2] Japanese Published Patent Application No. 2009-177157

SUMMARY OF THE INVENTION

In view of the above, an object of one embodiment of the present invention is to provide a novel light-emitting element. Another object of one embodiment of the present invention is to provide a light-emitting element with a long lifetime. Another object of one embodiment of the present invention is to provide a light-emitting element with high emission efficiency.

Another object of one embodiment of the present invention is to provide a highly reliable light-emitting device, a highly reliable electronic device, and a highly reliable display device. Another object of one embodiment of the present invention is to provide a light-emitting device, an electronic device, and a display device each with low power consumption.

It is only necessary that at least one of the above-described objects be achieved in the present invention.

One embodiment of the present invention is a light-emitting element that includes a first electrode, a second electrode, and an EL layer. The EL layer is positioned between the first electrode and the second electrode; the EL layer includes a hole-injection layer, a first hole-transport layer, a second hole-transport layer, a third hole-transport layer, a light-emitting layer, a first electron-transport layer, and a second electron-transport layer; the hole-injection layer, the first hole-transport layer, the second hole-transport layer, and the third hole-transport layer are positioned between the first electrode and the light-emitting layer; the first electrode is in contact with the hole-injection layer; the hole-injection layer is in contact with the first hole-transport layer; the third hole-transport layer is in contact with the light-emitting layer; the second hole-transport layer is positioned between the first hole-transport layer and the third hole-transport layer; the first electron-transport layer and the second electron-transport layer are positioned between the light-emitting layer and the second electrode; the light-emitting layer is in contact with the first electron-transport layer; the first electron-transport layer is in contact with the second electron-transport layer; the hole-injection layer contains an organic acceptor; the first hole-transport layer contains a first hole-transport material; the second hole-transport layer contains a second hole-transport material; the third hole-transport layer contains a third hole-transport material; the light-emitting layer contains a host material and a light-emitting material; the first electron-transport layer contains a first electron-transport material; the second electron-transport layer contains a second electron-transport material; the HOMO level of the second hole-transport material is deeper than the HOMO level of the first hole-transport material; the HOMO level of the host material is deeper than the HOMO level of the second hole-transport material; the HOMO level of the third hole-transport material is deeper than or equal to the HOMO level of the host material; the difference between the HOMO level of the second hole-transport material and the HOMO level of the third hole-transport material is less than or equal to 0.3 eV; the LUMO level of the host material is higher than the LUMO level of the first electron-transport material; the LUMO level of the second electron-transport material is higher than the LUMO level of the first electron-transport material; the host material is a substance including a condensed aromatic ring skeleton including 3 to 6 rings; the first electron-transport material is a substance including a first heteroaromatic ring skeleton; the second electron-transport material is a substance including a second heteroaromatic ring skeleton; and the substance including the first heteroaromatic ring skeleton and the substance including the second heteroaromatic ring skeleton are different substances.

Another embodiment of the present invention is a light-emitting element having the above structure, in which the light-emitting material is a fluorescent material.

Another embodiment of the present invention is a light-emitting element having the above structure, in which the light-emitting material emits blue light.

Another embodiment of the present invention is a light-emitting element having the above structure, in which the light-emitting material is a condensed aromatic diamine compound.

Another embodiment of the present invention is a light-emitting element having the above structure, in which the light-emitting material is a pyrenediamine compound.

Another embodiment of the present invention is a light-emitting element having the above structure, in which the organic acceptor is 2,3,6,7,10,11-hexacyano-1,4,5,8,9,12-hexaazatriphenylene.

Another embodiment of the present invention is a light-emitting element having the above structure, in which the HOMO level of the first hole-transport material is greater than or equal to −5.4 eV.

Another embodiment of the present invention is a light-emitting element having the above structure, in which the difference between the HOMO level of the first hole-transport material and the HOMO level of the second hole-transport material is less than or equal to 0.3 eV.

Another embodiment of the present invention is a light-emitting element having the above structure, in which the difference between the HOMO level of the second hole-transport material and the HOMO level of the third hole-transport material is less than or equal to 0.2 eV.

Another embodiment of the present invention is a light-emitting element having the above structure, in which the difference between the HOMO level of the first hole-transport material and the HOMO level of the second hole-transport material is less than or equal to 0.2 eV.

Another embodiment of the present invention is a light-emitting element having the above structure, in which the HOMO level of the light-emitting material is higher than the HOMO level of the host material.

Another embodiment of the present invention is a light-emitting element having the above structure, in which the first hole-transport material is a triarylamine and has a fluorenylamine skeleton.

Another embodiment of the present invention is a light-emitting element having the above structure, in which the second hole-transport material is a triarylamine and has a triphenylamine skeleton.

Another embodiment of the present invention is a light-emitting element having the above structure, in which the third hole-transport material is a substance that does not include amine.

Another embodiment of the present invention is a light-emitting element having the above structure, in which the third hole-transport material includes a carbazole skeleton.

Another embodiment of the present invention is a light-emitting element having the above structure, in which the carbazole skeleton is a phenylcarbazole skeleton.

Another embodiment of the present invention is a light-emitting element having the above structure, in which the third hole-transport material includes a triphenylene skeleton.

Another embodiment of the present invention is a light-emitting element having the above structure, in which the third hole-transport material includes a naphthalene skeleton.

Another embodiment of the present invention is a light-emitting element having the above structure, in which the host material includes an anthracene skeleton.

Another embodiment of the present invention is a light-emitting element having the above structure, in which the host material includes a diphenylanthracene skeleton.

Another embodiment of the present invention is a light-emitting element having the above structure, in which the host material includes a carbazole skeleton.

Another embodiment of the present invention is a light-emitting element having the above structure, in which the carbazole skeleton includes a benzocarbazole skeleton.

Another embodiment of the present invention is a light-emitting element having the above structure, in which the carbazole skeleton is a dibenzocarbazole skeleton.

Another embodiment of the present invention is a light-emitting element having the above structure, in which the substance including the first heteroaromatic ring skeleton and the substance including the second heteroaromatic ring skeleton are each a substance including a six-membered nitrogen-containing heteroaromatic ring skeleton.

Another embodiment of the present invention is a light-emitting element having the above structure, in which the substance including the first heteroaromatic ring skeleton is a substance including a condensed heteroaromatic ring skeleton.

Another embodiment of the present invention is a light-emitting element having the above structure, in which the substance including the first heteroaromatic ring skeleton is a substance including a condensed heteroaromatic ring skeleton including a diazine skeleton or a triazine skeleton.

Another embodiment of the present invention is a light-emitting element having the above structure, in which the substance including the first heteroaromatic ring skeleton is a substance including a pyrazine skeleton or a pyrimidine skeleton.

Another embodiment of the present invention is a light-emitting element having the above structure, in which the substance including the first heteroaromatic ring skeleton is a substance including a dibenzoquinoxaline skeleton.

Another embodiment of the present invention is a light-emitting element having the above structure, in which the second electron-transport layer is in contact with the second electrode.

Another embodiment of the present invention is a light-emitting device including the light-emitting element with any of the above structures, and a transistor or a substrate.

Another embodiment of the present invention is an electronic device including the light-emitting element with any of the above structures, and a sensor, an operation button, a speaker, or a microphone.

Another embodiment of the present invention is a lighting device including the light-emitting element with any of the above structures, and a housing.

Note that the light-emitting device in this specification includes an image display device using a light-emitting element. The light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may also be included in lighting equipment and the like.

According to one embodiment of the present invention, a novel light-emitting element can be provided. A light-emitting element with a long lifetime can also be provided. A light-emitting element with high emission efficiency can also be provided.

According to another embodiment of the present invention, a highly reliable light-emitting device, electronic device, and display device can be provided. A low-power-consumption light-emitting device, electronic device, and display device can also be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 9A, 9B1, 9B2, 9C, and 9D each illustrate an electronic device.

DETAILED DESCRIPTION OF THE INVENTION

Embodiment of the present invention will be described below in detail with reference to the drawings. Note that the present invention is not limited to the following description, and it will be readily appreciated by those skilled in the art that the modes and details can be changed in various ways without departing from the spirit and the scope of the present invention. Accordingly, the present invention should not be interpreted as being limited to the content of the embodiment below.

Figure 1A:
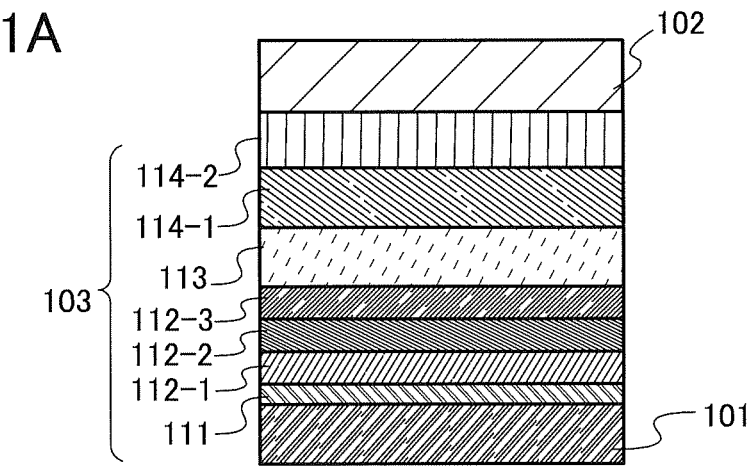
FIGS. 1A to 1C are conceptual diagrams of light-emitting elements.

FIG. 1A illustrates a light-emitting element of one embodiment of the present invention. The light-emitting element of one embodiment of the present invention includes a first electrode 101, a second electrode 102, and an EL layer 103. The EL layer 103 includes, from the first electrode 101 side, a hole-injection layer 111, a first hole-transport layer 112-1, a second hole-transport layer 112-2, a third hole-transport layer 112-3, a light-emitting layer 113, a first electron-transport layer 114-1, and a second electron-transport layer 114-2. Note that the light-emitting element may include other functional layers.

In the light-emitting element of one embodiment of the present invention, the light-emitting layer 113 contains a host material and a light-emitting material. The hole-injection layer 111 contains an organic acceptor. The first hole-transport layer 112-1 contains a first hole-transport material. The second hole-transport layer 112-2 contains a second hole-transport material. The third hole-transport layer 112-3 contains a third hole-transport material. The first electron-transport layer 114-1 contains a first electron-transport material. The second electron-transport layer 114-2 contains a second electron-transport material. Note that the first hole-transport material, the second hole-transport material, the third hole-transport material, the first electron-transport material, and the second electron-transport material are different substances.

The HOMO level of the host material is deeper than the HOMO level of the second hole-transport material, and the HOMO level of the second hole-transport material is deeper than the HOMO level of the first hole-transport material. The HOMO level of the third hole-transport material is deeper than or equal to the HOMO level of the host material. Note that the difference between the HOMO level of the second hole-transport material and the HOMO level of the third hole-transport material is less than or equal to 0.3 eV (one significant figure).

The host material is a substance including a condensed aromatic ring skeleton including 3 to 6 rings. The first electron-transport material and the second electron-transport material are each a substance including a heteroaromatic ring skeleton. In the light-emitting element of one embodiment of the present invention, the LUMO level of the host material and the LUMO level of the second electron-transport material are higher (shallower) than the LUMO level of the first electron-transport material. Note that the difference between the LUMO level of the host material and the LUMO level of the first electron-transport material is preferably less than or equal to 0.3 eV (one significant figure), in which case an increase in driving voltage can be reduced.

In order that the carrier injection barriers between layers are reduced to decrease the driving voltage and improve the lifetime, a light-emitting element is typically designed so that the HOMO levels of layers on the hole-transport layer side become lower (deeper) from the layer closer to the first electrode 101, which is the anode, to the layer closer to the light-emitting layer 113 and the LUMO levels of layers on the electron-transport layer side become higher (shallower) from the layer closer to the second electrode 102, which is the cathode, to the layer closer to the light-emitting layer 113.

In contrast, the light-emitting element of one embodiment of the present invention satisfies the aforementioned relationships between the HOMO level of the host material and the HOMO level of the material contained in the hole-transport layer and between the LUMO level of the host material and the LUMO level of the material contained in the electron-transport layer; in addition, substances having specific skeletons are used for the host material and the material contained in the electron-transport layer. As a result, it is possible to provide a light-emitting element that has a longer lifetime, higher efficiency, and better emission properties than conventional light-emitting elements.

The host material preferably includes a condensed aromatic ring skeleton including 3 to 6 rings because such a condensed aromatic ring can have electrochemical stability with the energy gap maintained around the visible light region. In particular, an anthracene skeleton is preferred because an energy gap large enough to excite a blue fluorescent material can be obtained and both holes and electrons can be transported. In addition, the LUMO level of an anthracene derivative can be easily set to approximately −2.7 eV, which is suitable for satisfying the aforementioned relationship of the LUMO levels with the electron-transport layer.

The first electron-transport material and the second electron-transport material preferably include different heteroaromatic ring skeletons because in that case, the LUMO level of the first electron-transport material can be made lower (deeper) than the LUMO levels of the host material and the second electron-transport material.

Note that the light-emitting element of one embodiment of the present invention includes the hole-injection layer 111 and uses an organic acceptor material for the hole-injection layer 111; hence, a decrease in efficiency in a high-luminance region, what is called a roll-off, can be reduced to achieve a light-emitting element with higher luminance and efficiency as well as with a longer lifetime than conventional light-emitting elements.

The organic acceptor is an organic compound with a deep LUMO level. When charge separation is caused between the organic acceptor and another organic compound whose HOMO level is close to the LUMO level of the organic acceptor, holes can be generated in the organic compound. That is, in the light-emitting element of this embodiment, holes are generated in the first hole-transport material, which is in contact with the organic acceptor. As the organic acceptor, a compound including an electron-withdrawing group (a halogen group or a cyano group), e.g., 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, and 2,3,6,7,10,11-hexacyano-1,4,5,8,9,12-hexaazatriphenylene (abbreviation: HAT-CN), can be used. HAT-CN is particularly preferable because it has a high acceptor property and exhibits stable film quality.

Although the difference between the LUMO level of the organic acceptor and the HOMO level of the first hole-transport material is not particularly limited because it depends on the strength of the acceptor property of the organic acceptor, holes can be injected when the difference between the levels is less than or equal to approximately 1 eV. Since the LUMO level of HAT-CN is estimated to −4.41 eV by cyclic voltammetry measurement, in the case where HAT-CN is used as the organic acceptor, the HOMO level of the first hole-transport material is preferably greater than or equal to −5.4 eV. Note that if the HOMO level of the first hole-transport material is too high, the hole-injection property for the second hole-transport material deteriorates. In addition, since the work function of an anode such as ITO is approximately −5 eV, the use of a material whose HOMO level is higher than −5 eV as the first hole-transport material brings a disadvantage. Therefore, the HOMO level of the first hole-transport material is preferably less than or equal to −5.0 eV.

Holes generated in the first hole-transport material are moved toward the second electrode 102 by an electric field and injected to the second hole-transport layer 112-2. The HOMO level of the second hole-transport material included in the second hole-transport layer 112-2 is positioned between the HOMO level of the first hole-transport material and the HOMO level of the host material, so that the holes can be easily injected from the first hole-transport layer 112-1 to the second hole-transport layer 112-2. Note that to smoothly inject the holes, the difference in HOMO level between the hole-transport material and the second hole-transport material is preferably less than or equal to 0.3 eV; to inject the holes more easily, the difference is further preferably less than or equal to 0.2 eV.

The holes injected to the second hole-transport layer 112-2 are further moved toward the second electrode 102 by an electric field and injected to the third hole-transport layer 112-3. The HOMO level of the third hole-transport material included in the third hole-transport layer 112-3 is deeper than or equal to the HOMO level of the host material, and the difference in HOMO level between the third hole-transport material and the second hole-transport material is less than 0.35 eV (less than or equal to 0.3 eV with one significant figure). Since the difference between the HOMO level of the second hole-transport material and the HOMO level of the third hole-transport material is less than or equal to 0.3 eV, holes are smoothly injected from the second hole-transport layer 112-2 to the third hole-transport layer 112-3. Note that for more smooth hole injection, the difference between the HOMO level of the third hole-transport material and the HOMO level of the second hole-transport material is preferably less than 0.25 eV (less than or equal to 0.2 eV with one significant figure).

Since the HOMO level of the third hole-transport material is deeper than or equal to the HOMO level of the host material, no barrier exists when holes are injected from the third hole-transport layer 112-3 to the light-emitting layer 113; furthermore, holes are likely to be injected directly not only to the light-emitting material but also to the host material. If holes enter the light-emitting material preferentially, movement of holes in the light-emitting layer becomes extremely difficult, and a light-emitting region is localized at the interface between the hole-transport layer and the light-emitting layer, which adversely affects the element lifetime. In contrast, when holes also enter the host material as in one embodiment of the present invention, the holes are transferred mainly in the host in the light-emitting layer while being moderately influenced by hole trapping in the light-emitting material; therefore, the light-emitting region can be expanded moderately, resulting in high efficiency and long lifetime. The moderate expansion of the light-emitting region means that holes are transferred in the light-emitting layer to some extent but do not penetrate the light-emitting layer. Accordingly, it is preferable that the host material have a hole-transport property, specifically, have an anthracene skeleton or a carbazole skeleton. An anthracene skeleton is particularly preferable because it is preferable that the host material have an electron-transport property. In other words, it is further preferable that the host material have both an anthracene skeleton and a carbazole skeleton. The carbazole skeleton is preferably a benzocarbazole skeleton or a dibenzocarbazole skeleton. This is because the HOMO level of any of these structures is higher than the HOMO level of carbazole by approximately 0.1 eV, which facilitates holes to enter the host material (as a result, the moderate expansion of the light-emitting region described above is facilitated). In this manner, including the third hole-transport layer 112-3 is one of the features of the light-emitting element of one embodiment of the present invention.

Here, in the case where the HOMO level of the light-emitting material is shallower than the HOMO level of the host material, when holes are injected to the light-emitting layer from the hole-transport material whose HOMO level is shallower than that of the host material, the holes are injected preferentially to the light-emitting material than to the host material. When holes are injected to the light-emitting material with a shallow HOMO level, the holes are trapped. The trap of holes inhibits holes from flowing, which causes problems such as accumulation of charge, acceleration of deterioration of the light-emitting layer due to localization of a recombination region, and reduction in emission efficiency.

In contrast, in a light-emitting element that includes the third hole-transport layer 112-3 whose HOMO level is deeper than or equal to the HOMO level of the host material as in the light-emitting element of this embodiment, holes are preferentially injected to the host material first, not to the light-emitting material. As a result, the flow of holes is not inhibited, holes are moderately trapped in the light-emitting material, and the recombination region is dispersed, which produces various effects such as improvements in the reliability and emission efficiency.

Next, examples of specific structures and materials of the above-described light-emitting element are described. As described above, the light-emitting element of one embodiment of the present invention includes, between the pair of electrodes (the first electrode 101 and the second electrode 102), the EL layer 103 including a plurality of layers. In the EL layer 103, at least the hole-injection layer 111, the first hole-transport layer 112-1, the second hole-transport layer 112-2, the third hole-transport layer 112-3, the light-emitting layer 113, the first electron-transport layer 114-1, and the second electron-transport layer 114-2 are provided in this order from the first electrode 101 side so that the layers are in contact with each other.

The first electrode 101 is preferably formed using any of metals, alloys, conductive compounds with a high work function (specifically, a work function of 4.0 eV or more), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 wt % to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Figure 1B:
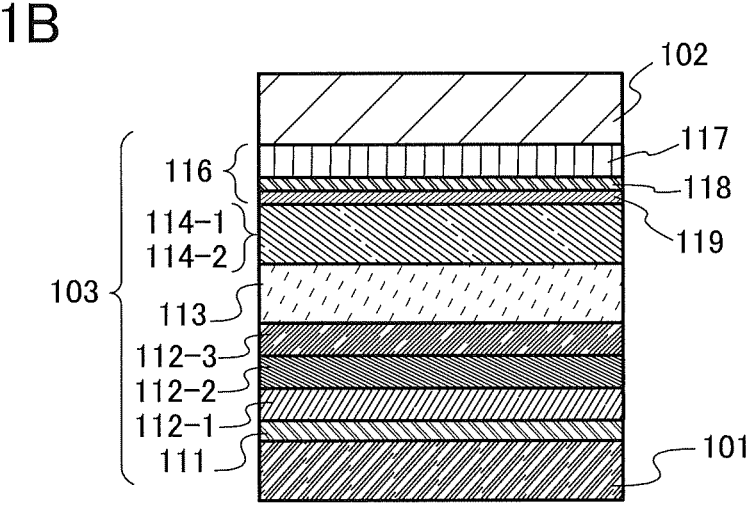

The EL layer 103 described in this embodiment has the following two types of layered structures: the structure illustrated in FIG. 1A, which includes the hole-injection layer 111, the first hole-transport layer 112-1, the second hole-transport layer 112-2, the third hole-transport layer 112-3, the light-emitting layer 113, the first electron-transport layer 114-1, and the second electron-transport layer 114-2; and the structure illustrated in FIG. 1B, which includes a charge-generation layer 116 in addition to the hole-injection layer 111, the first hole-transport layer 112-1, the second hole-transport layer 112-2, the third hole-transport layer 112-3, the light-emitting layer 113, the first electron-transport layer 114-1, and the second electron-transport layer 114-2. Materials for forming each layer are specifically described below.

The hole-injection layer 111 includes an organic acceptor. As the organic acceptor, a compound including an electron-withdrawing group (a halogen group or a cyano group), e.g., 7,7,8,8-tetracyano-2,3,5,6-tetrafluoroquinodimethane (abbreviation: $F_4$-TCNQ), 3,6-difluoro-2,5,7,7,8,8-hexacyano-quinodimethane, chloranil, or 2,3,6,7,10,11-hexacyano-1,4,5,8,9,12-hexaazatriphenylene (abbreviation: HAT-CN), can be used. A compound in which electron-withdrawing groups are bonded to a condensed aromatic ring having a plurality of hetero atoms, like HAT-CN, is preferable as the organic acceptor because it is thermally stable. The organic acceptor can extract an electron from an adjacent hole-transport layer (or hole-transport material) by at least application of an electric field.

The hole-injection layer 111 can improve the hole-injection property, which allows the light-emitting element to be driven at a low voltage. In addition, the organic acceptor is easy to use because it is easily formed by vapor deposition.

The first hole-transport layer 112-1, the second hole-transport layer 112-2, and the third hole-transport layer 112-3 form a hole-transport layer. The first to third hole-transport layers 112-1, 112-2, and 112-3 each include a hole-transport material with a hole-transport property; specifically, the first hole-transport layer 112-1 includes the first hole-transport material, the second hole-transport layer 112-2 includes the second hole-transport material, and the third hole-transport layer 112-3 includes the third hole-transport material. The hole-transport materials preferably have a hole mobility higher than or equal to $1 \times 10^{-6}$ cm$^2$/Vs. In addition, these materials satisfy the following relationships: the HOMO level of the second hole-transport material is deeper than the HOMO level of the first hole-transport material, the HOMO level of the host material included in the light-emitting layer 113 is deeper than the HOMO level of the second hole-transport material, the HOMO level of the third hole-transport material is deeper than or equal to the HOMO level of the host material, and the difference between the HOMO level of the second hole-transport material and the HOMO level of the third hole-transport material is less than or equal to 0.3 eV. Note that the difference between the HOMO level of the second hole-transport material and the HOMO level of the third hole-transport material is preferably less than or equal to 0.2 eV.

As the first hole-transport material, a hole-transport material with a relatively shallow HOMO level is preferable. As such an organic compound, a substance that is triarylamine and has a fluorenylamine skeleton is preferable.

As the third hole-transport material, a hole-transport material with a relatively deep HOMO level is preferably used. Since an organic compound including amine tends to have a shallow HOMO level, a hole-transport material without amine is preferable. Note that as such a hole-transport material, a hole-transport material having a carbazole skeleton is preferable. An organic compound having a carbazole skeleton and a triphenylene skeleton, an organic compound having a carbazole skeleton and a naphthalene skeleton, and the like can be preferably used.

As the second hole-transport material, a hole-transport material whose HOMO level is between the HOMO levels of the first and third hole-transport materials is preferable. Specifically, a hole-transport material that is triarylamine and has a triphenylamine skeleton is preferable. Note that it is preferable that a phenyl group of the triphenylamine skeleton do not form a fused structure.

The light-emitting layer 113 includes the host material and the light-emitting material. The light-emitting material may be any of fluorescent substances, phosphorescent substances, and substances exhibiting thermally activated delayed fluorescence (TADF). Furthermore, the light-emitting layer 113 may be a single layer or include a plurality of layers containing different light-emitting materials. Note that in one embodiment of the present invention, a layer that emits fluorescence, specifically, blue fluorescence, is more suitably used as the light-emitting layer 113.

Examples of the material that can be used as a fluorescent substance in the light-emitting layer 113 are described below. Fluorescent substances other than those given below can also be used.

Examples of the fluorescent substance include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'- biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). In particular, condensed aromatic diamine compounds typified by pyrenediamine compounds such as 1,6FLPAPrn and 1,6mMemFLPAPrn are preferable because of their high hole-trapping properties, high emission efficiency, and high reliability.

Examples of the material that can be used as a phosphorescent substance in the light-emitting layer 113 are as follows.

The examples include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These are compounds that emit blue phosphorescence and have an emission peak at 440 nm to 520 nm.

Other examples include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and rare earth metal complexes such as tris(acetylacetonato)(monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), bis[4,6-di(naphthalen-1-yl)pyrimidinato](dipivaloylmethanato)iridium(III) (abbreviation: [Ir(dlnpm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). These are compounds that emit red phosphorescence and have an emission peak at 600 nm to 700 nm. Furthermore, organometallic iridium complexes having pyrazine skeletons can provide red light emission with favorable chromaticity.

Besides the above phosphorescent compounds, known phosphorescent materials may be selected and used.

Examples of the TADF material include a fullerene, a derivative thereof, an acridine derivative such as proflavine, and eosin. Furthermore, a metal-containing porphyrin, such as a porphyrin containing magnesium (Mg), zinc (Zn), cadmium (Cd), tin (Sn), platinum (Pt), indium (In), or palladium (Pd) can be used. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂(OEP)), which are represented by the following structural formulae.
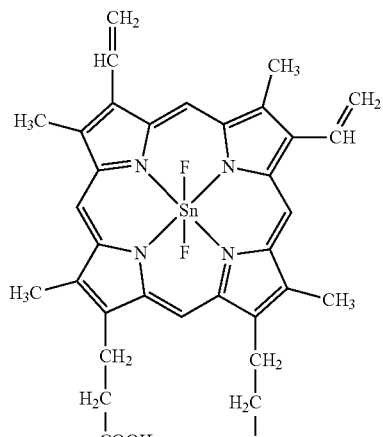
SnF₂(Proto IX)
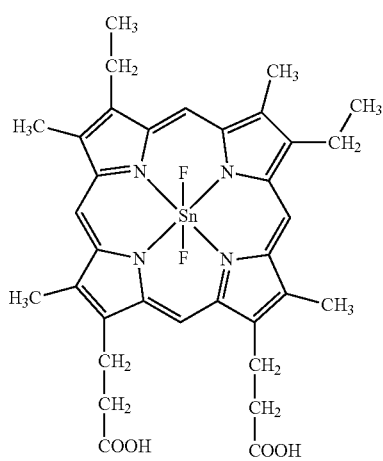
SnF₂(Meso IX)
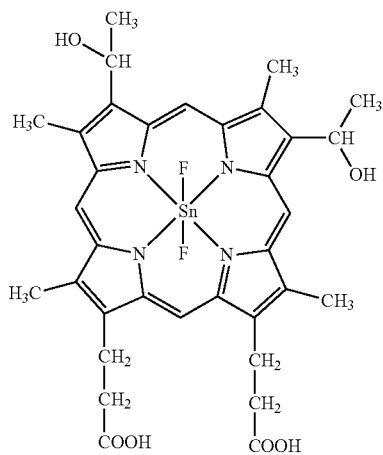
SnF₂(Hemato IX)
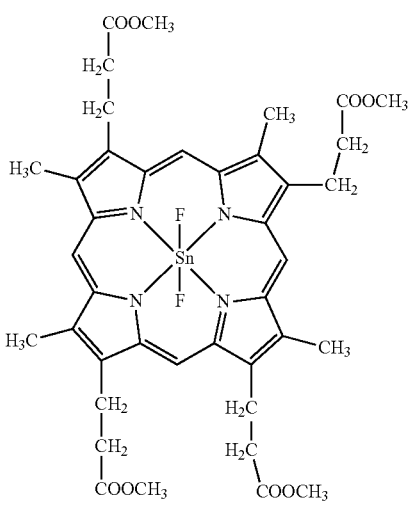
SnF₂(Copro III-4Me)
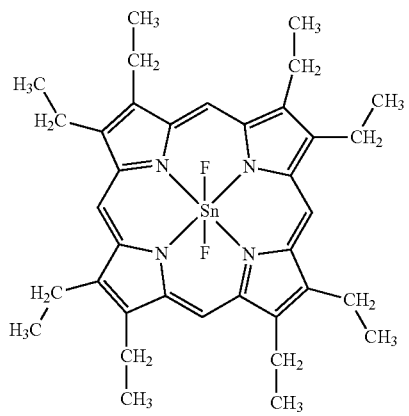
SnF₂(OEP)
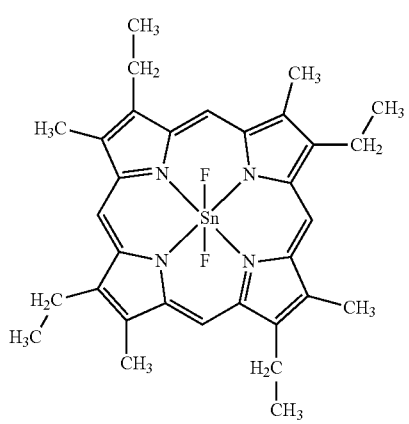
SnF₂(Etio I)

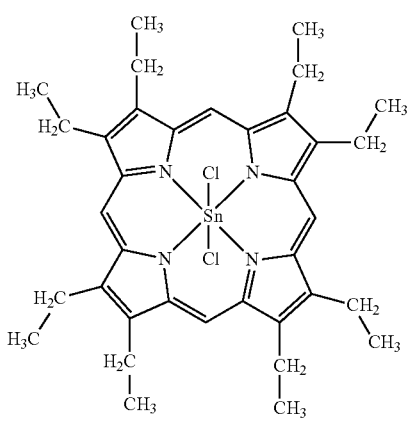

PtCl₂OEP

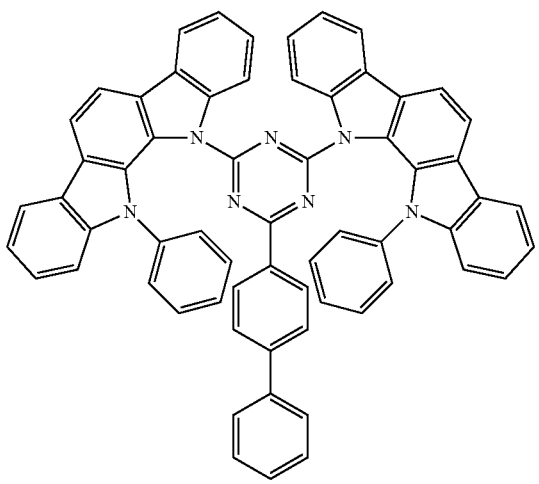

PIC-TRZ

Alternatively, a heterocyclic compound having both a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased, the energy difference between the $S_1$ level and the $T_1$ level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring.

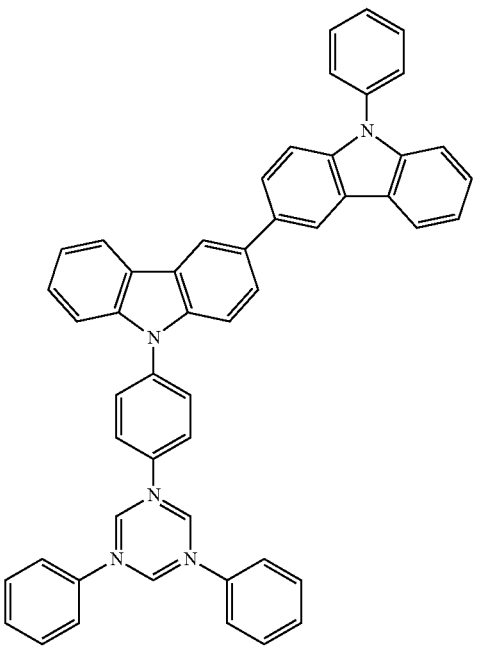

PCCzPTzn

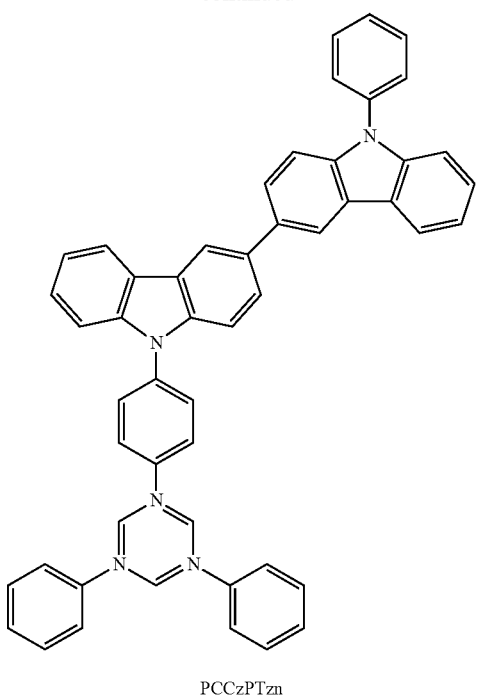

PCCzPTzn

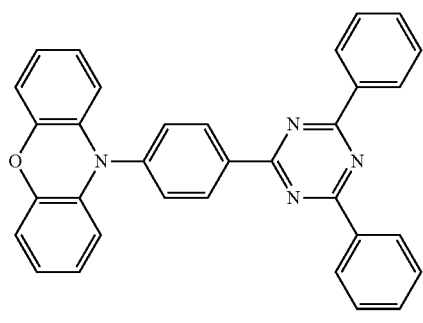

PXZ-TRZ

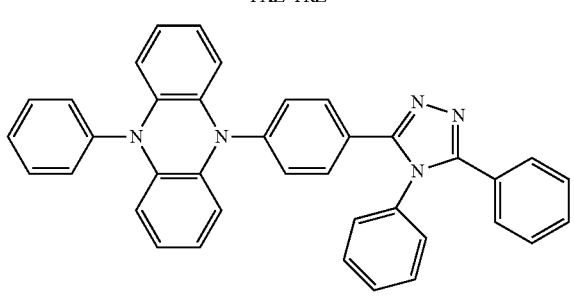

PPZ-3TPT

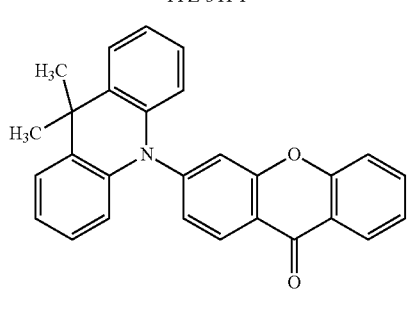

ACRXTN

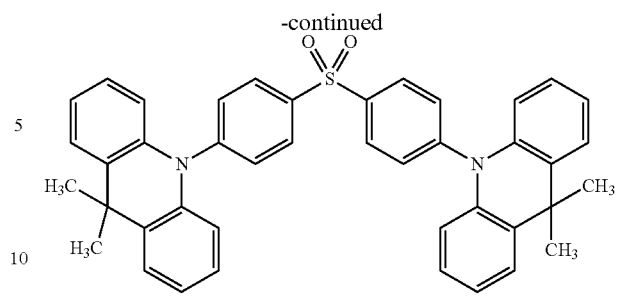

DMAC-DPS

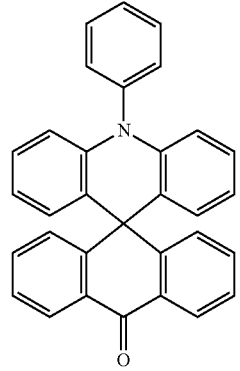

ACRSA

As the host material in the light-emitting layer, various carrier-transport materials such as materials with an electron-transport property and materials with a hole-transport property can be used.

As the host material in the light-emitting layer, various carrier-transport materials such as substances with a hole-transport property and substances with an electron-transport property, which are given below, can be used. Needless to say, a material having a hole-transport property, a material having an electron-transport property, or a bipolar material other than the substances listed below can also be used.

The following are examples of the materials having a hole-transport property: compounds having aromatic amine skeletons, such as 4,4'-bis[N-(1-naphthyl)-N-phenylamino] biphenyl (abbreviation: NPB), N,N'-bis(3-methylphenyl)-N,N'-diphenyl-[1,1'-biphenyl]-4,4'-diamine (abbreviation: TPD), 4,4'-bis[N-(Spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable, have a high hole-transport property, and contribute to a reduction in driving voltage.

The following are examples of materials having an electron-transport property: metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBT-BIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons and the heterocyclic compounds having pyridine skeletons are highly reliable and preferred. In particular, the heterocyclic compounds having diazine (pyrimidine or pyrazine) skeletons have a high electron-transport property and contribute to a decrease in driving voltage.

Note that the host material may be a mixture of some kinds of substances, and in the case where a mixed host material is used, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed by these mixed materials. It is preferable that the combination of these materials be selected so as to form an exciplex that emits light with a wavelength overlapping with that of the lowest energy absorption band of the light-emitting material, in which case energy is transferred smoothly, light emission can be obtained efficiently, and the driving voltage is reduced.

In the light-emitting element of one embodiment of the present invention, the host material is preferably a substance including a condensed aromatic ring skeleton including 3 to 6 rings. The following are examples of the substance including a condensed aromatic ring skeleton including 3 to 6 rings: substances including anthracene skeletons such as CzPA, 7-[4-(10-phenyl-9-anthryl)phenyl]-7H-dibenzo[c,g]carbazole (abbreviation: cgDBCzPA), 9-phenyl-3-[4-(10-phenyl-9-anthryl)phenyl]-9H-carbazole (abbreviation: PCzPA), 4-[3-(9,10-diphenyl-2-anthryl)phenyl]dibenzofuran (abbreviation: 2mDBFPPA-II), t-BuDNA, and 9-(2-naphthyl)-10-[4-(1-naphthyl)phenyl]anthracene (abbreviation: BH-1); substances including tetracene skeletons such as 5,12-diphenyltetracene (abbreviation: DPT), rubrene, and 2,8-di-tert-butyl-5,11-bis(4-tert-butylphenyl)-6,12-diphenyltetracene (abbreviation: TBRb); substances including pyrene skeletons such as 1,3,5-tri(1-pyrenyl)benzene (abbreviation: TPB3), 9,9-bis[4-(1-pyrenyl)phenyl]-9H-fluoren (abbreviation: BPPF), and 2,7-bis(1-pyrenyl)-spiro-9,9'-bifluorene (abbreviation: Spyro-pye); a substance including a perylene skeleton such as 2,5,8,11-tetra(tert-butyl)perylene (abbreviation: TBP); a substance including a fluoranthene skeleton; and a substance including a dibenzochrysene skeleton. Among these substances, substances including an anthracene skeleton are particularly preferred as described above.

Note that each of the first electron-transport material and the second electron-transport material is preferably a substance including a six-membered nitrogen-containing heteroaromatic ring skeleton. A substance including a six-membered nitrogen-containing heteroaromatic ring skeleton has higher reliability as an electron acceptor than a five-membered nitrogen-containing heterocyclic skeleton (e.g., pyrrole, indole, carbazole, imidazole, benzimidazole, triazole, or benzotriazole), so that a highly reliable light-emitting element can be obtained. A substance including a six-membered nitrogen-containing heteroaromatic ring skeleton is particularly suitable for the first electron-transport material because the substance including a six-membered nitrogen-containing heteroaromatic ring skeleton tends to have a deeper LUMO level than a substance including a five-membered nitrogen-containing heterocyclic skeleton.

Therefore, the first electron-transport material preferably includes a triazine skeleton or a diazine skeleton (in particular, a pyrazine skeleton or a pyrimidine skeleton), particularly a condensed heteroaromatic ring skeleton. A favorable example of the substance including a condensed heteroaromatic ring skeleton including a diazine skeleton is a substance including a highly reliable benzoquinazoline skeleton or dibenzoquinoxaline skeleton. In particular, a substance including a dibenzoquinoxaline skeleton, whose LUMO level is likely to be deep, is preferred. With such a structure, the light-emitting element of one embodiment of the present invention can be a long-lifetime light-emitting element with little degradation of luminance with the accumulated driving time.

The second electron-transport material is preferably a substance including a pyridine skeleton or a bipyridine skeleton in the case of being in contact with the cathode. In that case, the first electron-transport material preferably includes a triazine skeleton or a diazine skeleton (in particular, a pyrazine skeleton or a pyrimidine skeleton), because the LUMO level of the substance including a pyridine skeleton or a bipyridine skeleton is higher than the LUMO level of the substance including a triazine skeleton or a diazine skeleton. The pyridine skeleton or the bipyridine skeleton may form a condensed ring, for example, may form a phenanthroline skeleton.

Examples of the first electron-transport material and the second electron-transport material include substances including dibenzoquinoxaline skeletons such as 2mDBTP-DBq-II, 2mDBTBPDBq-II, 2-{3-[3-(2,8-diphenyldibenzothiophen-4-yl)phenyl]phenyl}dibenzo[f,h]quinoxaline (abbreviation: 2mDBTBPDBq-III), 2-{3-[3-(6-phenyldibenzothiophen-4-yl)phenyl]phenyl}dibenzo[f,h]quinoxaline (abbreviation: 2mDBTBPDBq-IV), 2-[4-(9-phenyl-9H-carbazol-3-yl)phenyl]dibenzo[f,h]quinoxaline (abbreviation: PCPDBq), 2-[3-(3,6-diphenyl-9H-carbazol-9-yl)phenyl]dibenzo[f,h]quinoxaline (abbreviation: 2mCzP-DBq-III), 2-[3'-(9H-carbazol-9-yl)biphenyl-3-yl]dibenzo[f,h]quinoxaline (abbreviation: 2mCzBPDBq), 7-[3-(dibenzothiophen-4-yl)phenyl]dibenzo[f,h]quinoxaline (abbreviation: 7mDBTPDBq-II), and 7-[3'-(dibenzothiophen-4-yl)biphenyl-3-yl]dibenzo[f,h]quinoxaline (abbreviation: 7mDBTBPDBq-II); substances including benzoquinazoline skeletons such as 2,2'-(pyridine-2,6-diyl)bis(4-phenylbenzo[h]quinazoline) (abbreviation: 2,6(P-Bqn)2Py); substances including a pyrimidine skeleton such as 4,6mDBTP2Pm-II, 4,6-bis[3-(9H-carbazol-9-yl)phenyl]pyrimidine (abbreviation: 4,6mCzP2Pm), 4-[3'-(dibenzothiophen-4-yl)biphenyl-3-yl]benzofuro[3,2-d]pyrimidine (abbreviation: 4mDBTBPBfpm-II), 4-{3-[3'-(9H-carbazol-9-yl)]biphenyl-3-yl}benzofuro[3,2-d]pyrimidine (abbreviation: 4mCzBPBfPm), 4,6-bis[3,5-di(pyridin-3-yl)phenyl]-2-methylpyrimidine (abbreviation: B3PYMPM), and 2,2'-(pyridine-2,6-diyl)bis(4,6-diphenylpyrimidine) (abbreviation: 2,6(P2Pm)2Py); substances including pyrazine skeletons such as pyrazino[2,3-f][1,10]phenanthroline-2,3-dicarbonitrile (abbreviation: PPDN), 2,3-diphenylpyrido[2,3-b]pyrazine (abbreviation: 2PYPR), and 2,3-diphenylpyrido[3,4-b]pyrazine (abbreviation: 3PYPR); substances including triazine skeletons such as 2,4,6-tris(2-pyridyl)-1,3,5-triazine (abbreviation: 2Py3Tzn), 2,4,6-tris [3'-(pyridin-3-yl)biphenyl-3-yl]-1,3,5-triazine (abbreviation: TmPPPyTz), and 3-[4-(9H-carbazol-9-yl)phenyl]-9-(4,6-diphenyl-1,3,5-triazin-2-yl)-9H-carbazole (abbreviation: CPCBPTz); substances including phenanthroline skeletons such as bathocuproine (abbreviation: BCP), bathophenanthroline (abbreviation: Bphen), 2,9-bis(naphthalen-2-yl)-4,7-diphenyl-1,10-phenanthroline (abbreviation: NBPhen), and 4,4'-di(1,10-phenanthrolin-2-yl)biphenyl (abbreviation: Phen2BP); substances including bipyridine skeletons such as 4,4'-bis[3-(9H-carbazol-9-yl)phenyl]-2,2'-bipyridine (abbreviation: 4,4'mCzP2BPy), 4,4'-bis[3-(dibenzothiophen-4-yl)phenyl]-bipyridine (abbreviation: 4,4'mDBTP2BPy-II), and 4,4'-bis[3-(dibenzofuran-4-yl)phenyl]-2,2'-bipyridine (abbreviation: 4,4'DBfP2BPy-II); and substances including pyridine skeletons such as tris[2,4,6-trimethyl-3-(3-pyridyl)phenyl]borane (abbreviation: 3 TPYMB), 1,3,5-tri[3-(3-pyridyl)phenyl]benzene (abbreviation: TmPyPB), 3,3',5,5'-tetra[(m-pyridyl)-phen-3-yl]biphenyl (abbreviation: BP4mPy), and 1,3-bis[3,5-di(pyridin-3-yl)phenyl]benzene (abbreviation: BmPyPhB). Among these substances and the above-mentioned substances used as the host material, which include a condensed aromatic ring skeleton including 3 to 6 rings, materials may be selected such that the LUMO level of the host material and the LUMO level of the second electron-transport material are higher (shallower) than the LUMO level of the first electron-transport material.

The charge-generation layer 116 may be further provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials that are given above as examples of the materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the second electron-transport layer 114-2 and holes are injected into the second electrode 102; thus, the light-emitting element operates.

Note that the charge-generation layer 116 preferably includes one or both of an electron-relay layer 118 and an electron-injection buffer layer 119 in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used.

For the cathode, any of metals, alloys, electrically conductive compounds, and mixtures thereof which have a low work function (specifically, a work function of 3.8 eV or less) can be used, for example. Specific examples of such a cathode material are elements belonging to Group 1 or 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), and alloys thereof. However, when the electron-injection layer is provided between the cathode and the electron-transport layer, any of a variety of conductive materials such as Al, Ag, ITO, or indium oxide-tin oxide containing silicon or silicon oxide can be used for the cathode regardless of the work function. Films of these conductive materials can be formed by a dry method such as a vacuum evaporation method or a sputtering method, an inkjet method, a spin coating method, or the like. In addition, the films may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, or a spin coating method may be used.

The electrodes or the layers described above may be formed by different methods.

Here, a method for forming an EL layer 786 by a droplet discharge method is described with reference to FIGS. 2A to 2D. FIGS. 2A to 2D are cross-sectional views illustrating the method for forming the EL layer 786.

Figure 2A:
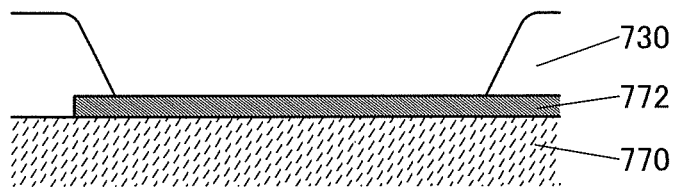
FIGS. 2A to 2D illustrate an example of a method for manufacturing a light-emitting element.
Figure 2B:
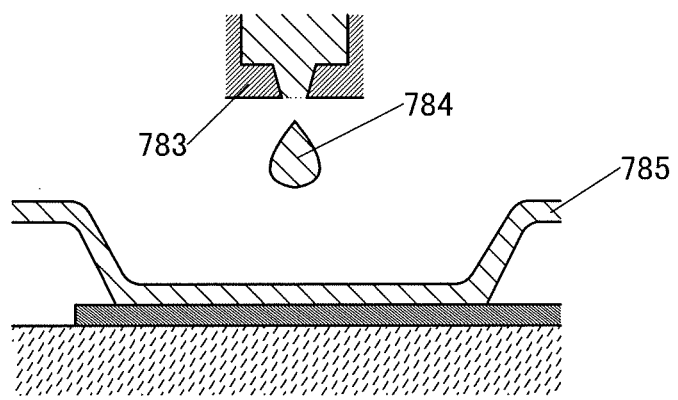

First, a conductive film 772 is formed over a planarization insulating film 770, and an insulating film 730 is formed to cover part of the conductive film 772 (see FIG. 2A).

Then, a droplet 784 is discharged to an exposed portion of the conductive film 772, which is an opening of the insulating film 730, from a droplet discharge apparatus 783, so that a layer 785 containing a composition is formed. The droplet 784 is a composition containing a solvent and is attached to the conductive film 772 (see FIG. 2B).

Note that the step of discharging the droplet 784 may be performed under reduced pressure.

Figure 2C:
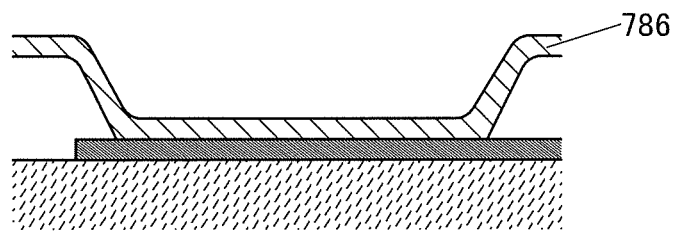

Next, the solvent is removed from the layer 785 containing a composition, and the resulting layer is solidified to form the EL layer 786 (see FIG. 2C).

The solvent may be removed by drying or heating.

Figure 2D:
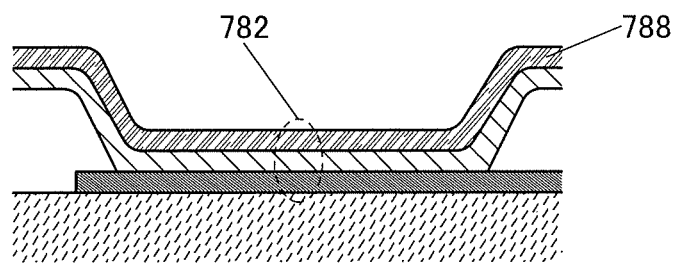

Next, a conductive film 788 is formed over the EL layer 786; thus, a light-emitting element 782 is completed (see FIG. 2D).

When the EL layer 786 is formed by a droplet discharge method as described above, the composition can be selectively discharged; accordingly, waste of material can be reduced. Furthermore, a lithography process or the like for shaping is not needed, and thus, the process can be simplified and cost reduction can be achieved.

The droplet discharge method described above is a general term for a means including a nozzle equipped with a composition discharge outlet or a means to discharge droplets, such as a head having one or a plurality of nozzles.

Figure 3:
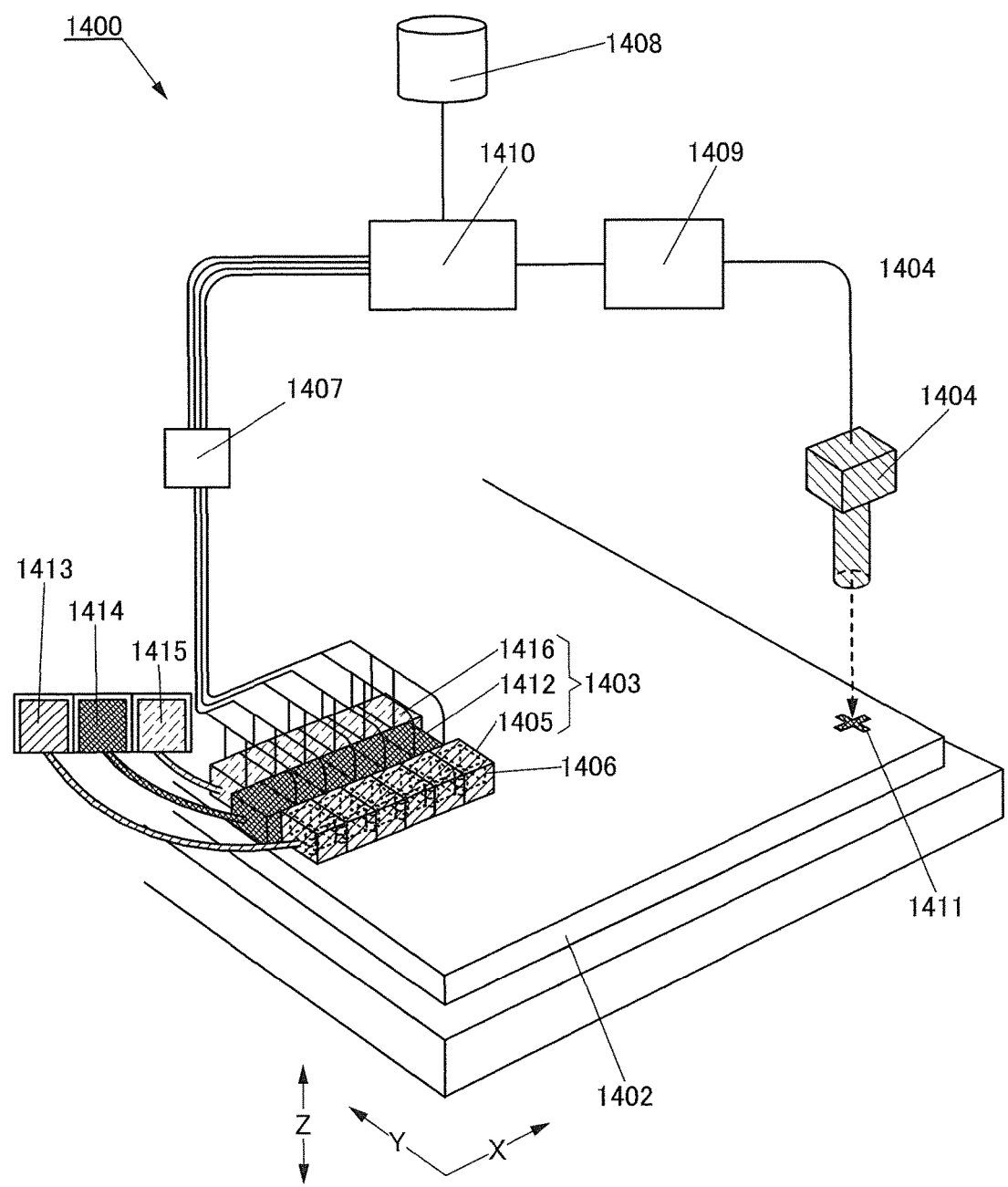
FIG. 3 illustrates an example of a manufacturing apparatus of a light-emitting element.

Next, a droplet discharge apparatus used for the droplet discharge method is described with reference to FIG. 3. FIG. 3 is a conceptual diagram illustrating a droplet discharge apparatus 1400.

The droplet discharge apparatus 1400 includes a droplet discharge means 1403. The droplet discharge means 1403 is equipped with a head 1405, a head 1412, and a head 1416.

The heads 1405 and 1412 are connected to a control means 1407, and this control means 1407 is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. Then, the digital signal is recognized by the computer 1410, and then, a control signal is generated and transmitted to the control means 1407.

An image sensor or the like using a charge coupled device (CCD) or a complementary metal oxide semiconductor (CMOS) can be used as the imaging means 1404. Note that information about a pattern to be formed over the substrate 1402 is stored in a storage medium 1408, and a control signal is transmitted to the control means 1407 on the basis of the information, so that each of the heads 1405, 1412, and 1416 of the droplet discharge means 1403 can be individually controlled. A material to be discharged is supplied to the heads 1405, 1412, and 1416 from material supply sources 1413, 1414, and 1415, respectively, through pipes.

Inside each of the heads 1405, 1412, and 1416, a space as indicated by a dotted line 1406 to be filled with a liquid material and a nozzle which is a discharge outlet are provided. Although not illustrated, an inside structure of the head 1412 is similar to that of the head 1405. When the nozzle sizes of the heads 1405 and 1412 are different from each other, different materials with different widths can be discharged simultaneously. Each head can discharge and draw a plurality of light-emitting materials. In the case of drawing over a large area, the same material can be simultaneously discharged to be drawn from a plurality of nozzles in order to improve throughput. When a large substrate is used, the heads 1405, 1412, and 1416 can freely scan the substrate in the directions indicated by arrows X, Y, and Z in FIG. 3, and a region in which a pattern is drawn can be freely set. Thus, a plurality of the same patterns can be drawn over one substrate.

Furthermore, a step of discharging the composition may be performed under reduced pressure. Also, a substrate may be heated when the composition is discharged. After discharging the composition, either drying or baking or both is performed. Both the drying and baking are heat treatments but different in purpose, temperature, and time period. The steps of drying and baking are performed under normal pressure or under reduced pressure by laser irradiation, rapid thermal annealing, heating using a heating furnace, or the like. Note that the timing of the heat treatment and the number of times of the heat treatment are not particularly limited. The temperature for performing the steps of drying and baking in a favorable manner depends on the material of the substrate and the properties of the composition.

In the above-described manner, the EL layer 786 can be formed with the droplet discharge apparatus.

In the case where the EL layer 786 is formed with the droplet discharge apparatus, the EL layer 786 can be formed by a wet method using a composition in which an organic compound is dissolved in a solvent. In that case, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, cyclohexane, and the like. In particular, less polar benzene derivatives such as benzene, toluene, xylene, and mesitylene are preferable because a solution with a suitable concentration can be obtained and the organic compound contained in ink can be prevented from deteriorating due to oxidation or the like. Furthermore, to achieve a uniform film or a film with a uniform thickness, a solvent with a boiling point of 100° C. or higher is preferably used, and more preferably, toluene, xylene, or mesitylene is used.

Note that the above-described structure can be combined with any of the structures in this embodiment.

The electrode may be formed by a wet method using a sol-gel method, or by a wet method using paste of a metal material. The electrode may also be formed by a dry method such as a sputtering method or a vacuum evaporation method.

Light emission from the light-emitting element is extracted out through one or both of the first electrode 101 and the second electrode 102. Therefore, one or both of the first electrode 101 and the second electrode 102 are formed as a light-transmitting electrode.

Furthermore, in order that the transfer of energy from an exciton generated in the light-emitting layer can be suppressed, preferably, the hole-transport layer and the electron-transport layer, which are in contact with the light-emitting layer 113, particularly a carrier-transport layer closer to the recombination region in the light-emitting layer 113, are formed using a substance having a wider band gap than the light-emitting substance of the light-emitting layer or an emission center substance included in the light-emitting layer.

Next, an embodiment of a light-emitting element with a structure in which a plurality of light-emitting units are stacked (this type of light-emitting element is also referred to as a stacked or tandem light-emitting element) is described with reference to FIG. 1C. This light-emitting element includes a plurality of light-emitting units between an anode and a cathode. One light-emitting unit has a structure similar to that of the EL layer 103, which is illustrated in FIG. 1A or 1B. In other words, the light-emitting element illustrated in FIG. 1A or 1B includes a single light-emitting unit, and the light-emitting element illustrated in FIG. 1C includes a plurality of light-emitting units.

Figure 1C:
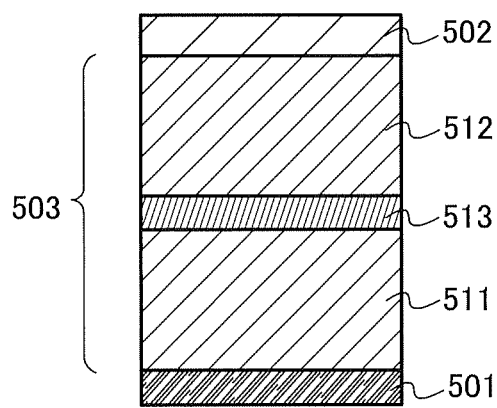

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the structure of the charge-generation layer 116 described with reference to FIG. 1B. The composite material of an organic compound and a metal oxide has a high carrier-injection property and a high carrier-transport property; thus, low-voltage driving and low-current driving can be achieved. Note that when a surface of a light-emitting unit on the anode side is in contact with the charge-generation layer 513, the charge-generation layer 513 can also function as a hole-injection layer in the light-emitting unit and thus, a hole-injection layer is not necessarily formed in the light-emitting unit.

In the case where the electron-injection buffer layer 119 is provided, the electron-injection buffer layer 119 functions as the electron-injection layer in the light-emitting unit on the anode side and thus, an electron-injection layer is not necessarily &glued in the light-emitting unit on the anode side.

The light-emitting element including two light-emitting units is described with reference to FIG. 1C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide an element that can emit light with high luminance with the current density kept low and has a long lifetime. Moreover, a light-emitting device of low power consumption, which can be driven at low voltage, can be achieved.

When light-emitting units have different emission colors, light emission of a desired color can be obtained as a whole light-emitting element. For example, it is easy to enable a light-emitting element having two light-emitting units to emit white light as the whole element when the emission colors of the first light-emitting unit are red and green and the emission color of the second light-emitting unit is blue.

Note that the above-described structure can be combined with any of the structures in this embodiment as appropriate.

<<Micro Optical Resonator (Microcavity) Structure>>

A light-emitting element with a microcavity structure is formed with the use of a reflective electrode and a semi-transmissive and semi-reflective electrode as the pair of electrodes. The reflective electrode and the semi-transmissive and semi-reflective electrode correspond to the first electrode and the second electrode described above. The light-emitting element with a microcavity structure includes at least an EL layer between the reflective electrode and the semi-transmissive and semi-reflective electrode. The EL layer includes at least a light-emitting layer functioning as a light-emitting region.

Light emitted from the light-emitting layer included in the EL layer is reflected and resonated by the reflective electrode and the semi-transmissive and semi-reflective electrode. Note that the reflective electrode has a visible light reflectivity of 40% to 100%, preferably 70% to 100% and a resistivity of $1 \times 10^{-2}$ Ωcm or lower. In addition, the semi-transmissive and semi-reflective electrode has a visible light reflectivity of 20% to 80%, preferably 40% to 70%, and a resistivity of $1 \times 10^{-2}$ Ωcm or lower.

In the light-emitting element, by changing the thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is emitted from the light-emitting layer and reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of a color to be amplified). In that case, the phases of the first reflected light and the first incident light can be aligned with each other and the light emitted from the light-emitting layer can be further amplified.

Note that in the above structure, the EL layer may be formed of a plurality of light-emitting layers or may be a single light-emitting layer. The tandem light-emitting element described above may be combined with the EL layer; for example, a light-emitting element may have a structure in which a plurality of EL layers are provided, a charge-generation layer is provided between the EL layers, and each EL layer is formed of a plurality of light-emitting layers or a single light-emitting layer.

<<Light-Emitting Device>>

Figure 4A:
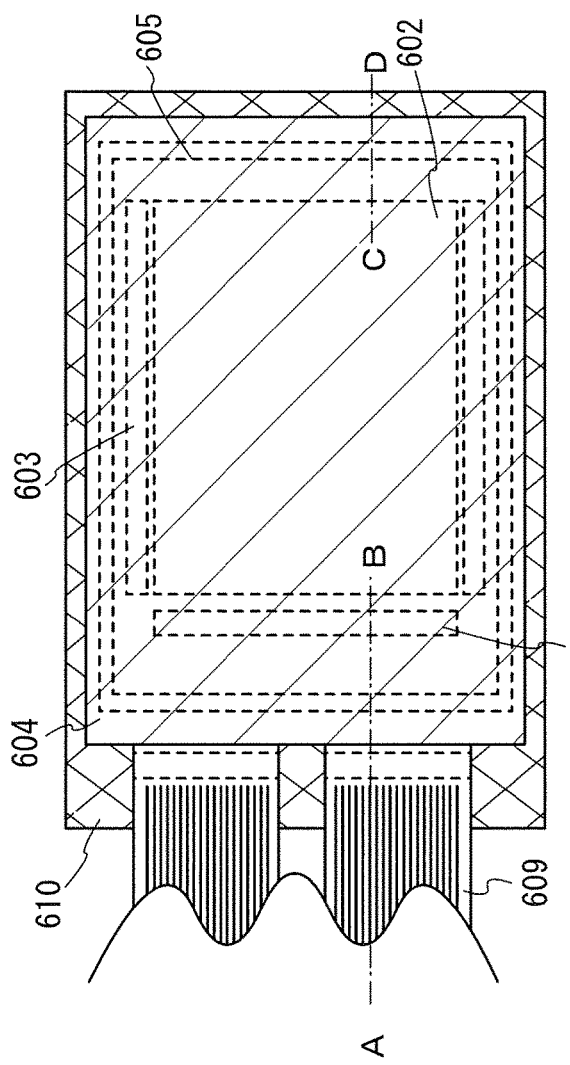
FIGS. 4A and 4B are conceptual diagrams of an active matrix light-emitting device.
Figure 4B:
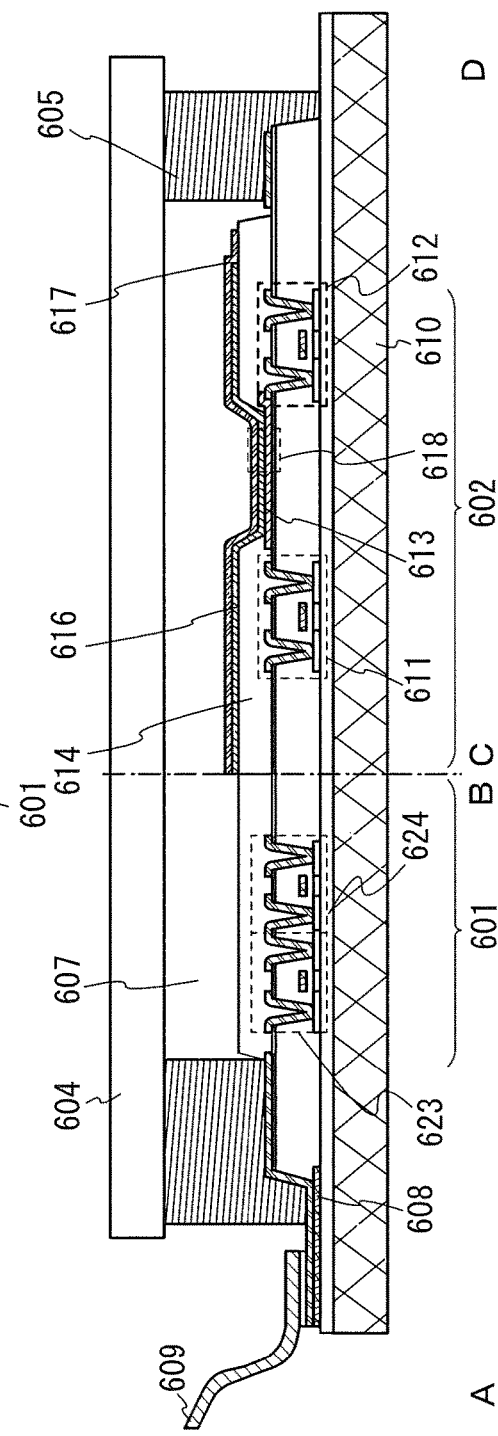

A light-emitting device of one embodiment of the present invention will be described with reference to FIGS. 4A and 4B. Note that FIG. 4A is a top view of the light-emitting device and FIG. 4B is a cross-sectional view taken along the lines A-B and C-D in FIG. 4A. The light-emitting device includes a driver circuit portion (source line driver circuit) 601, a pixel portion 602, and a driver circuit portion (gate line driver circuit) 603, which control light emission of a light-emitting element and are illustrated with dotted lines. Furthermore, reference numeral 604 denotes a sealing substrate and reference numeral 605 denotes a sealant. A portion surrounded by the sealant 605 is a space 607.

Note that a lead wiring 608 is a wiring for transmitting signals to be input to the source line driver circuit 601 and the gate line driver circuit 603 and for receiving a video signal, a clock signal, a start signal, a reset signal, and the like from an FPC (flexible printed circuit) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure is described with reference to FIG. 4B. The driver circuit portion and the pixel portion are formed over an element substrate 610. Here, the source line driver circuit 601, which is the driver circuit portion, and one pixel of the pixel portion 602 are illustrated.

In the source line driver circuit 601, a CMOS circuit is formed in which an n-channel FET 623 and a p-channel FET 624 are combined. The driver circuit may be formed using various circuits such as a CMOS circuit, a PMOS circuit, or an NMOS circuit. Although a driver-integrated type where the driver circuit is formed over the substrate is described in this embodiment, a driver circuit is not necessarily formed over a substrate; a driver circuit may be formed outside a substrate.

The pixel portion 602 includes a plurality of pixels including a switching FET 611, a current controlling FET 612, and a first electrode 613 electrically connected to a drain of the current controlling FET 612. One embodiment of the present invention is not limited to this structure. The pixel portion may include three or more FETs and a capacitor in combination.

The kind and crystallinity of a semiconductor used for the FETs are not particularly limited; an amorphous semiconductor or a crystalline semiconductor may be used. Examples of the semiconductor used for the FETs include Group 13 semiconductor, Group 14 semiconductor, compound semiconductor, oxide semiconductor, and organic semiconductor materials. Oxide semiconductors are particularly preferable. Examples of the oxide semiconductor include an In—Ga oxide and an In-M-Zn oxide (M is Al, Ga, Y, Zr, La, Ce, or Nd). Note that an oxide semiconductor material that has an energy gap of 2 eV or more, preferably 2.5 eV or more, more preferably 3 eV or more is preferably used, in which case the off-state current of the transistors can be reduced.

Note that an insulator 614 is formed so as to cover an end portion of the first electrode 613. The insulator 614 can be formed using a positive photosensitive acrylic resin film here.

In order to improve the coverage, the insulator 614 is formed to have a curved surface with curvature at its upper or lower end portion. For example, in the case where a positive photosensitive acrylic resin is used for a material of the insulator 614, only the upper end portion of the insulator 614 preferably has a curved surface with a curvature radius (0.2 μm to 3 μm). Moreover, either a negative photosensitive resin or a positive photosensitive resin can be used for the insulator 614.

An EL layer 616 and a second electrode 617 are formed over the first electrode 613. The first electrode 613, the EL layer 616, and the second electrode 617 correspond, respectively, to the first electrode 101, the EL layer 103, and the second electrode 102 in FIG. 1A or 1B, and correspond, respectively, to the first electrode 501, an EL layer 503, and the second electrode 502 in FIG. 1C.

The EL layer 616 preferably contains an organometallic complex. The organometallic complex is preferably used as an emission center substance in the light-emitting layer.

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with filler, and may be filled with an inert gas (e.g., nitrogen or argon) or the sealant 605. It is preferable that the sealing substrate 604 be provided with a recessed portion and a drying agent be provided in the recessed portion, in which case deterioration due to the influence of moisture can be suppressed.

An epoxy-based resin or glass frit is preferably used for the sealant 605. A material used for them is desirably a material that transmits moisture or oxygen as less as possible. As the element substrate 610 and the sealing substrate 604, a glass substrate, a quartz substrate, or a plastic substrate formed of fiber reinforced plastic (FRP), polyvinyl fluoride (PVF), polyester, acrylic, or the like can be used.

In this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used. As an example of a glass substrate, a barium borosilicate glass substrate, an aluminoborosilicate glass substrate, a soda lime glass substrate, or the like can be given. Examples of the flexible substrate, the attachment film, the base material film, or the like are as follows: plastic typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic film formed by evaporation, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly on the flexible substrate. Still alternatively, a separation layer may be provided between a substrate and the transistor or between the substrate and the light-emitting element. The separation layer can be used when part or the whole of a semiconductor device formed over the separation layer is separated from the substrate and transferred onto another substrate. In such a case, the transistor can be transferred to a substrate having low heat resistance or a flexible substrate as well. For the above separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of the substrate to which the transistor or the light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent properties or a transistor with low power consumption can be formed, a device with high durability and high heat resistance can be provided, or a reduction in weight or thickness can be achieved.

Figures 5A, 5B:
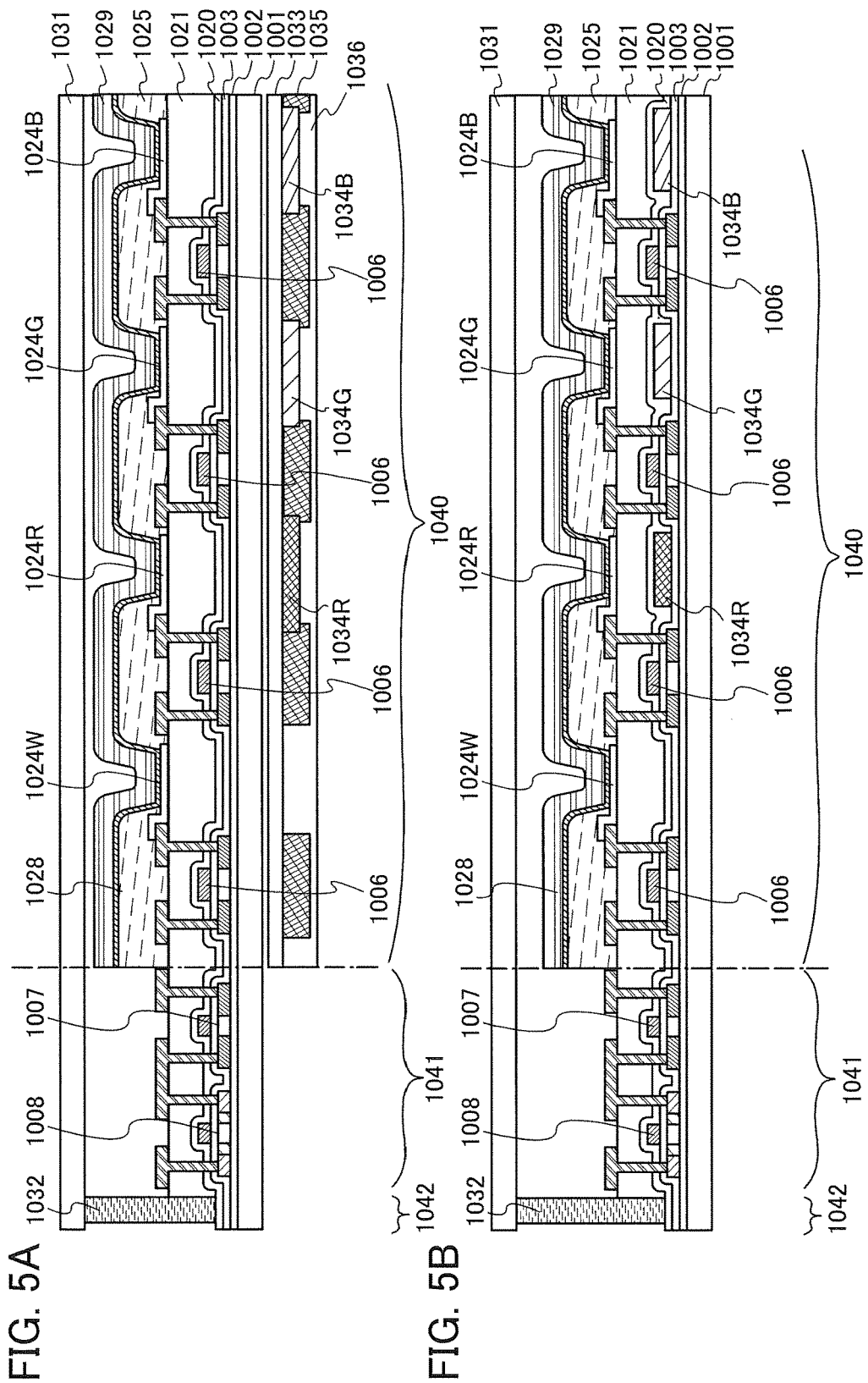
FIGS. 5A and 5B are conceptual diagrams of an active matrix light-emitting device.

FIGS. 5A and 5B each illustrate an example of a light-emitting device in which full color display is achieved by forming a light-emitting element exhibiting white light emission and using coloring layers (color filters) and the like. FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer. In FIG. 5A, light emitted from some of the light-emitting layers does not pass through the coloring layers, while light emitted from the others of the light-emitting layers passes through the coloring layers. Since light that does not pass through the coloring layers is white and light that passes through any one of the coloring layers is red, blue, or green, an image can be displayed using pixels of the four colors.

FIG. 5B illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 6:
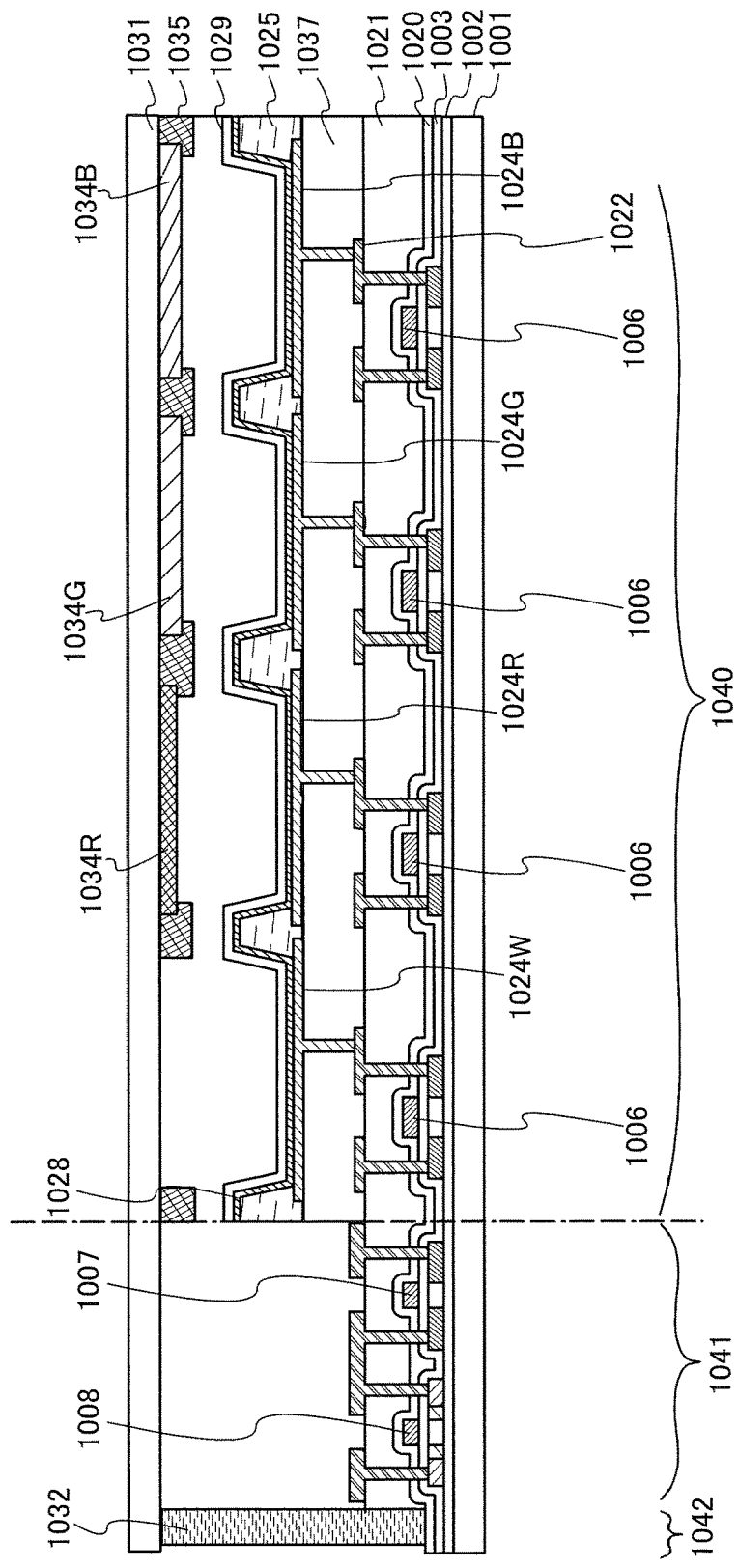
FIG. 6 is a conceptual diagram of an active matrix light-emitting device.

The above-described light-emitting device has a structure in which light is extracted from the substrate 1001 side where the FETs are formed (a bottom emission structure), but may have a structure in which light is extracted from the sealing substrate 1031 side (a top emission structure). FIG. 6 is a cross-sectional view of a light-emitting device having a top emission structure. In that case, a substrate that does not transmit light can be used as the substrate 1001. The process up to the step of forming of a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The first electrodes 1024W, 1024R, 1024G, and 1024B of the light-emitting elements each function as an anode here, but may function as a cathode. Furthermore, in the case of the light-emitting device having a top emission structure as illustrated in FIG. 6, the first electrodes are preferably reflective electrodes. The EL layer 1028 is formed to have a structure similar to the structure of the EL layer 103 in FIG. 1A or 1B or the EL layer 503 in FIG. 1C, with which white light emission can be obtained.

In the case of a top emission structure as illustrated in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Figure 7A:
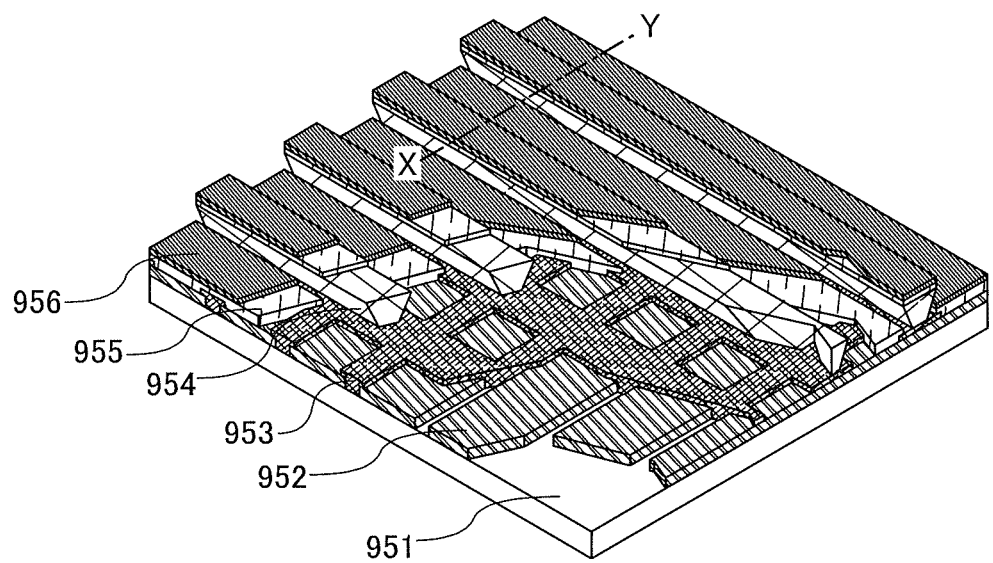
FIGS. 7A and 7B are conceptual diagrams of a passive matrix light-emitting device.
Figure 7B:
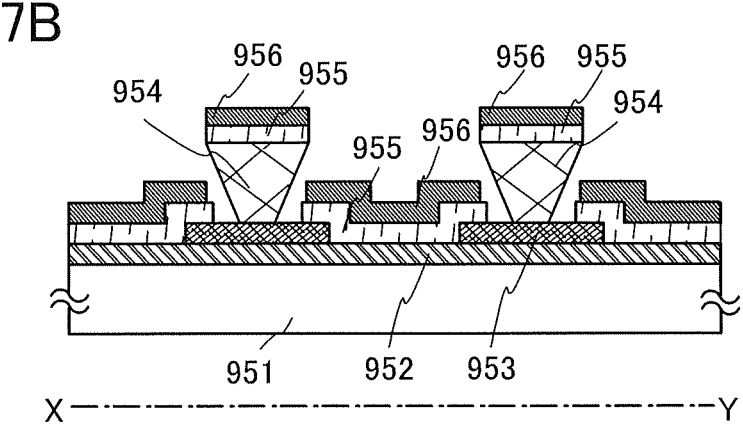

FIGS. 7A and 7B illustrate a passive matrix light-emitting device of one embodiment of the present invention. FIG. 7A is a perspective view of a light-emitting device, and FIG. 7B is a cross-sectional view taken along the line X-Y of FIG. 7A. In FIGS. 7A and 7B, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between the sidewalls is gradually narrowed toward the surface of the substrate. That is, a cross section in a short side direction of the partition layer 954 is a trapezoidal shape, and a lower side (the side facing the same direction as the plane direction of the insulating layer 953 and touching the insulating layer 953) is shorter than an upper side (the side facing the same direction as the plane direction of the insulating layer 953, and not touching the insulating layer 953). By providing the partition layer 954 in this manner, defects of the light-emitting element due to static charge and the like can be prevented.

Since many minute light-emitting elements arranged in a matrix can be controlled with the FETs formed in the pixel portion, the above-described light-emitting device can be suitably used as a display device for displaying images.

<<Lighting Device>>

Figure 8A:
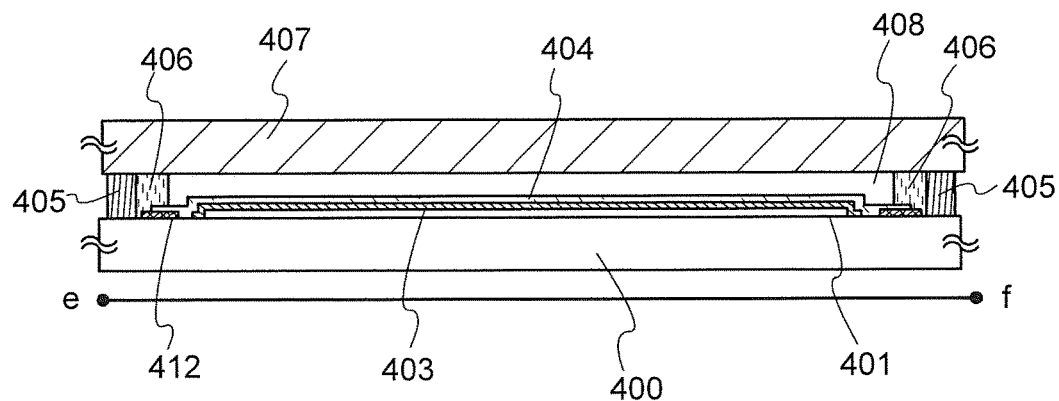
FIGS. 8A and 8B illustrate a lighting device.
Figure 8B:
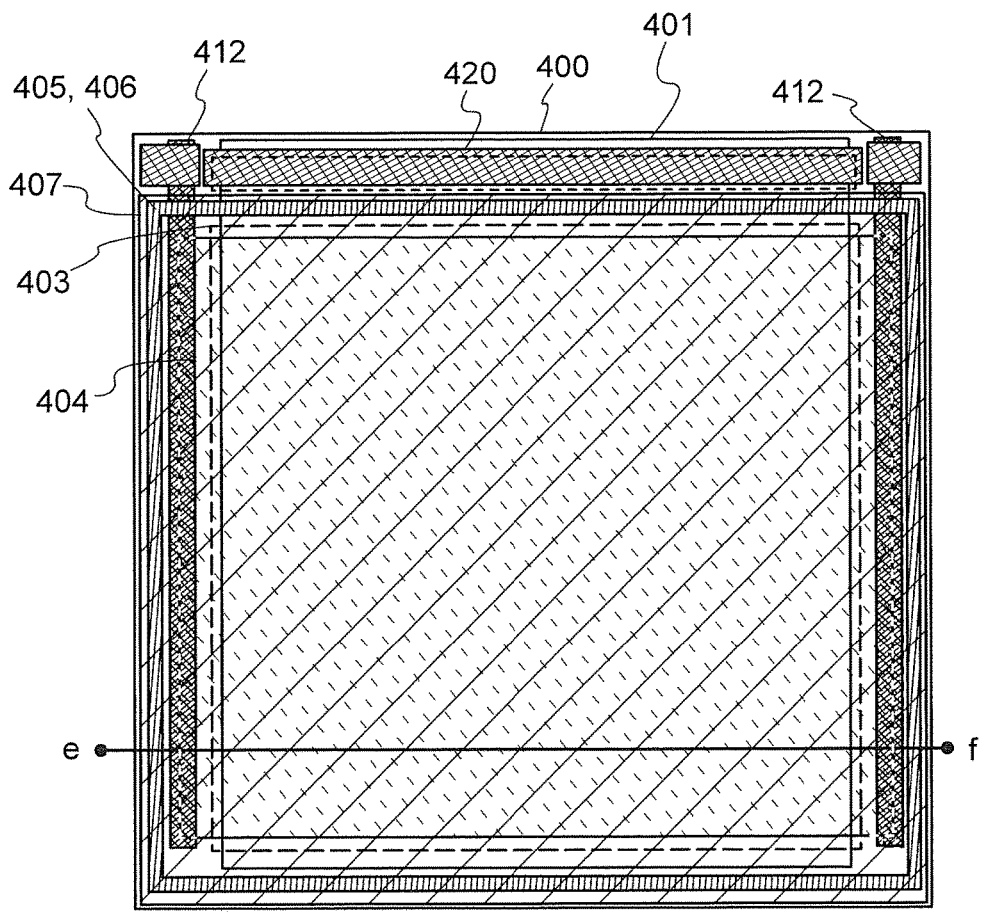

A lighting device of one embodiment of the present invention is described with reference to FIGS. 8A and 8B. FIG. 8B is a top view of the lighting device, and FIG. 8A is a cross-sectional view taken along the line e-f in FIG. 8B.

In the lighting device, a first electrode 401 is formed over a substrate 400 which is a support and has a light-transmitting property. The first electrode 401 corresponds to the first electrode 101 in FIG. 1A or 1B. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The EL layer 403 corresponds to, for example, the EL layer 103 in FIG. 1A or 1B. For these structures, the corresponding description can be referred to.

The second electrode 404 is formed to cover the EL layer 403. The second electrode 404 corresponds to the second electrode 102 in FIG. 1A or 1B. The second electrode 404 contains a material having high reflectivity when light is extracted through the first electrode 401 side. The second electrode 404 is connected to the pad 412, whereby voltage is applied thereto.

A light-emitting element is formed with the first electrode 401, the EL layer 403, and the second electrode 404. The light-emitting element is fixed to a sealing substrate 407 with sealants 405 and 406 and sealing is performed, whereby the lighting device is completed. It is possible to use only either the sealant 405 or the sealant 406. In addition, the inner sealant 406 (not illustrated in FIG. 8B) can be mixed with a desiccant that enables moisture to be adsorbed, which results in improved reliability.

When part of the pad 412 and part of the first electrode 401 are extended to the outside of the sealants 405 and 406, the extended parts can function as external input terminals. An IC chip 420 mounted with a converter or the like may be provided over the external input terminals.

<<Display Device>>

An example of a display panel that can be used for a display portion or the like in a display device including the semiconductor device of one embodiment of the present invention will be described below with reference to FIG. 16 and FIG. 17. The display panel exemplified below includes both a reflective liquid crystal element and a light-emitting element and can display an image in both the transmissive mode and the reflective mode.

<6-1. Structure Example of Display Panel>

Figure 16:
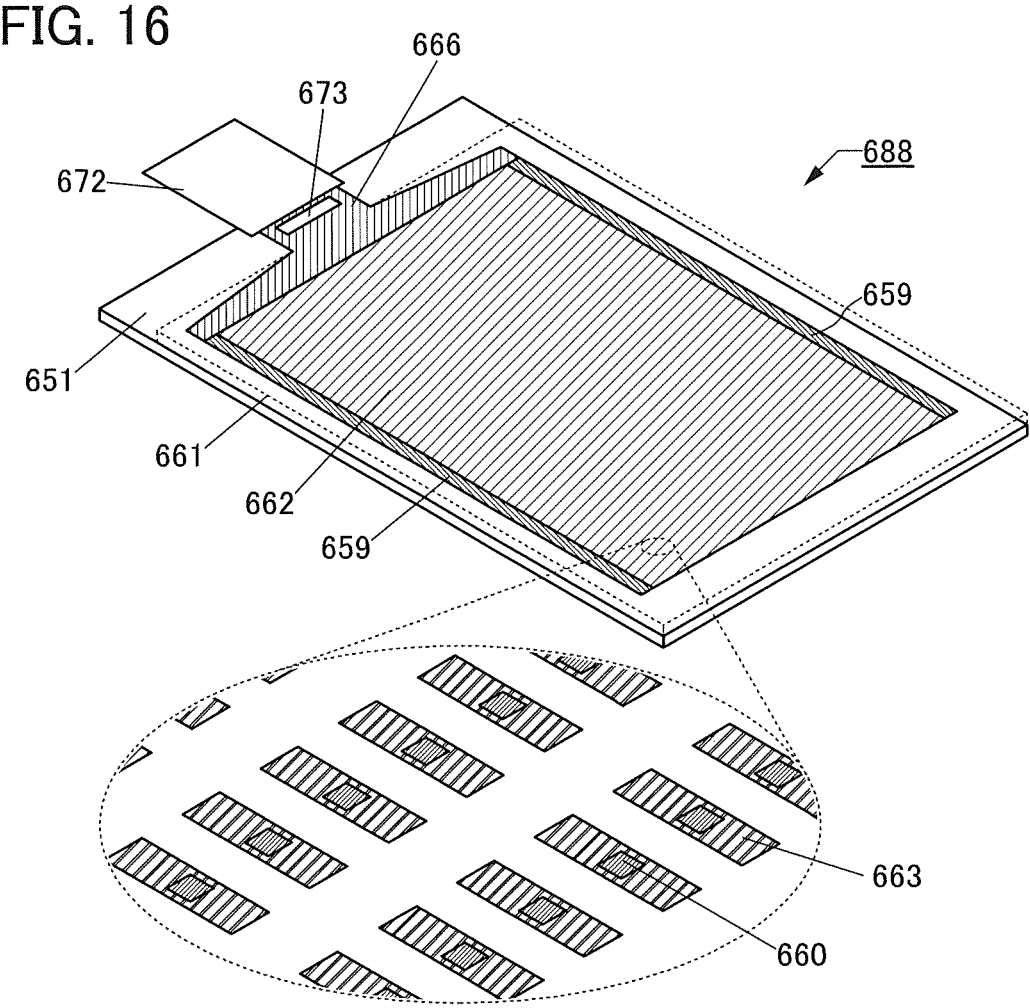
FIG. 16 illustrates a structure example of a display panel.

FIG. 16 is a schematic perspective view illustrating a display panel 688 of one embodiment of the present invention. In the display panel 688, a substrate 651 and a substrate 661 are attached to each other. In FIG. 16, the substrate 661 is denoted by a dashed line.

The display panel 688 includes a display portion 662, a circuit 659, a wiring 666, and the like. The substrate 651 is provided with the circuit 659, the wiring 666, a conductive film 663 which serves as a pixel electrode, and the like. In the example of FIG. 16, an IC 673 and an FPC 672 are mounted on the substrate 651. Thus, the structure illustrated in FIG. 16 can be referred to as a display module including the display panel 688, the FPC 672, and the IC 673.

As the circuit 659, for example, a circuit functioning as a scan line driver circuit can be used.

The wiring 666 has a function of supplying a signal or electric power to the display portion 662 or the circuit 659. The signal or electric power is input to the wiring 666 from the outside through the FPC 672 or from the IC 673.

FIG. 16 shows an example in which the IC 673 is provided on the substrate 651 by a chip on glass (COG) method or the like. As the IC 673, an IC functioning as a scan line driver circuit, a signal line driver circuit, or the like can be used. Note that it is possible that the IC 673 is not provided when, for example, the display panel 688 includes circuits serving as a scan line driver circuit and a signal line driver circuit and when the circuits serving as a scan line driver circuit and a signal line driver circuit are provided outside and a signal for driving the display panel 688 is input through the FPC 672. Alternatively, the IC 673 may be mounted on the FPC 672 by a chip on film (COF) method or the like.

FIG. 16 also shows an enlarged view of part of the display portion 662. The conductive films 663 included in a plurality of display elements are arranged in a matrix in the display portion 662. The conductive film 663 has a function of reflecting visible light and serves as a reflective electrode of a liquid crystal element 640 described later.

As illustrated in FIG. 16, the conductive film 663 has an opening. A light-emitting element 660 is positioned closer to the substrate 651 than the conductive film 663 is. Light is emitted from the light-emitting element 660 to the substrate 661 side through the opening in the conductive film 663. When the light-emitting element of one embodiment of the present invention is used as the light-emitting element 660, a display panel with a long lifetime can be provided. A display panel including a light-emitting element with high emission efficiency can be provided. Furthermore, when the light-emitting element of one embodiment of the present invention is used as the light-emitting element 660, a display panel including a blue light-emitting element with high emission efficiency can be provided.

<6-2. Cross-Sectional Structure Example>

Figure 17:
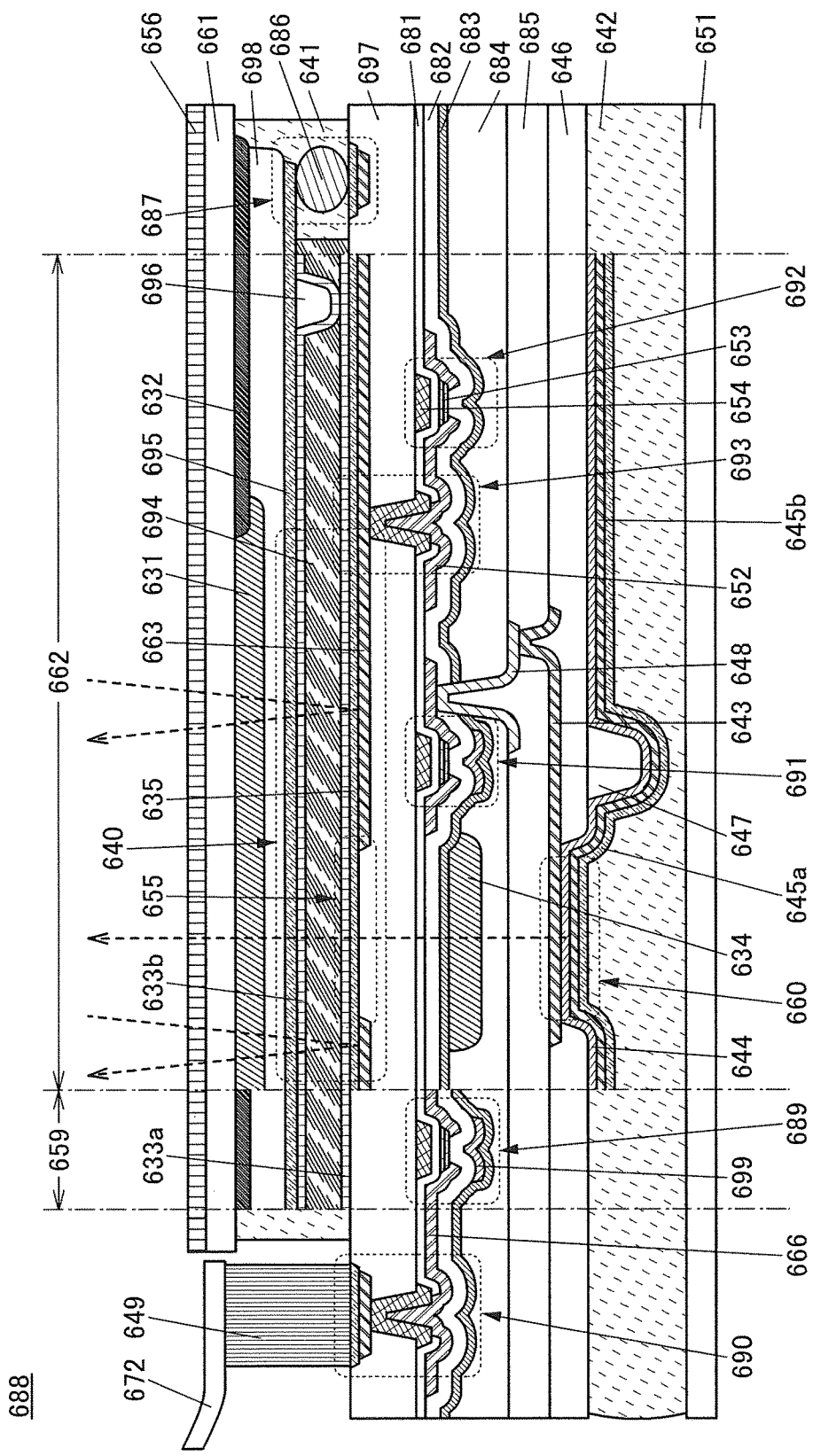
FIG. 17 illustrates a structure example of a display panel.

FIG. 17 shows an example of cross sections of part of a region including the FPC 672, part of a region including the circuit 659, and part of a region including the display portion 662 of the display panel illustrated in FIG. 16.

The display panel includes an insulating film 697 between the substrates 651 and 661. The display panel also includes the light-emitting element 660, a transistor 689, a transistor 691, a transistor 692, a coloring layer 634, and the like between the substrate 651 and the insulating film 697. Furthermore, the display panel includes the liquid crystal element 640, a coloring layer 631, and the like between the insulating film 697 and the substrate 661. The substrate 661 and the insulating film 697 are bonded with an adhesive layer 641. The substrate 651 and the insulating film 697 are bonded with an adhesive layer 642.

The transistor 692 is electrically connected to the liquid crystal element 640 and the transistor 691 is electrically connected to the light-emitting element 660. Since the transistors 691 and 692 are formed on a surface of the insulating film 697 that is on the substrate 651 side, the transistors 691 and 692 can be formed through the same process.

The substrate 661 is provided with the coloring layer 631, a light-blocking film 632, an insulating film 698, a conductive film 695 serving as a common electrode of the liquid crystal element 640, an alignment film 633b, an insulating film 696, and the like. The insulating film 696 serves as a spacer for holding a cell gap of the liquid crystal element 640.

Insulating layers such as an insulating film 681, an insulating film 682, an insulating film 683, an insulating film 684, and an insulating film 685 are provided on the substrate 651 side of the insulating film 697. Part of the insulating film 681 functions as a gate insulating layer of each transistor. The insulating films 682, 683, and 684 are provided to cover each transistor. The insulating film 685 is provided to cover the insulating film 684. The insulating films 684 and 685 each function as a planarization layer. Note that here, the three insulating layers, the insulating films 682, 683, and 684, are provided to cover the transistors and the like; however, one embodiment of the present invention is not limited to this example, and four or more insulating layers, a single insulating layer, or two insulating layers may be provided. The insulating film 684 functioning as a planarization layer is not necessarily provided.

The transistors 689, 691, and 692 each include a conductive film 654 part of which functions as a gate, a conductive film 652 part of which functions as a source or a drain, and a semiconductor film 653. Here, a plurality of layers obtained by processing the same conductive film are shown with the same hatching pattern.

The liquid crystal element 640 is a reflective liquid crystal element. The liquid crystal element 640 has a stacked structure of a conductive film 635, a liquid crystal layer 694, and the conductive film 695. In addition, the conductive film 663 which reflects visible light is provided in contact with the surface of the conductive film 635 that faces the substrate 651. The conductive film 663 includes an opening 655. The conductive films 635 and 695 contain a material that transmits visible light. In addition, an alignment film 633a is provided between the liquid crystal layer 694 and the conductive film 635 and the alignment film 633b is provided between the liquid crystal layer 694 and the conductive film 695. A polarizing plate 656 is provided on an outer surface of the substrate 661.

In the liquid crystal element 640, the conductive film 663 has a function of reflecting visible light and the conductive film 695 has a function of transmitting visible light. Light entering from the substrate 661 side is polarized by the polarizing plate 656, passes through the conductive film 695 and the liquid crystal layer 694, and is reflected by the conductive film 663. Then, the light passes through the liquid crystal layer 694 and the conductive film 695 again and reaches the polarizing plate 656. In this case, the alignment of the liquid crystal is controlled with a voltage that is applied between the conductive film 663 and the conductive film 695, and thus optical modulation of light can be controlled. That is, the intensity of light emitted through the polarizing plate 656 can be controlled. Light excluding light in a particular wavelength region is absorbed by the coloring layer 631, and thus, red light is emitted, for example.

The light-emitting element 660 is a bottom-emission light-emitting element. The light-emitting element 660 has a structure in which a conductive film 643, an EL layer 644, and a conductive film 645b are stacked in this order from the insulating film 697 side. In addition, a conductive film 645a is provided to cover the conductive film 645b. The conductive film 645b contains a material reflecting visible light, and the conductive films 643 and 645a contain a material transmitting visible light. Light is emitted from the light-emitting element 660 to the substrate 661 side through the coloring layer 634, the insulating film 697, the opening 655, the conductive film 695, and the like.

Here, as illustrated in FIG. 17, the conductive film 635 transmitting visible light is preferably provided for the opening 655. Accordingly, the liquid crystal layer 694 is aligned in a region overlapping with the opening 655 as well as in the other regions, so that undesired light leakage due to an alignment defect of the liquid crystal in the boundary portion of these regions can be prevented.

As the polarizing plate 656 provided on an outer surface of the substrate 661, a linear polarizing plate or a circularly polarizing plate can be used. An example of the circularly polarizing plate is a stack including a linear polarizing plate and a quarter-wave retardation plate. Such a structure can reduce reflection of external light. The cell gap, alignment, driving voltage, and the like of the liquid crystal element used as the liquid crystal element 640 are controlled depending on the kind of the polarizing plate so that a desirable contrast can be obtained.

In addition, an insulating film 647 is provided on the insulating film 646 covering an end portion of the conductive film 643. The insulating film 647 has a function as a spacer for preventing the insulating film 697 and the substrate 651 from getting closer more than necessary. In the case where the EL layer 644 or the conductive film 645a is formed using a blocking mask (metal mask), the insulating film 647 may have a function of preventing the blocking mask from being in contact with a surface on which the EL layer 644 or the conductive film 645a is formed. Note that the insulating film 647 is not necessarily provided.

One of a source and a drain of the transistor 691 is electrically connected to the conductive film 643 of the light-emitting element 660 through a conductive film 648.

One of a source and a drain of the transistor 692 is electrically connected to the conductive film 663 through a connection portion 693. The conductive films 663 and 635 are in contact with and electrically connected to each other. Here, in the connection portion 693, the conductive layers provided on both surfaces of the insulating film 697 are connected to each other through an opening in the insulating film 697.

A connection portion 690 is provided in a region of the substrate 651 that does not overlap with the substrate 661. The connection portion 690 is electrically connected to the FPC 672 through a connection layer 649. The connection portion 690 has a structure similar to that of the connection portion 693. On the top surface of the connection portion 690, a conductive layer obtained by processing the same conductive film as the conductive film 635 is exposed. Thus, the connection portion 690 and the FPC 672 can be electrically connected to each other through the connection layer 649.

A connection portion 687 is provided in part of a region where the adhesive layer 641 is provided. In the connection portion 687, the conductive layer obtained by processing the same conductive film as the conductive film 635 is electrically connected to part of the conductive film 695 with a connector 686. Accordingly, a signal or a potential input from the FPC 672 connected to the substrate 651 side can be supplied to the conductive film 695 formed on the substrate 661 side through the connection portion 687.

As the connector 686, a conductive particle can be used, for example. As the conductive particle, a particle of an organic resin, silica, or the like coated with a metal material can be used. It is preferable to use nickel or gold as the metal material because contact resistance can be reduced. It is also preferable to use a particle coated with layers of two or more kinds of metal materials, such as a particle coated with nickel and further with gold. As the connector 686, a material capable of elastic deformation or plastic deformation is preferably used. As illustrated in FIG. 17, the connector 686 which is the conductive particle has a shape that is vertically crushed in some cases. With the crushed shape, the contact area between the connector 686 and a conductive layer electrically connected to the connector 686 can be increased, thereby reducing contact resistance and suppressing the generation of problems such as disconnection.

The connector 686 is preferably provided so as to be covered with the adhesive layer 641. For example, the connectors 686 are dispersed in the adhesive layer 641 before curing of the adhesive layer 641.

FIG. 17 illustrates an example of the circuit 659 in which the transistor 689 is provided.

In FIG. 17, as a structure example of the transistors 689 and 691, the semiconductor film 653 where a channel is formed is provided between two gates. One gate is formed using the conductive film 654 and the other gate is formed using a conductive film 699 overlapping with the semiconductor film 653 with the insulating film 682 provided therebetween. Such a structure enables the control of threshold voltages of a transistor. In that case, the two gates may be connected to each other and supplied with the same signal to operate the transistor. Such a transistor can have a higher field-effect mobility and thus have a higher on-state current than other transistors. Consequently, a circuit capable of high-speed operation can be obtained. Furthermore, the area occupied by a circuit portion can be reduced. The use of the transistor having a high on-state current can reduce signal delay in wirings and can reduce display unevenness even in a display panel that has an increased number of wirings with an increase in size or resolution.

Note that the transistor included in the circuit 659 and the transistor included in the display portion 662 may have the same structure. A plurality of transistors included in the circuit 659 may have the same structure or different structures. A plurality of transistors included in the display portion 662 may have the same structure or different structures.

A material through which impurities such as water and hydrogen do not easily diffuse is preferably used for at least one of the insulating films 682 and 683 which cover the transistors. That is, the insulating film 682 or the insulating film 683 can function as a barrier film. Such a structure can effectively suppress the diffusion of the impurities into the transistors from the outside, and a highly reliable display panel can be provided.

The insulating film 698 is provided on the substrate 661 side to cover the coloring layer 631 and the light-blocking film 632. The insulating film 698 may have a function as a planarization layer. The insulating film 698 enables the conductive film 695 to have an almost flat surface, resulting in a uniform alignment state of the liquid crystal layer 694.

An example of the method for manufacturing the display panel 688 is described. For example, the conductive film 635, the conductive film 663, and the insulating film 697 are formed in order over a support substrate provided with a separation layer, and the transistor 691, the transistor 692, the light-emitting element 660, and the like are formed. Then, the substrate 651 and the support substrate are bonded with the adhesive layer 642. After that, separation is performed at the interface between the separation layer and each of the insulating film 697 and the conductive film 635, whereby the support substrate and the separation layer are removed. Separately, the coloring layer 631, the light-blocking film 632, the conductive film 695, and the like are formed over the substrate 661 in advance. Then, the liquid crystal is dropped onto the substrate 651 or 661 and the substrates 651 and 661 are bonded with the adhesive layer 641, whereby the display panel 688 can be manufactured.

A material for the separation layer can be selected such that separation at the interface with the insulating film 697 and the conductive film 635 occurs. In particular, it is preferable that a stack of a layer including a high-melting-point metal material, such as tungsten, and a layer including an oxide of the metal material be used as the separation layer, and a stack of a plurality of layers, such as a silicon nitride layer, a silicon oxynitride layer, and a silicon nitride oxide layer be used as the insulating film 697 over the separation layer. The use of the high-melting-point metal material for the separation layer can increase the formation temperature of a layer formed in a later step, which reduces impurity concentration and achieves a highly reliable display panel.

As the conductive film 635, an oxide or a nitride such as a metal oxide, a metal nitride, or an oxide semiconductor with reduced resistance is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive film 635.
<6-3. Components>

The above components will be described below. Note that the description of the structures having functions similar to those described above is omitted.
[Adhesive Layer]

As the adhesive layer, a variety of curable adhesives such as a reactive curable adhesive, a theiniosetting adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. Alternatively, a two-component type resin may be used. Further alternatively, an adhesive sheet or the like may be used.

Furthermore, the resin may include a drying agent. For example, a substance that adsorbs moisture by chemical adsorption, such as an oxide of an alkaline earth metal (e.g., calcium oxide or barium oxide), can be used. Alternatively, a substance that adsorbs moisture by physical adsorption, such as zeolite or silica gel, may be used. The drying agent is preferably included because it can prevent impurities such as moisture from entering the element, thereby improving the reliability of the display panel.

In addition, it is preferable to mix a filler with a high refractive index or light-scattering member into the resin, in which case light extraction efficiency can be enhanced. For example, titanium oxide, barium oxide, zeolite, zirconium, or the like can be used.

[Connection Layer]

As the connection layer, an anisotropic conductive film (ACF), an anisotropic conductive paste (ACP), or the like can be used.

[Coloring Layer]

Examples of the material that can be used for the coloring layers include a metal material, a resin material, and a resin material containing a pigment or dye.

[Light-Blocking Layer]

Examples of the material that can be used for the light-blocking layer include carbon black, titanium black, a metal, a metal oxide, and a composite oxide containing a solid solution of a plurality of metal oxides. The light-blocking layer may be a film containing a resin material or a thin film of an inorganic material such as a metal. Stacked films containing the material of the coloring layer can also be used for the light-blocking layer. For example, a stacked-layer structure of a film containing a material for a coloring layer that transmits light of a certain color and a film containing a material for a coloring layer that transmits light of another color can be employed. The coloring layer and the light-blocking layer are preferably formed using the same material so that the same manufacturing apparatus can be used and the process can be simplified.

The above is the description of the components.

<6-4. Manufacturing Method Example>

A manufacturing method example of a display panel using a flexible substrate is described.

Here, layers including a display element, a circuit, a wiring, an electrode, optical members such as a coloring layer and a light-blocking layer, an insulating layer, and the like, are collectively referred to as an element layer. The element layer includes, for example, a display element, and may additionally include a wiring electrically connected to the display element or an element such as a transistor used in a pixel or a circuit.

In addition, here, a flexible member that supports the element layer at the time when the display element is completed (the manufacturing process is finished) is referred to as a substrate. For example, a substrate includes an extremely thin film with a thickness greater than or equal to 10 nm and less than or equal to 300 μm.

As a method for forming an element layer over a flexible substrate provided with an insulating surface, typically, the following two methods can be employed. One of them is to form an element layer directly on the substrate. The other method is to form an element layer over a support substrate that is different from the substrate and then to separate the element layer from the support substrate to be transferred to the substrate. Although not described in detail here, in addition to the above two methods, there is a method in which an element layer is formed over a substrate that does not have flexibility and the substrate is thinned by polishing or the like to have flexibility.

In the case where a material of the substrate has a resistance to heat applied in the forming process of the element layer, it is preferable that the element layer be formed directly on the substrate, in which case a manufacturing process can be simplified. At this time, the element layer is preferably formed in a state where the substrate is fixed to the support substrate, in which case transfer thereof in an apparatus and between apparatuses can be easy.

In the case of employing the method in which the element layer is formed over the support substrate and then transferred to the substrate, first, a separation layer and an insulating layer are stacked over the support substrate, and then the element layer is formed over the insulating layer. Next, the element layer is separated from the support substrate and then transferred to the substrate. At this time, a material may be selected so that the separation occurs at the interface between the support substrate and the separation layer, at the interface between the separation layer and the insulating layer, or in the separation layer. In this method, a high heat resistant material is preferably used for the support substrate or the separation layer, in which case the upper limit of the temperature applied when the element layer is formed can be increased, and an element layer including a more highly reliable element can be formed.

For example, it is preferable that a stack of a layer containing a high-melting-point metal material, such as tungsten, and a layer containing an oxide of the metal material be used as the separation layer, and a stack of a plurality of layers, such as a silicon oxide layer, a silicon nitride layer, a silicon oxynitride layer, and a silicon nitride oxide layer be used as the insulating layer over the separation layer.

The element layer and the support substrate can be separated by applying mechanical power, by etching the separation layer, by injecting a liquid into the separation interface, or the like. Alternatively, separation may be performed by heating or cooling two layers of the separation interface by utilizing a difference in thermal expansion coefficient.

The separation layer is not necessarily provided in the case where the separation can be performed at the interface between the support substrate and the insulating layer.

For example, glass and an organic resin such as polyimide can be used as the support substrate and the insulating layer, respectively. In that case, a separation trigger may be formed by, for example, locally heating part of the organic resin with laser light or the like, or by physically cutting part of or making a hole through the organic resin with a sharp tool, and separation may be performed at the interface between the glass and the organic resin. As the above-described organic resin, a photosensitive material is preferably used because an opening or the like can be easily formed. The above-described laser light preferably has a wavelength region, for example, from visible light to ultraviolet light. For example, light having a wavelength greater than or equal to 200 nm and less than or equal to 400 nm, preferably greater than or equal to 250 nm and less than or equal to 350 nm can be used. In particular, an excimer laser having a wavelength of 308 nm is preferably used because the productivity is increased. Alternatively, a solid-state UV laser (also referred to as a semiconductor UV laser), such as a UV laser having a wavelength of 355 nm which is the third harmonic of an Nd:YAG laser, may be used.

Alternatively, a heat generation layer may be provided between the support substrate and the insulating layer formed of an organic resin, and separation may be performed at the interface between the heat generation layer and the insulating layer by heating the heat generation layer. For the heat generation layer, a material that generates heat when current flows therethrough, a material that generates heat when it absorbs light, a material that generates heat when applied with a magnetic field, and other various materials can be used. For example, a material for the heat generation layer can be selected from a semiconductor, a metal, and an insulator.

In the above-described methods, the insulating layer formed of an organic resin can be used as a substrate after the separation.

The above is the description of the manufacturing method of a flexible display panel.

At least part of this embodiment can be implemented in appropriate combination with any of the other structures described in this specification.

<<Electronic Device>>

Examples of an electronic device of one embodiment of the present invention will be described. Examples of the electronic device include a television device (also referred to as a television or a television receiver), a monitor of a computer or the like, a camera such as a digital camera or a digital video camera, a digital photo frame, a mobile phone (also referred to as a mobile telephone or a mobile phone device), a portable game console, a portable information terminal, an audio reproducing device, and a large-sized game machine such as a pachinko machine. Specific examples of these electronic devices are described below.

Figure 9A:
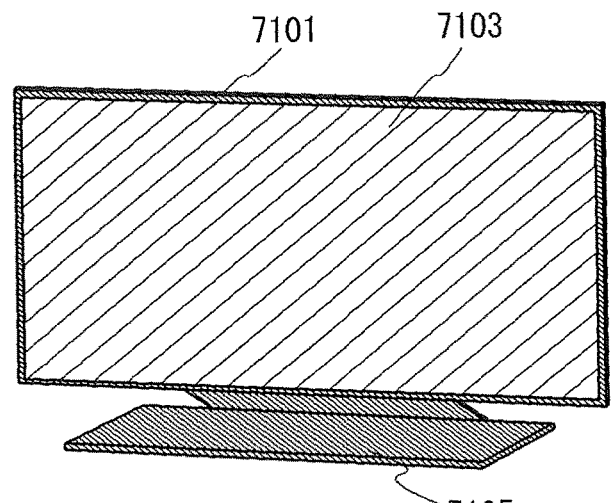
Figure 9A:
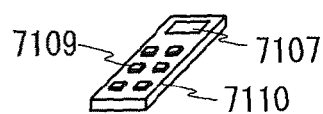
Figure 9A:
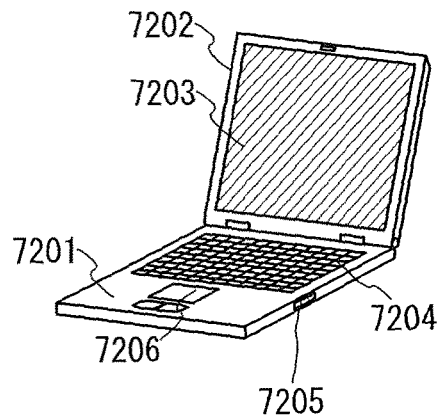
Figure 9A:
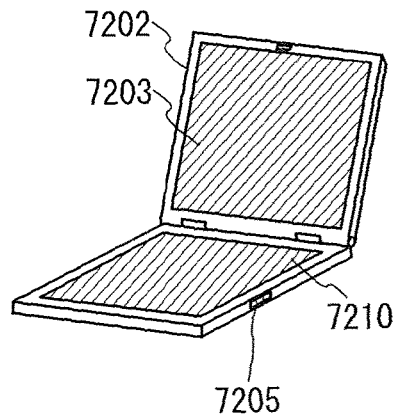

FIG. 9A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the television device is connected to a communication network with or without wires via the modem, one-way (from a sender to a receiver) or two-way (between a sender and a receiver or between receivers) data communication can be performed.

FIG. 9B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203. The computer illustrated in FIG. 9B1 may have a structure illustrated in FIG. 9B2. The computer illustrated in FIG. 9B2 is provided with a second display portion 7210 instead of the keyboard 7204 and the pointing device 7206. The second display portion 7210 is a touch panel, and input can be performed by operation of display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 9C:
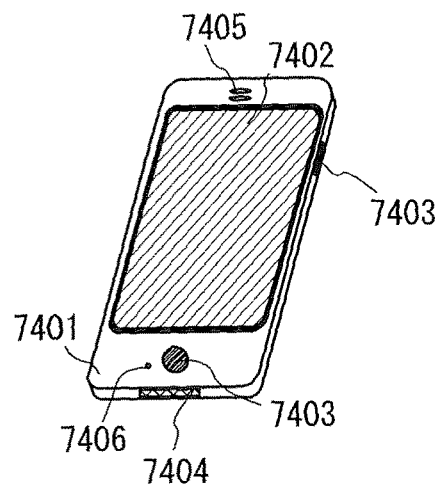
Figure 9D:
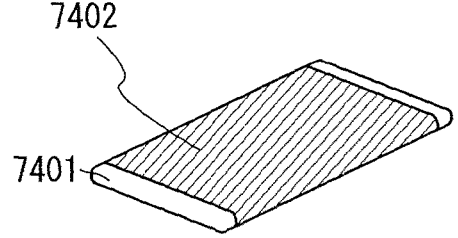

FIGS. 9C and 9D illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal has the display portion 7402 including light-emitting elements arranged in a matrix.

Information can be input to the portable information terminal illustrated in FIGS. 9C and 9D by touching the display portion 7402 with a finger or the like. In that case, operations such as making a call and creating e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be input. In that case, it is preferable to display a keyboard or number buttons on almost the entire screen of the display portion 7402.

When a detection device including a sensor for sensing inclination, such as a gyroscope sensor or an acceleration sensor, is provided inside the portable information terminal, screen display of the display portion 7402 can be automatically changed by determining the orientation of the portable information terminal (whether the portable information terminal is placed horizontally or vertically).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes a light-emitting element of one embodiment of the present invention. The light-emitting element can have high emission efficiency. In addition, the light-emitting element can be driven with low voltage. Thus, the electronic device including the light-emitting element of one embodiment of the present invention can have low power consumption.

Figure 10:
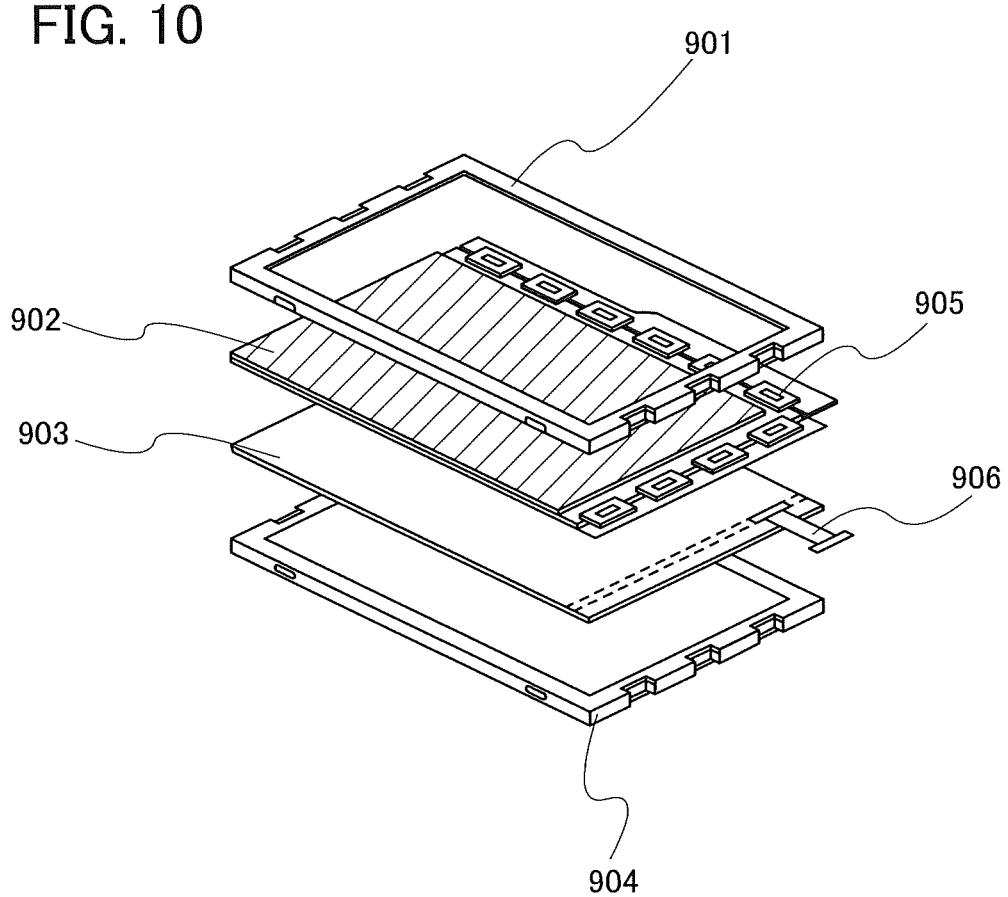
FIG. 10 illustrates a light source device.

FIG. 10 illustrates an example of a liquid crystal display device including the light-emitting element for a backlight. The liquid crystal display device illustrated in FIG. 10 includes a housing 901, a liquid crystal layer 902, a backlight unit 903, and a housing 904. The liquid crystal layer 902 is connected to a driver IC 905. The light-emitting element is used for the backlight unit 903, to which current is supplied through a terminal 906.

As the light-emitting element, a light-emitting element of one embodiment of the present invention is preferably used. By including the light-emitting element, the backlight of the liquid crystal display device can have low power consumption.

Figure 11:
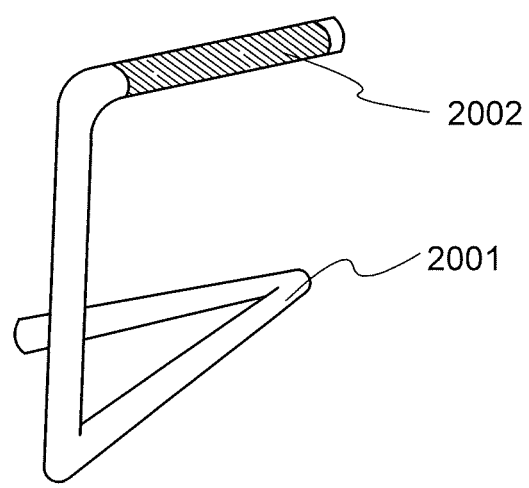
FIG. 11 illustrates a lighting device.

FIG. 11 illustrates an example of a desk lamp of one embodiment of the present invention. The desk lamp illustrated in FIG. 11 includes a housing 2001 and a light source 2002, and a lighting device including a light-emitting element is used as the light source 2002.

Figure 12:
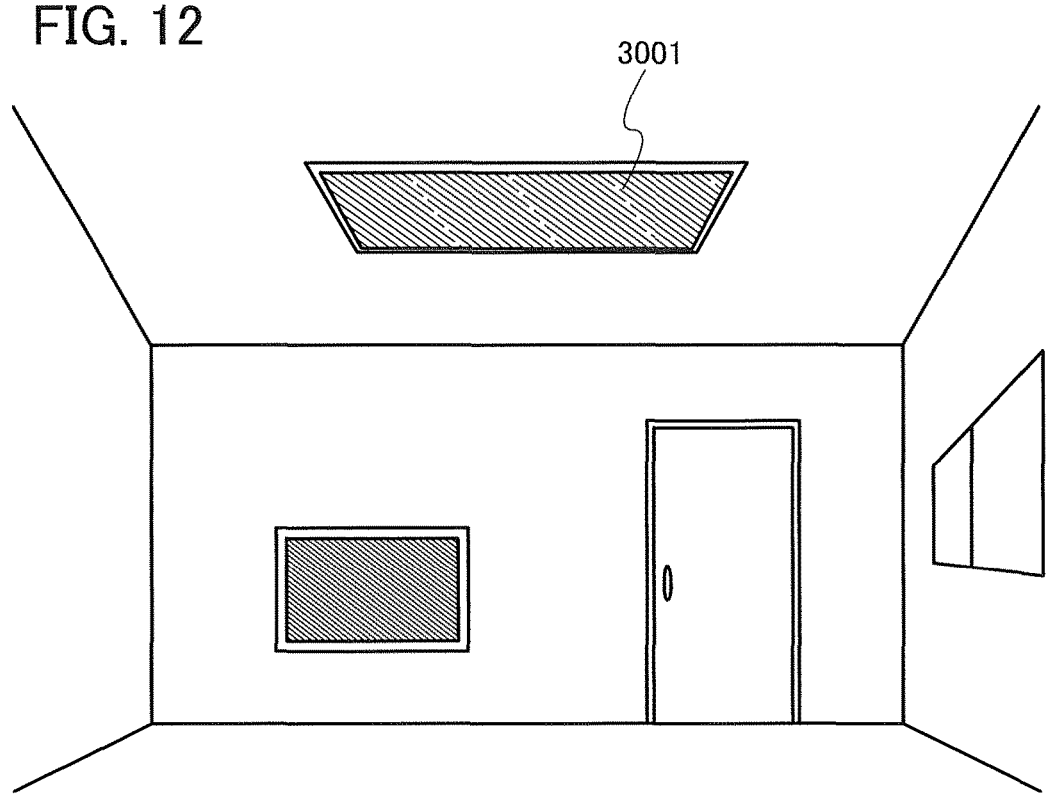
FIG. 12 illustrates a lighting device.

FIG. 12 illustrates an example of an indoor lighting device 3001. The light-emitting element of one embodiment of the present invention is preferably used in the lighting device 3001.

Figure 13:
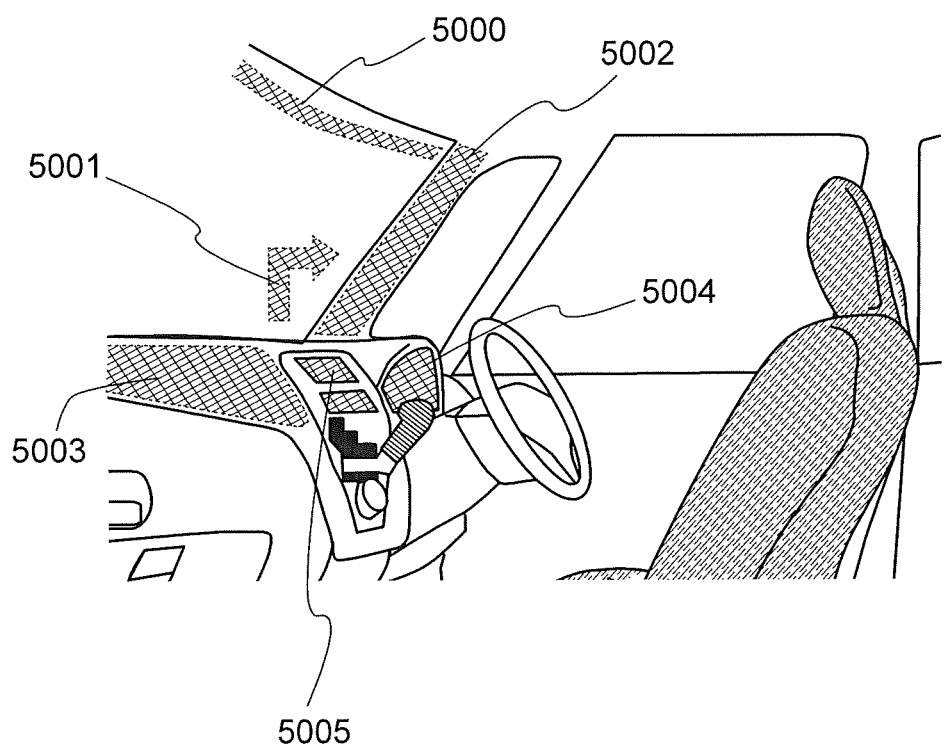
FIG. 13 illustrates car-mounted display devices and lighting devices.

An automobile of one embodiment of the present invention is illustrated in FIG. 13. In the automobile, light-emitting elements are used for a windshield and a dashboard. Display regions 5000 to 5005 are preferably formed by using the light-emitting elements of one embodiment of the present invention. This suppresses the power consumption of the display regions 5000 to 5005, showing suitability for use in an automobile.

The display regions 5000 and 5001 are display devices which are provided in the automobile windshield and which include the light-emitting elements. When a first electrode and a second electrode are formed of electrodes having light-transmitting properties in these light-emitting elements, what is called a see-through display device, through which the opposite side can be seen, can be obtained. Such see-through display devices can be provided even in the windshield of the automobile, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and which includes the light-emitting element. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

Figure 14A:
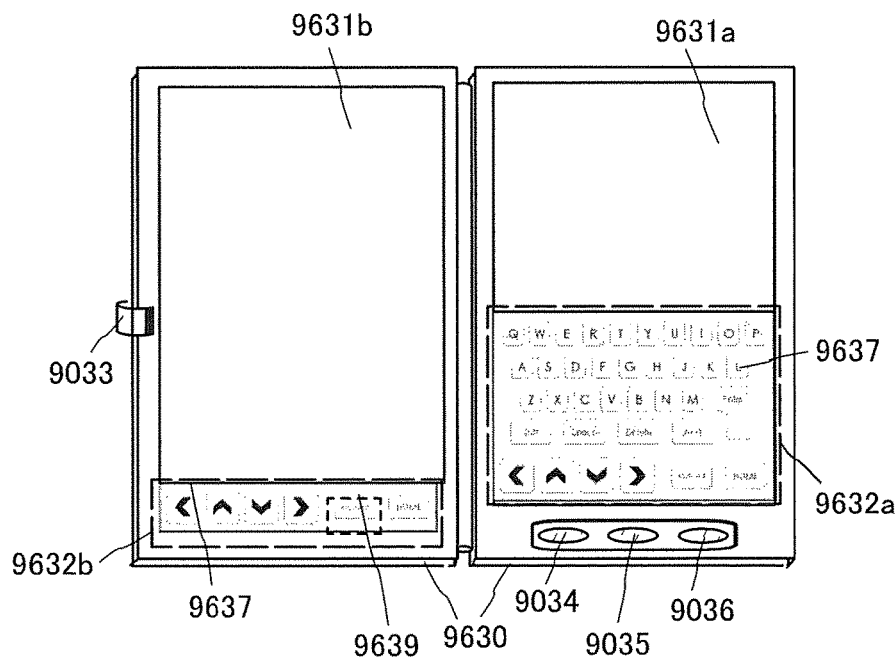
FIGS. 14A to 14C illustrate an electronic device.
Figure 14B:
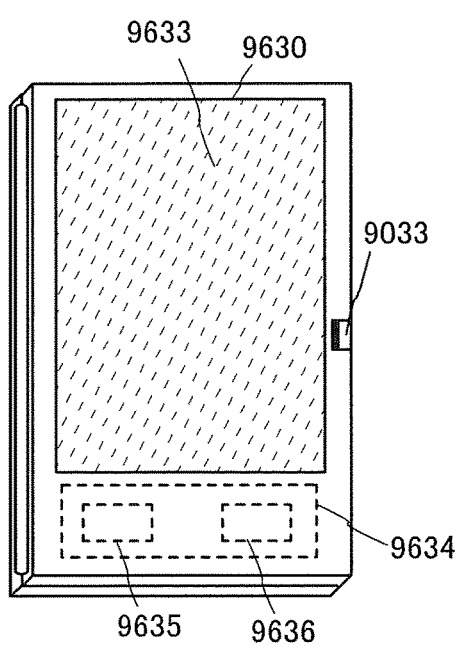

FIGS. 14A and 14B illustrate an example of a foldable tablet terminal. In FIG. 14A, the tablet terminal is opened, and includes a housing 9630, a display portion 9631a, a display portion 9631b, a switch 9034 for switching display modes, a power switch 9035, a switch 9036 for switching to power-saving mode, a fastener 9033, and an operation switch 9038. Note that in the tablet terminal, one or both of the display portion 9631a and the display portion 9631b are formed using a light-emitting device which includes the light-emitting element of one embodiment of the present invention.

Part of the display portion 9631a can be a touch panel region 9632a and data can be input when a displayed operation key 9637 is touched. Although a structure in which a half region in the display portion 9631a has only a display function and the other half region has a touch panel function is illustrated as an example, the structure of the display portion 9631a is not limited thereto. The whole region in the display portion 9631a may have a touch panel function. For example, the display portion 9631a can display keyboard buttons in the whole region to be a touch panel, and the display portion 9631b can be used as a display screen.

Like the display portion 9631a, part of the display portion 9631b can be a touch panel region 9632b. When a switching button 9639 for showing/hiding a keyboard on the touch panel is touched with a finger, a stylus, or the like, the keyboard can be displayed on the display portion 9631b.

Touch input can be performed in the touch panel region 9632a and the touch panel region 9632b at the same time.

The switch 9034 for switching display modes can switch the display between portrait mode, landscape mode, and the like, and between monochrome display and color display, for example. The switch 9036 for switching to power-saving mode can control display luminance to be optimal in accordance with the amount of external light in use of the tablet terminal which is sensed by an optical sensor incorporated in the tablet terminal. Another sensing device including a sensor for sensing inclination, such as a gyroscope sensor or an acceleration sensor, may be incorporated in the tablet terminal, in addition to the optical sensor.

Note that FIG. 14A illustrates an example in which the display portion 9631a and the display portion 9631b have the same display area; however, without limitation thereon, one of the display portions may be different from the other display portion in size and display quality. For example, one display panel may be capable of higher-definition display than the other display panel.

FIG. 14B illustrates the tablet terminal which is folded. The tablet terminal in this embodiment includes the housing 9630, a solar cell 9633, a charge and discharge control circuit 9634, a battery 9635, and a DCDC converter 9636. Note that FIG. 14B illustrates an example in which the charge and discharge control circuit 9634 includes the battery 9635 and the DCDC converter 9636.

Since the tablet terminal can be folded, the housing 9630 can be closed when the tablet terminal is not used. As a result, the display portion 9631a and the display portion 9631b can be protected; thus, a tablet terminal which has excellent durability and excellent reliability in terms of long-term use can be provided.

In addition, the tablet terminal illustrated in FIGS. 14A and 14B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case the battery 9635 can be charged efficiently.

Figure 14C:
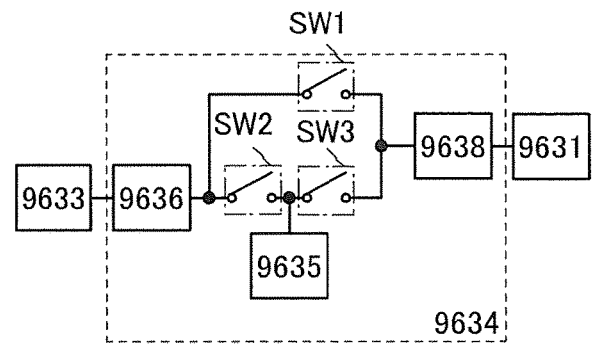

The structure and the operation of the charge and discharge control circuit 9634 illustrated in FIG. 14B are described with reference to a block diagram in FIG. 14C. FIG. 14C illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 illustrated in FIG. 14B.

First, an example of the operation in the case where power is generated by the solar cell 9633 using external light is described. The voltage of power generated by the solar cell is raised or lowered by the DCDC converter 9636 so that the power has a voltage for charging the battery 9635. Then, when power charged by the solar cell 9633 is used for the operation of the display portion 9631, the switch SW1 is turned on and the voltage of the power is raised or lowered by the converter 9638 so as to be voltage needed for the display portion 9631. When display on the display portion 9631 is not performed, the switch SW1 is turned off and the switch SW2 is turned on so that charge of the battery 9635 may be performed.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 14A to 14C as long as the display portion 9631 is included.

Figure 15A:
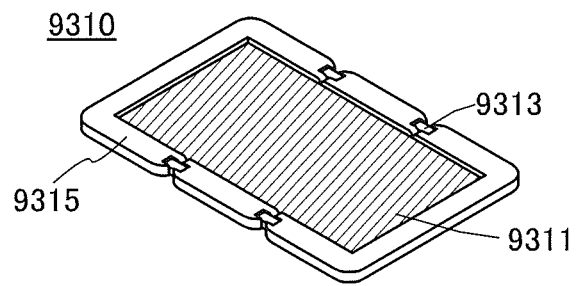
FIGS. 15A to 15C illustrate an electronic device.
Figure 15B:
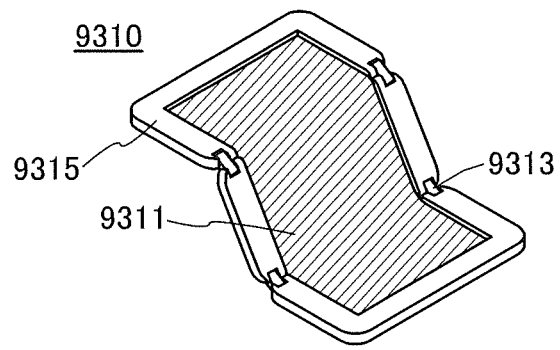
Figure 15C:
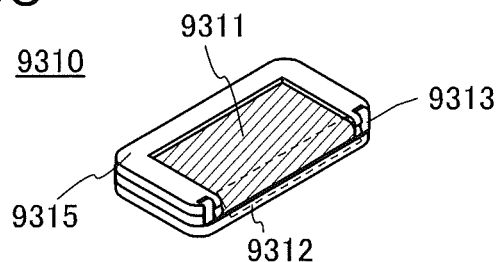

FIGS. 15A to 15C illustrate a foldable portable information terminal 9310. FIG. 15A illustrates the portable information terminal 9310 which is opened. FIG. 15B illustrates the portable information terminal 9310 which is being opened or being folded. FIG. 15C illustrates the portable information terminal 9310 which is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 in the display panel 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

EXAMPLE 1

In this example, Light-emitting Elements 1 to 3 of one embodiment of the present invention, which are described in the embodiment, are described. Structural formulae of organic compounds used in Light-emitting Elements 1 to 3 are shown below.

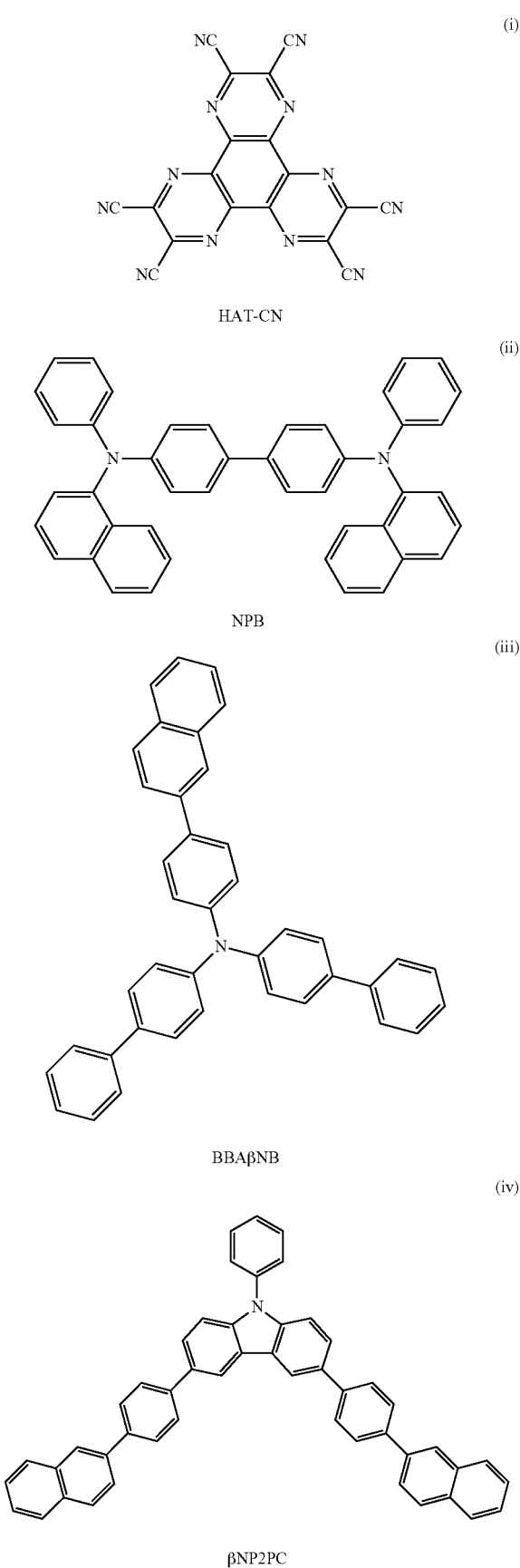 [SMILES: N#Cc1nc2c3nc(C#N)c(C#N)nc3c3nc(C#N)c(C#N)nc3c2nc1C#N ; c1ccc(N(c2ccc(-c3ccc(N(c4ccccc4)c4cccc5ccccc45)cc3)cc2)c2cccc3ccccc23)cc1 ; "NPB" ; c1ccc(-c2ccc(N(c3ccc(-c4ccccc4)cc3)c3ccc(-c4ccc5ccccc5c4)cc3)cc2)cc1 ; c1ccc(-n2c3ccc(-c4ccc(-c5ccc6ccccc6c5)cc4)cc3c3cc(-c4ccc(-c5ccc6ccccc6c5)cc4)ccc32)cc1]

(v)
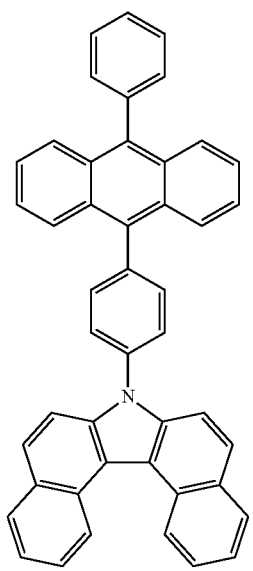
cgDBCzPA
(vi)
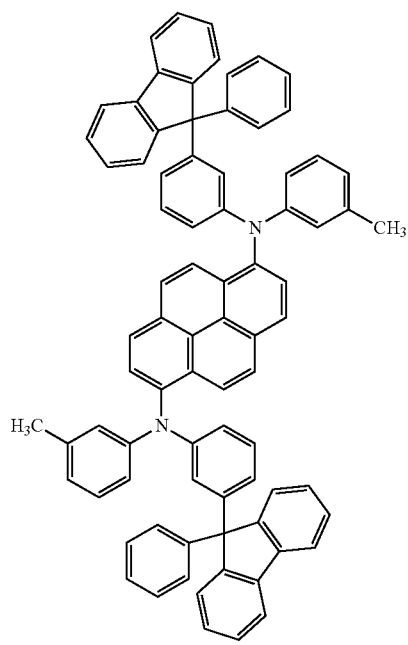
1,6mMemFLPAPm
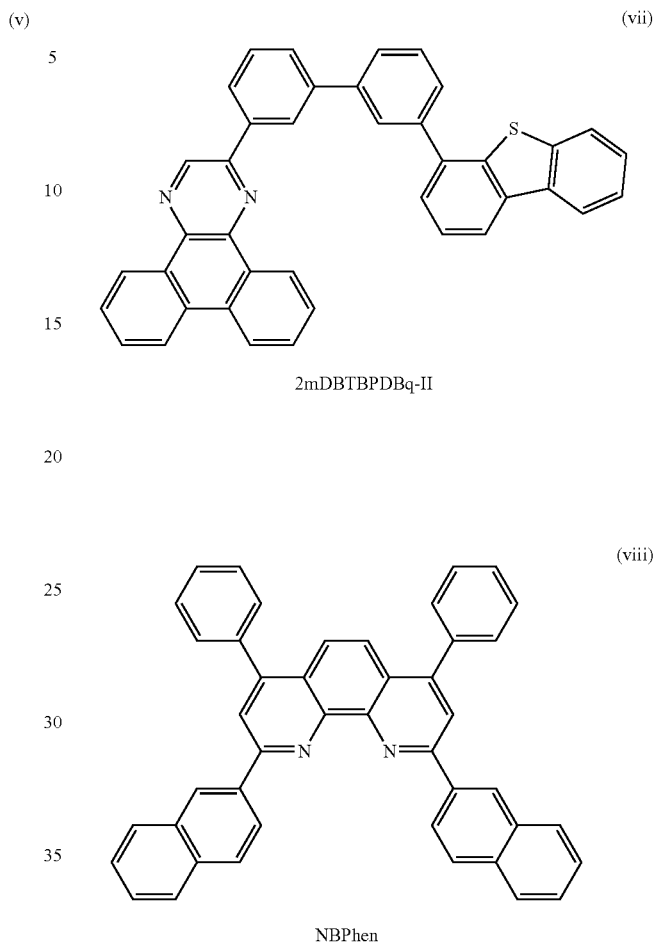
(vii) 2mDBTBPDBq-II
(viii) NBPhen
(ix)
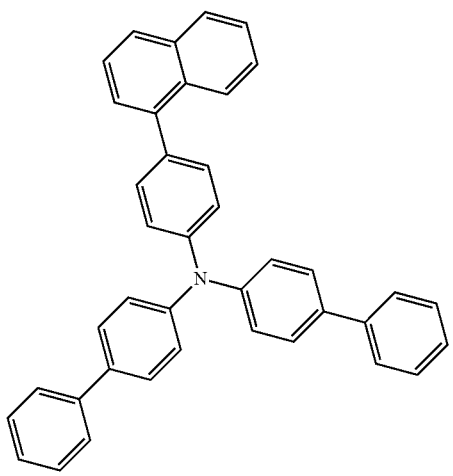
BBAαNB -continued

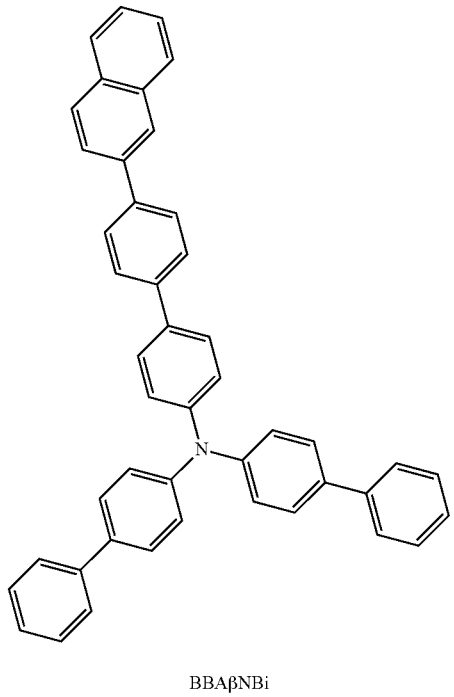

BBAβNBi (Fabrication Method of Light-Emitting Element 1)

First, a film of indium tin oxide containing silicon oxide (ITSO) was formed over a glass substrate by a sputtering method, so that the first electrode 101 was formed. The thickness of the first electrode 101 was 70 nm and the electrode area was 4 mm$^2$ (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately 10$^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 2,3,6,7,10,11-hexacyano-1,4,5,8,9,12-hexaazatriphenylene (abbreviation: HAT-CN) represented by Structural Formula (i) was deposited by evaporation to a thickness of 5 nm by an evaporation method using resistance heating, so that the hole-injection layer 111 was formed.

Next, a film of 4,4'-bis[N-(1-naphthyl)-N-phenylamino] biphenyl (abbreviation: NPB) represented by Structural Formula (ii) was formed by evaporation to a thickness of 10 nm on the hole-injection layer 111 to form the first hole-transport layer 112-1; a film of 4-(2-naphthyl)-4',4''-diphenyltriphenylamine (abbreviation: BBAβNB) represented by Structural Formula (iii) was formed by evaporation to a thickness of 10 nm on the first hole-transport layer 112-1 to form the second hole-transport layer 112-2; and a film of 3,6-bis[4-(2-naphthyl)phenyl]-9-phenyl-9H-carbazole (abbreviation: βNP2PC) represented by Structural Formula (iv) was formed by evaporation to a thickness of 10 nm on the second hole-transport layer 112-2 to form the third hole-transport layer 112-3.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (v) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (vi) at a weight ratio of 1:0.03 (=cgDBCzPA: 1,6mMemFLPAPrn) to a thickness of 25 nm.

Then, over the light-emitting layer 113, a film of 2-[3'-(dibenzothiophen-4-yl)biphenyl-3-yl]dibenzo[f,h]quinoxaline (abbreviation: 2mDBTBPDBq-II), which is represented by Structural Formula (vii), was formed by evaporation to a thickness of 10 nm, and a film of 2,9-bis(naphthalen-2-yl)-4,7-diphenyl-1,10-phenanthroline (abbreviation: NBPhen) represented by Structural Formula (viii) was formed by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, Light-emitting Element 1 of this example was fabricated.

(Fabrication Method of Light-Emitting Element 2)

Light-emitting Element 2 was fabricated in a manner similar to that of Light-emitting Element 1 except that 4-(1-naphthyl)-4',4''-diphenyltriphenylamine (abbreviation: BBAαNB) represented by Structural Formula (ix) was used as the material of the second hole-transport layer 112-2 instead of BBAβNB in Light-emitting Element 1.

(Fabrication Method of Light-Emitting Element 3)

Light-emitting Element 3 was fabricated in a manner similar to that of Light-emitting Element 1 except that 4-[4-(2-naphthyl)phenyl]-4',4''-diphenyltriphenylamine (abbreviation: BBAβNBi) represented by Structural Formula (x) was used as the material of the second hole-transport layer 112-2 instead of BBAβNB in Light-emitting Element 1.

The element structures of Light-emitting Elements 1 to 3 are shown in the following table.

TABLE 1

| | Hole-injection layer | Hole-transport layer | | | Light-emitting layer | Electron-transport layer | | Electron-injection layer |
|---|---|---|---|---|---|---|---|---|
| | | 1 | 2 | 3 | | | | |
| | 5 nm | 10 nm | 10 nm | 10 nm | 25 nm | 10 nm | 15 nm | 1 nm |
| Element 1 | HAT-CN | NPB | BBAβNB | βNP2PC | cgDBCzPA:1,6mMemFLPAPrn (1:0.03) | 2mDBTBPDBq-II | NBPhen | LiF |
| Element 2 | | | BBAαNB | | | | | |
| Element 3 | | | BBAβNBi | | | | | |

Light-emitting Elements 1 to 3 were each sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics and reliability of Light-emitting Elements 1 to 3 were measured. Note that the measurement was carried out at room temperature (in an atmosphere kept at 25° C.).

Figure 18:
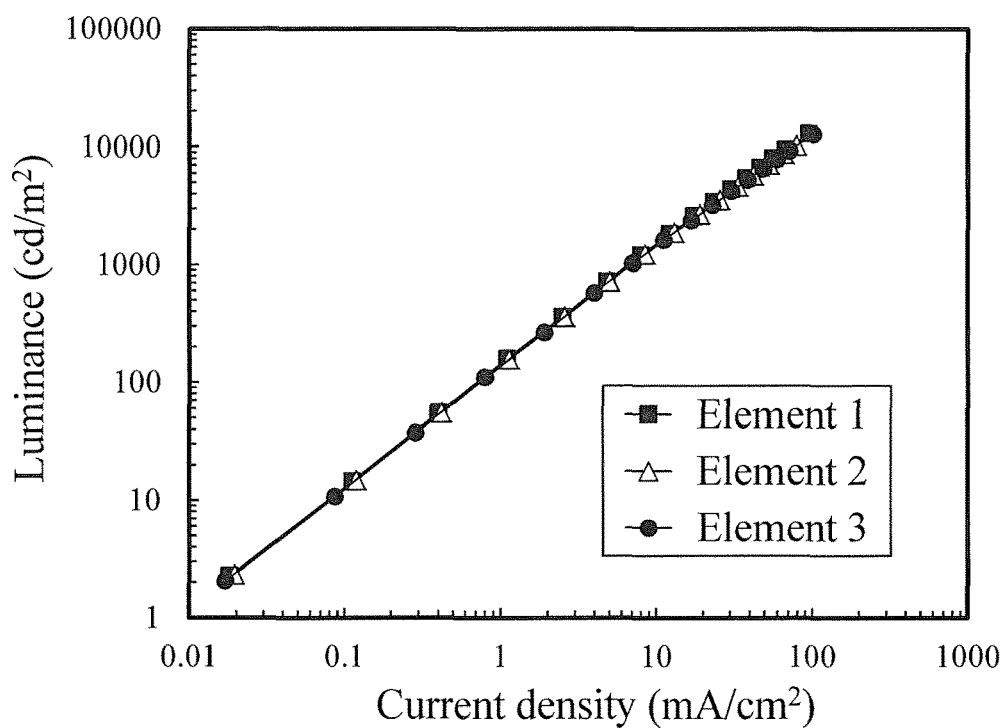
FIG. 18 shows the luminance-current density characteristics of Light-emitting Elements 1 to 3.
Figure 19:
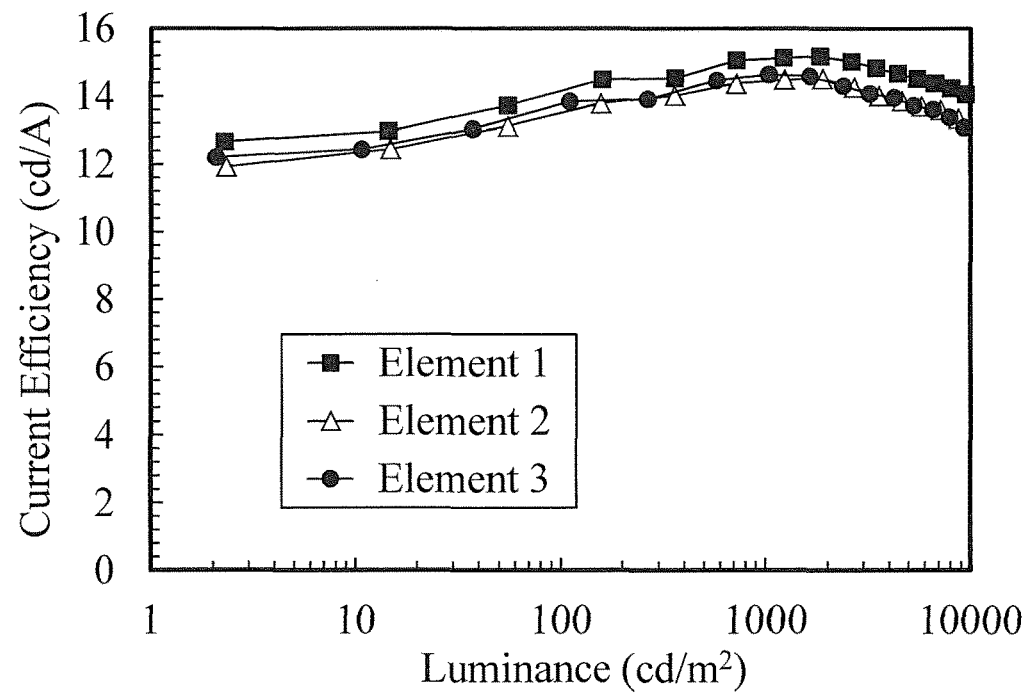
FIG. 19 shows the current efficiency-luminance characteristics of Light-emitting Elements 1 to 3.
Figure 20:
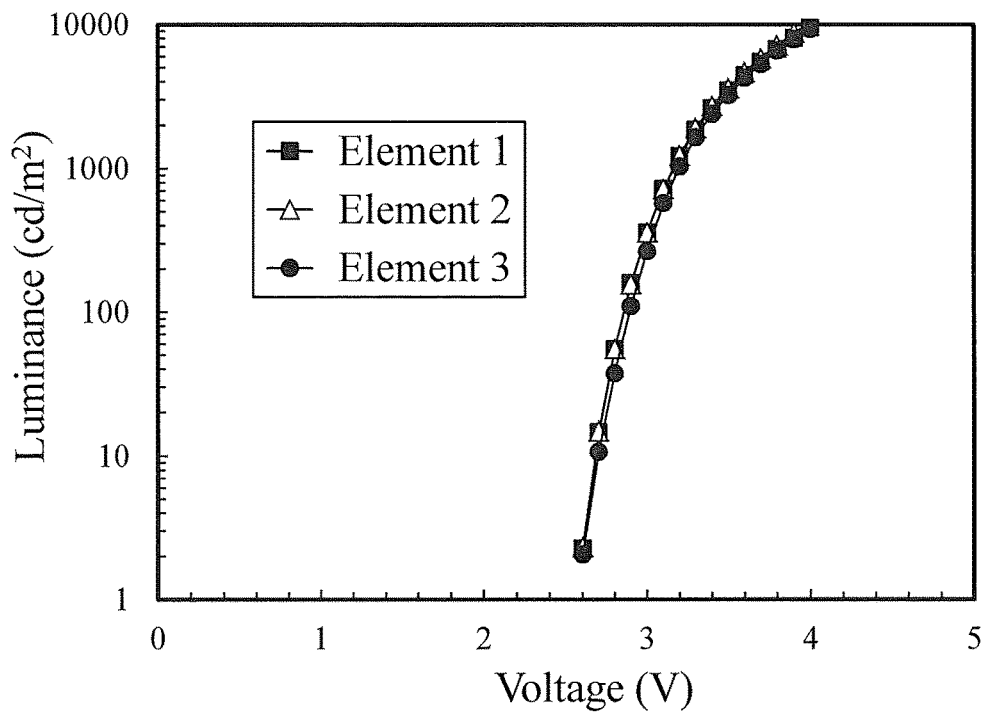
FIG. 20 shows the luminance-voltage characteristics of Light-emitting Elements 1 to 3.
Figure 21:
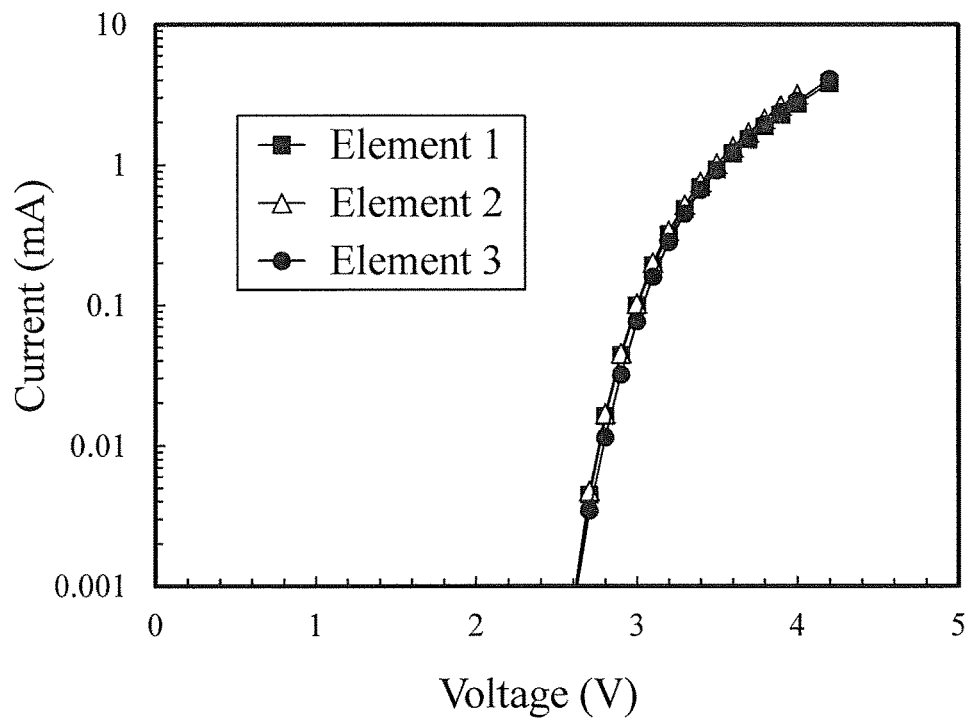
FIG. 21 shows the current-voltage characteristics of Light-emitting Elements 1 to 3.
Figure 22:
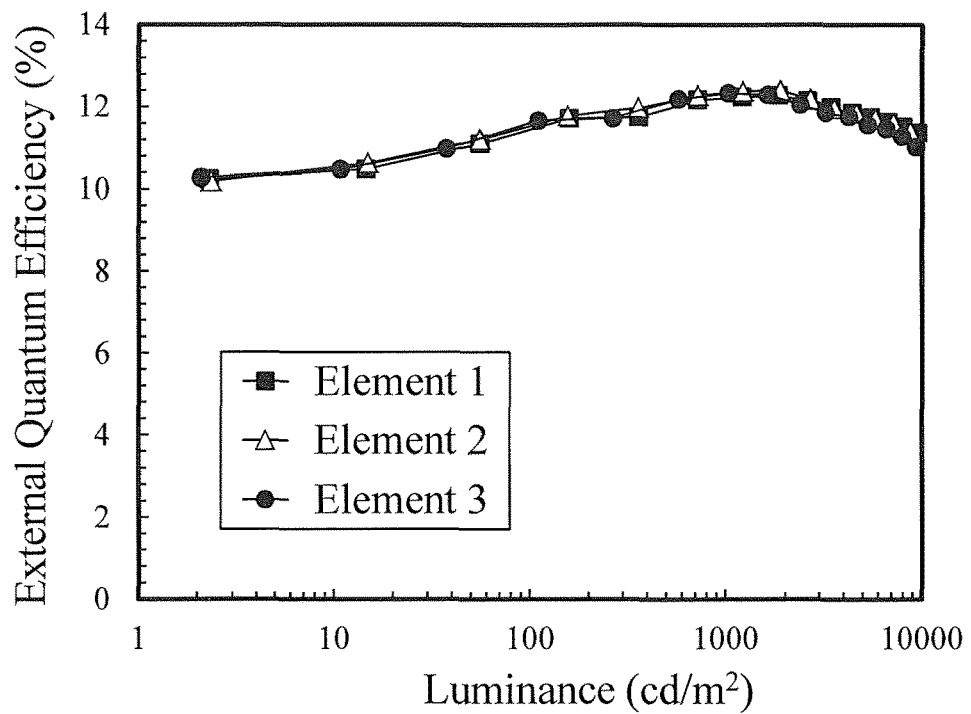
FIG. 22 shows the external quantum efficiency-luminance characteristics of Light-emitting Elements 1 to 3.
Figure 23:
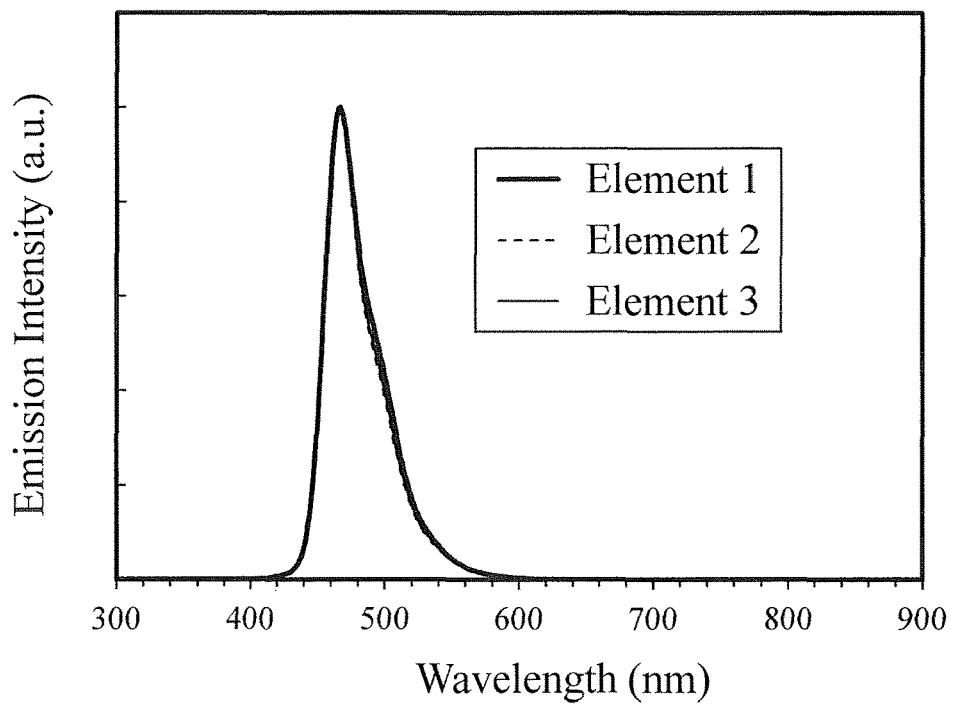
FIG. 23 shows the emission spectra of Light-emitting Elements 1 to 3.

FIG. 18 shows the luminance-current density characteristics of Light-emitting Elements 1 to 3, FIG. 19 shows the current efficiency-luminance characteristics thereof, FIG. 20 shows the luminance-voltage characteristics thereof, FIG. 21 shows the current-voltage characteristics thereof, FIG. 22 shows the external quantum efficiency-luminance characteristics thereof, and FIG. 23 shows the emission spectra thereof. Table 2 shows the main characteristics of Light-emitting Elements 1 to 3 at a luminance of about 1000 cd/m².

TABLE 2

|  | Voltage (V) | Current (mA) | Current (mA/cm²) | chromaticity x | chromaticity y | Current Efficiency (cd/A) | External Quantum Efficiency (%) |
|---|---|---|---|---|---|---|---|
| Element 1 | 3.2 | 0.32 | 8.0 | 0.14 | 0.18 | 15.1 | 12.2 |
| Element 2 | 3.2 | 0.34 | 8.5 | 0.14 | 0.16 | 14.5 | 12.4 |
| Element 3 | 3.2 | 0.28 | 7.1 | 0.14 | 0.17 | 14.6 | 12.3 |

From FIG. 18 to FIG. 23 and Table 2, it was found that Light-emitting Elements 1 to 3 were blue light-emitting elements with favorable characteristics.

Figure 24:
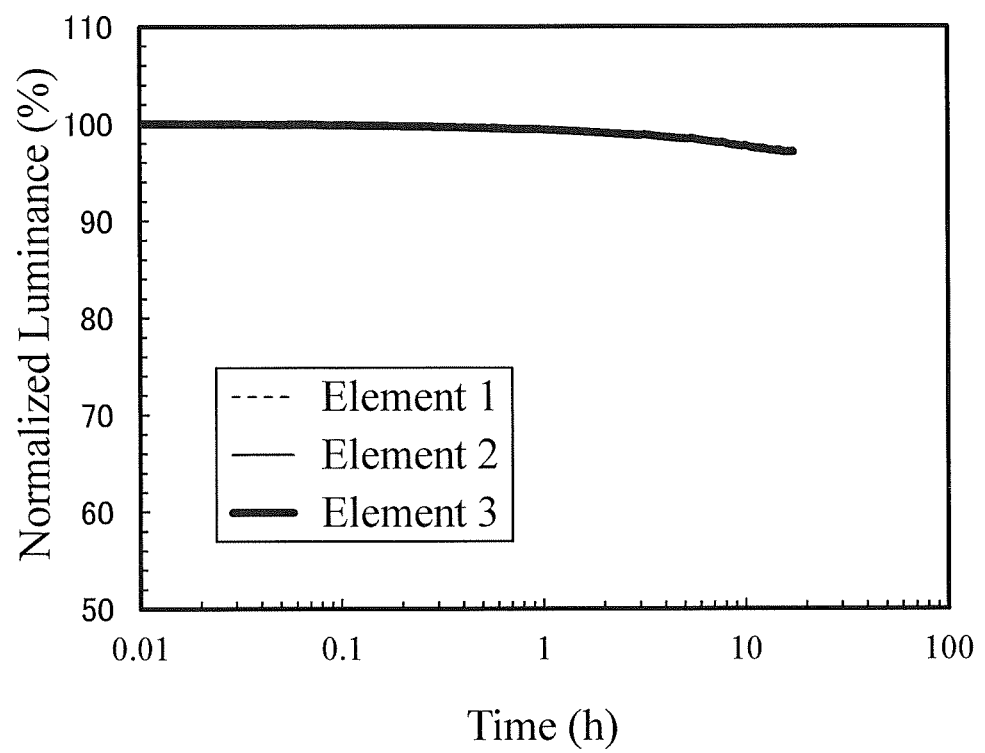
FIG. 24 shows the time dependence of normalized luminance of Light-emitting Elements 1 to 3.

FIG. 24 shows driving time-dependent change in luminance under the conditions where the current value was set to 2 mA and the current density was constant. As shown in FIG. 24, Light-emitting Elements 1 to 3 of one embodiment of the present invention were found to be long-lifetime light-emitting elements with a small reduction in luminance over driving time.

In Light-emitting Elements 1 to 3, a decrease in luminance in the high-luminance region was found to be small. In other words, the light-emitting elements in this example have a structure that allows reducing of a roll-off of the efficiency at a high-luminance side and accordingly allows emitting of high-luminance light while maintaining a high efficiency.

The tables below show the HOMO levels of the first to third hole-transport materials, the host materials, and the light-emitting materials of the light-emitting elements in this example. Note that the HOMO level and the LUMO level were obtained through a cyclic voltammetry (CV) measurement. A calculation method is shown below.

An electrochemical analyzer (ALS model 600A or 600C, manufactured by BAS Inc.) was used as a measurement apparatus. As for a solution used in the CV measurement, dehydrated dimethylformamide (DMF) (manufactured by Aldrich, 99.8%, catalog number: 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was set to 0.1 V/sec, and an oxidation potential Ea [V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be −4.94 [eV], and thus, the HOMO level and the LUMO level can be obtained from the following formula: HOMO level [eV]=−4.94−Ea and LUMO level [eV]=−4.94−Ec.

TABLE 3

| | Light-emitting Element 1 | | | | | | |
|---|---|---|---|---|---|---|---|
| | Hole-transport layer | | | Light-emitting layer | | Electron-transport layer | |
| material | first NPB | second BBAβNB | third βNP2PC | host cgDBCzPA | Light-emitting 1,6mMemFLPAPrn | first 2mDBTBPDBq-II | second NBPhen |
| HOMO level (eV) | −5.38 | −5.47 | −5.79 | −5.69 | −5.40 | — | — |
| LUMO level (eV) | — | — | — | −2.74 | — | −2.94 | −2.83 |

TABLE 4

| | Light-emitting Element 2 | | | | | | |
|---|---|---|---|---|---|---|---|
| | Hole-transport layer | | | Light-emitting layer | | Electron-transport layer | |
| material | first NPB | second BBAαNB | third βNP2PC | host cgDBCzPA | light-emitting 1,6mMemFLPAPrn | first 2mDBTBPDBq-II | second NBPhen |
| HOMO level (eV) | −5.38 | −5.49 | −5.79 | −5.69 | −5.40 | — | — |
| LUMO level (eV) | — | — | — | −2.74 | — | −2.94 | −2.83 |

TABLE 5

| | Light-emitting Element 3 | | | | | | |
|---|---|---|---|---|---|---|---|
| | Hole-transport layer | | | Light-emitting layer | | Electron-transport layer | |
| material | first NPB | second BBAβNB | third βNP2PC | host cgDBCzPA | light-emitting 1,6mMemFLPAPrn | first 2mDBTBPDBq-II | second NBPhen |
| HOMO level (eV) | −5.38 | −5.47 | −5.79 | −5.69 | −5.40 | — | — |
| LUMO level (eV) | — | — | — | −2.74 | — | −2.94 | −2.83 |

As shown in the above tables, as for the materials used in Light-emitting Elements 1 to 3, the HOMO level of the second hole-transport material is deeper than the HOMO level of the first hole-transport material, the HOMO level of the host material is deeper than the HOMO level of the second hole-transport material, and the HOMO level of the third hole-transport material is deeper than the HOMO level of the host material. Furthermore, the HOMO level of the light-emitting material is shallower than the HOMO level of the host material.

The HOMO level of NPB, which is the first hole-transport material, is as shallow as −5.38 eV and can easily cause charge separation by interacting with the LUMO level (−4.41 eV) of HAT-CN.

Here, the HOMO level of cgDBCzPA, which is the host material, is −5.69 eV and its difference from the HOMO level of NPB is 0.31 eV. On the other hand, the HOMO level of 1,6mMemFLPAPrn, which is the light-emitting material, is −5.40 eV and its difference from the HOMO level of NPB is 0.02 eV. Since the difference in HOMO level between the light-emitting material and the first hole-transport material is small, holes are probably injected to the light-emitting material easily when the light-emitting element has a structure in which the first hole-transport layer 112-1 is in contact with the light-emitting layer 113. When the holes are directly injected to the light-emitting material, the holes are trapped at the interface between the first hole-transport layer 112-1 and the light-emitting layer by the light-emitting material, whereby the light-emitting region might be localized to promote deterioration. Furthermore, holes of the hole-transport material of the first hole-transport layer 112-1 are less likely to enter the host material of the light-emitting layer. Therefore, holes and electrons are accumulated in the hole-transport material and the host material, respectively. Accordingly, an exciplex with lower energy than the light-emitting material might be formed between the hole-transport material and the host material, which tends to cause disadvantages such as reduction in emission efficiency.

In Light-emitting Elements 1 to 3, the second hole-transport material whose HOMO level is shallower than the HOMO level of the host material but deeper than the HOMO level of the first hole-transport material is used for the second hole-transport layer 112-2, whereby holes are first injected from the first hole-transport layer 112-1 to the second hole-transport layer 112-2. The HOMO levels of the second hole-transport materials, BBAβNB (Light-emitting Element 1), BBAαNB (Light-emitting Element 2), and BBAβNBi (Light-emitting Element 3) are −5.47 eV, −5.49 eV, and −5.47 eV, respectively and their differences from the HOMO level of the first hole-transport material, NPB, are as small as 0.09 eV, 0.11 eV, and 0.09 eV, respectively. Accordingly, holes are smoothly injected from the first hole-transport layer 112-1 to the second hole-transport layer 112-2.

In the case where holes are injected from the second hole-transport layer 112-2 to the light-emitting layer 113, barriers of approximately 0.22 eV, 0.20 eV, and 0.22 eV exist between the respective second hole-transport materials and the host material. With such a difference, holes are usually injected without problems. Meanwhile, the HOMO level of the light-emitting material included in the light-emitting layer 113 is −5.40 eV, and thus a barrier to hole injection from the second hole-transport material to the light-emitting material does not exist. Therefore, holes are preferentially injected to the light-emitting material than to the host material eventually. As described above, direct injection of holes to the light-emitting material is likely to cause disadvantages such as acceleration of deterioration and reduction in emission efficiency.

Thus, in Light-emitting Elements 1 to 3 of one embodiment of the present invention, the third hole-transport layer 112-3 was further provided between the second hole-transport layer 112-2 and the light-emitting layer 113. The HOMO level of βNP2PC, which is the third hole-transport material included in the third hole-transport layer 112-3, is −5.79 eV and deeper than the HOMO level of the host material. Therefore, holes are injected from the second hole-transport material to the third hole-transport material without problems. In addition, holes are preferentially injected to the host material because there is no barrier to hole injection to the host material and also because of the mixing ratio between the host material and the light-emitting material. Furthermore, the difference in HOMO level between the second hole-transport material and the third hole-transport material is 0.30 eV to 0.32 eV (less than or equal to 0.3 eV with one significant figure), and thus, holes are injected from the second hole-transport material to the third hole-transport material without problems.

Although the holes injected to the host material are partly trapped in the light-emitting material, they can be moved toward the second electrode while being trapped moderately, and the host material is an anthracene compound, which also has an electron-transport property; accordingly, the driving voltage does not increase. In addition, the light-emitting region extends over the light-emitting layer 113 without being localized, and deterioration is not promoted.

Moreover, the light-emitting elements in this example each include cgDBCzPA as the host material, 2mDBTBP-DBq-II as the first electron-transport material, and NBPhen as the second electron-transport material, the LUMO levels of which are estimated to −2.74 eV, −2.94 eV, and −2.83 eV, respectively. With this structure, the light-emitting element is not prone to have excessive electrons and can have a longer lifetime and a higher external quantum efficiency.

From the above, Light-emitting Elements 1 to 3 of this example were found to have highly favorable characteristics, i.e., a long lifetime, a high emission efficiency, and only a slight decrease in efficiency at a high-luminance side.

EXAMPLE 2

In this example, Light-emitting Element 4 of one embodiment of the present invention, which is described in the embodiment, is described. Structural formulae of organic compounds used in Light-emitting Element 4 are shown below.

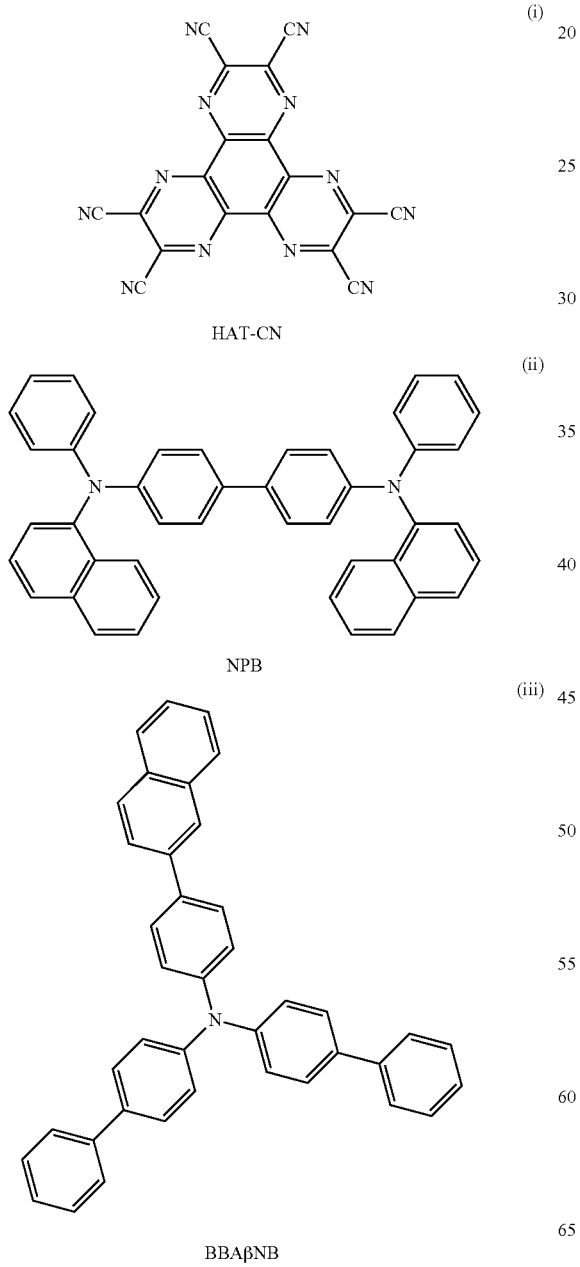

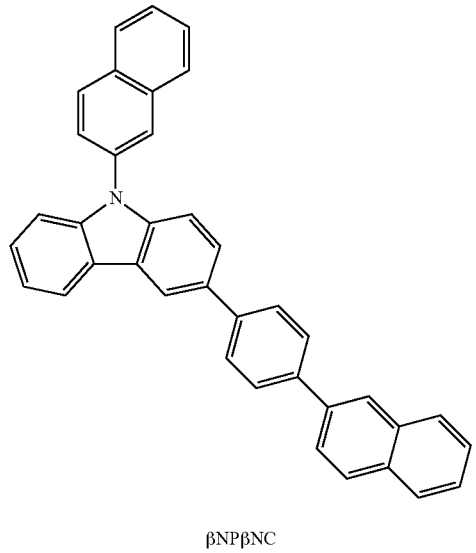

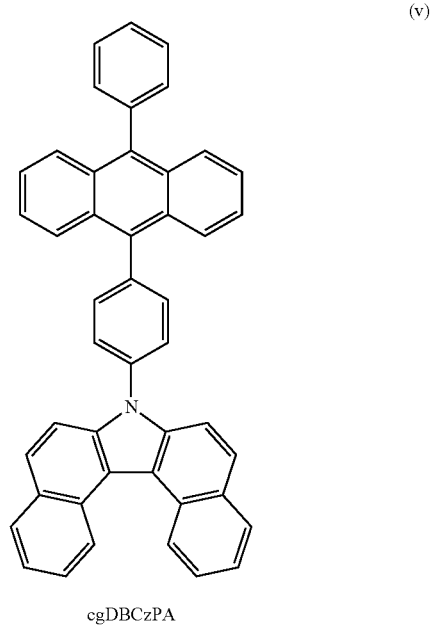

(vi)

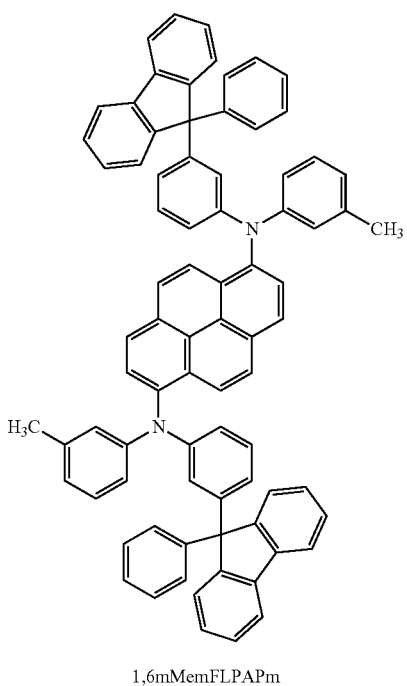

1,6mMemFLPAPrn (vii)

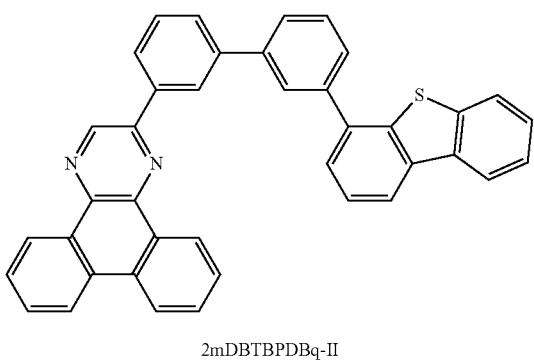

2mDBTBPDBq-II (viii)

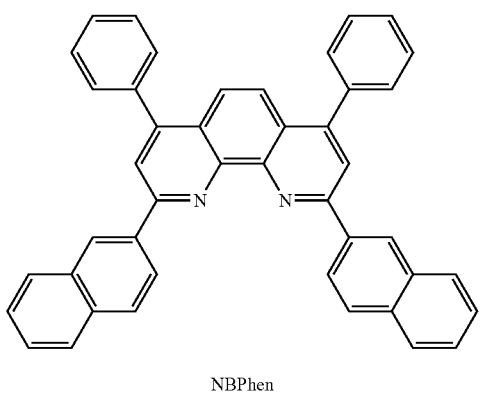

NBPhen (Fabrication Method of Light-Emitting Element 4)

First, a film of indium tin oxide containing silicon oxide (ITSO) was formed over a glass substrate by a sputtering method, so that the first electrode 101 was formed. The thickness of the first electrode 101 was 70 nm and the electrode area was 4 mm² (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 2,3,6,7,10,11-hexacyano-1,4,5,8,9,12-hexaazatriphenylene (abbreviation: HAT-CN) represented by Structural Formula (i) was deposited by evaporation to a thickness of 5 nm by an evaporation method using resistance heating, so that the hole-injection layer 111 was formed.

Next, a film of 4,4'-bis[N-(1-naphthyl)-N-phenylamino]biphenyl (abbreviation: NPB) represented by Structural Formula (ii) was formed by evaporation to a thickness of 10 nm on the hole-injection layer 111 to form the first hole-transport layer 112-1; a film of 4-(2-naphthyl)-4',4"-diphenyltriphenylamine (abbreviation: BBAβNB) represented by Structural Formula (iii) was formed by evaporation to a thickness of 10 nm on the first hole-transport layer 112-1 to form the second hole-transport layer 112-2; and a film of 3-[4-(2-naphthyl)phenyl]-9-(2-naphthyl)-9H-carbazole (abbreviation: βNPβNC) represented by Structural Formula (xi) was formed by evaporation to a thickness of 10 nm on the second hole-transport layer 112-2 to form the third hole-transport layer 112-3.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (v) and N,N'-bis(3-methylphenyl)-N,N'-bis[3-(9-phenyl-9H-fluoren-9-yl)phenyl]pyrene-1,6-diamine (abbreviation: 1,6mMemFLPAPrn) represented by Structural Formula (vi) at a weight ratio of 1:0.03 (=cgDBCzPA: 1,6mMemFLPAPrn) to a thickness of 25 nm.

Then, over the light-emitting layer 113, a film of 2-[3'-(dibenzothiophen-4-yl)biphenyl-3-yl]dibenzo[f,h]quinoxaline (abbreviation: 2mDBTBPDBq-II), which is represented by Structural Formula (vii), was formed by evaporation to a thickness of 10 nm, and a film of 2,9-bis(naphthalen-2-yl)-4,7-diphenyl-1,10-phenanthroline (abbreviation: NBPhen) represented by Structural Formula (viii) was formed by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, Light-emitting Element 4 of this example was fabricated.

The element structure of Light-emitting Element 4 is shown in the following table.

TABLE 6

| Hole-injection layer | Hole-transport layer | | | Light-emitting layer | Electron-transport layer | | Electron-injection layer |
|---|---|---|---|---|---|---|---|
| | 1 | 2 | 3 | | | | |
| 5 nm | 10 nm | 10 nm | 10 nm | 25 nm | 10 nm | 15 nm | 1 nm |
| HAT-CN | NPB | BBAβNB | βNPβNC | cgDBCzPA:1,6mMemFLPAPrn (1:0.03) | 2mDBTBPDBq-II | NBPhen | LiF |

Light-emitting Element 4 was sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics and reliability of Light-emitting Element 4 were measured. Note that the measurement was carried out at room temperature (in an atmosphere kept at 25° C.).

Figure 25:
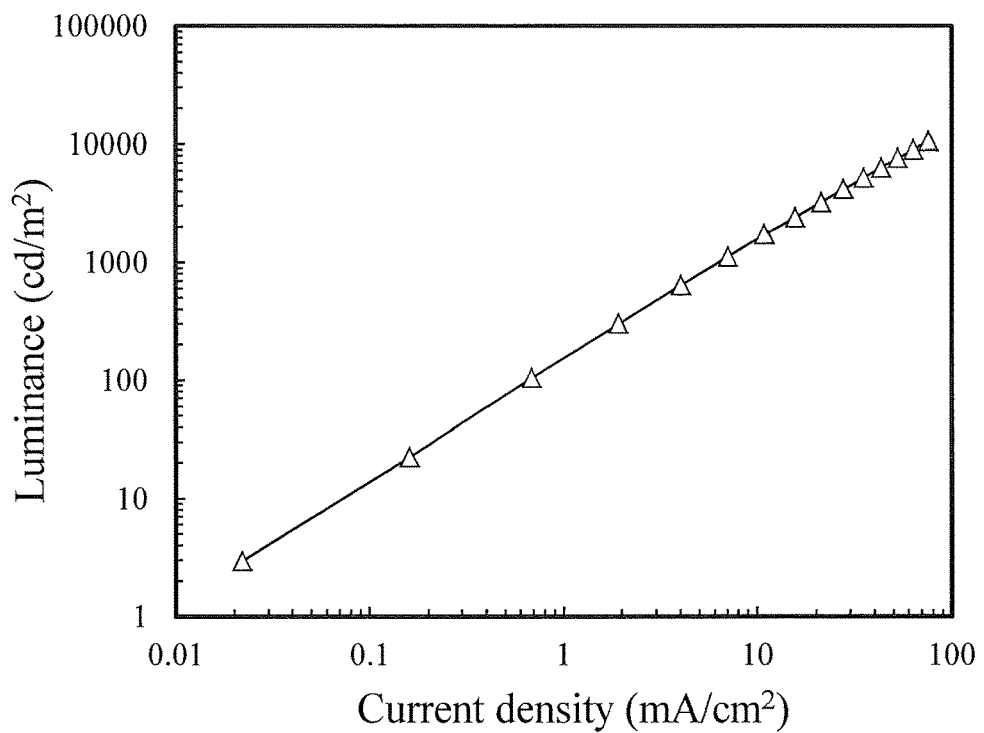
FIG. 25 shows the luminance-current density characteristics of Light-emitting Element 4.
Figure 26:
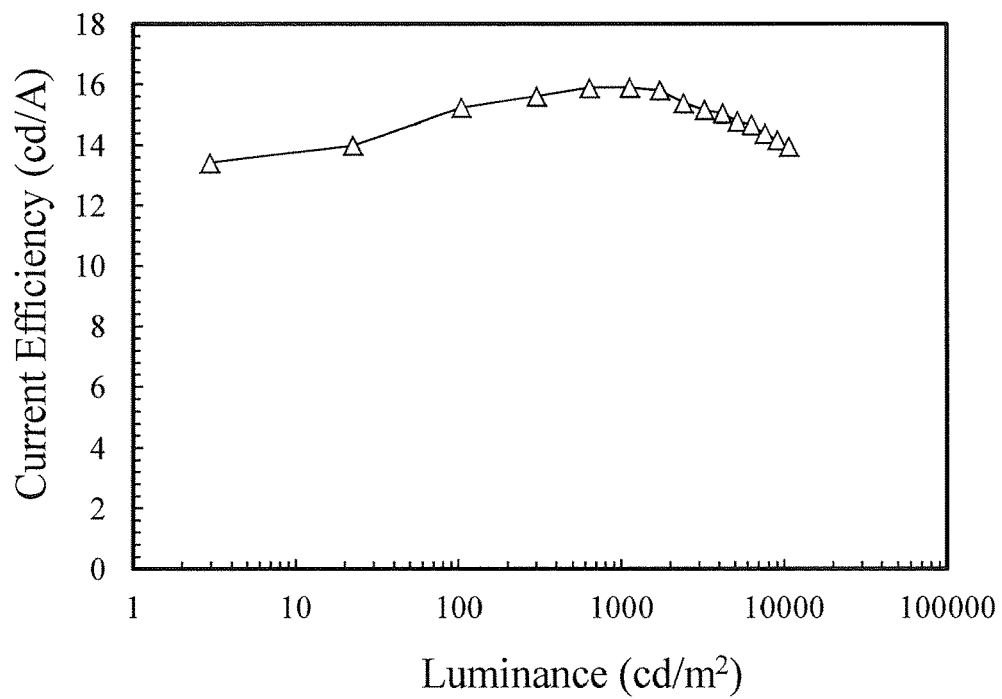
FIG. 26 shows the current efficiency-luminance characteristics of Light-emitting Element 4.
Figure 27:
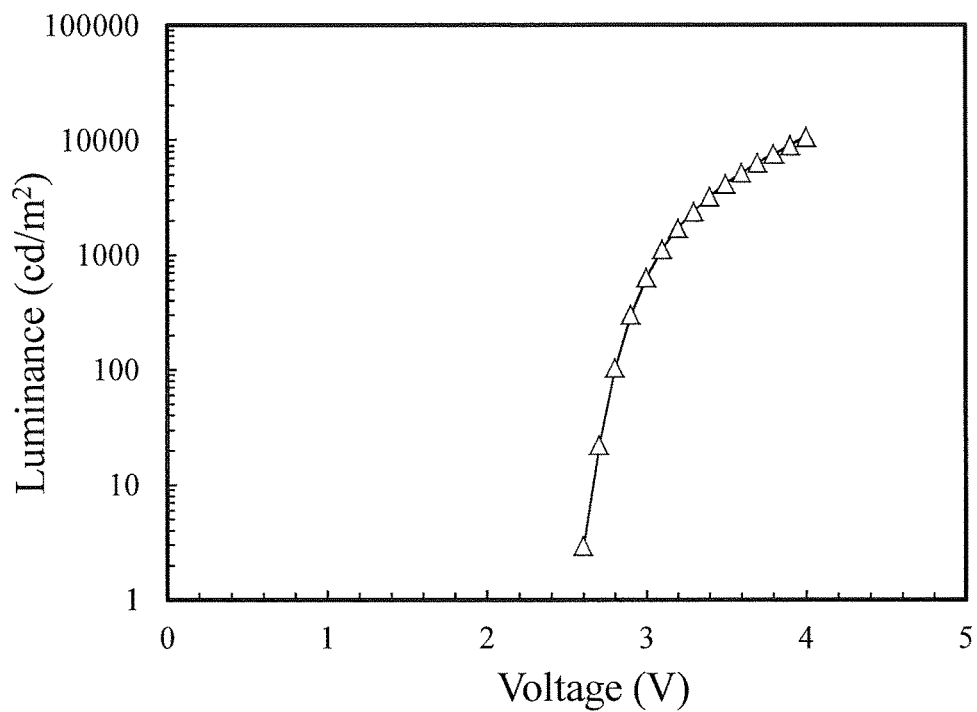
FIG. 27 shows the luminance-voltage characteristics of Light-emitting Element 4.
Figure 28:
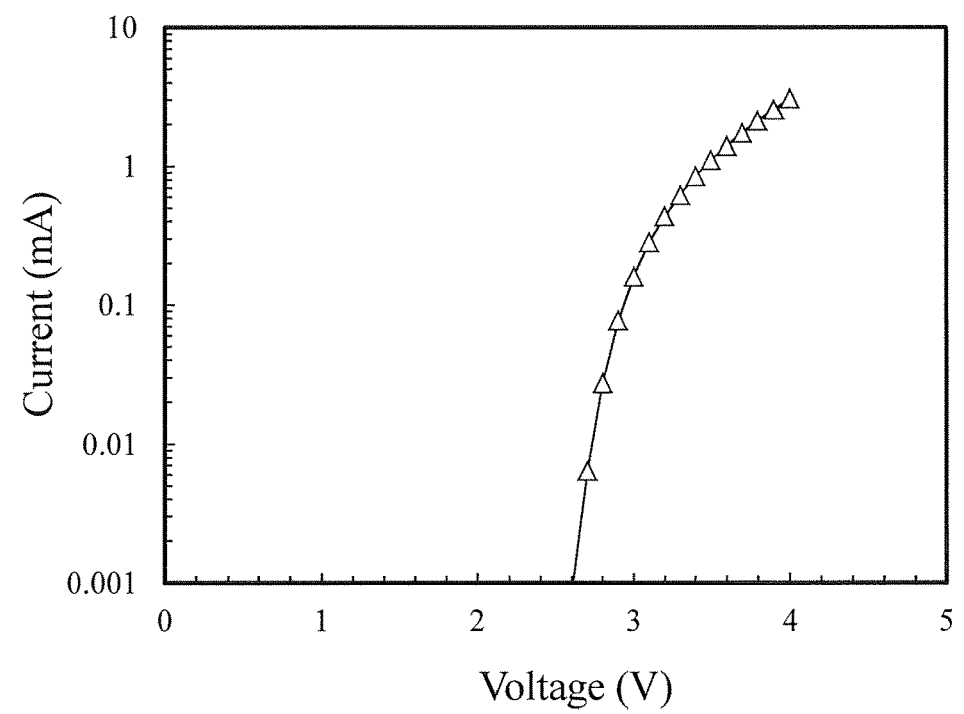
FIG. 28 shows the current-voltage characteristics of Light-emitting Element 4.
Figure 29:
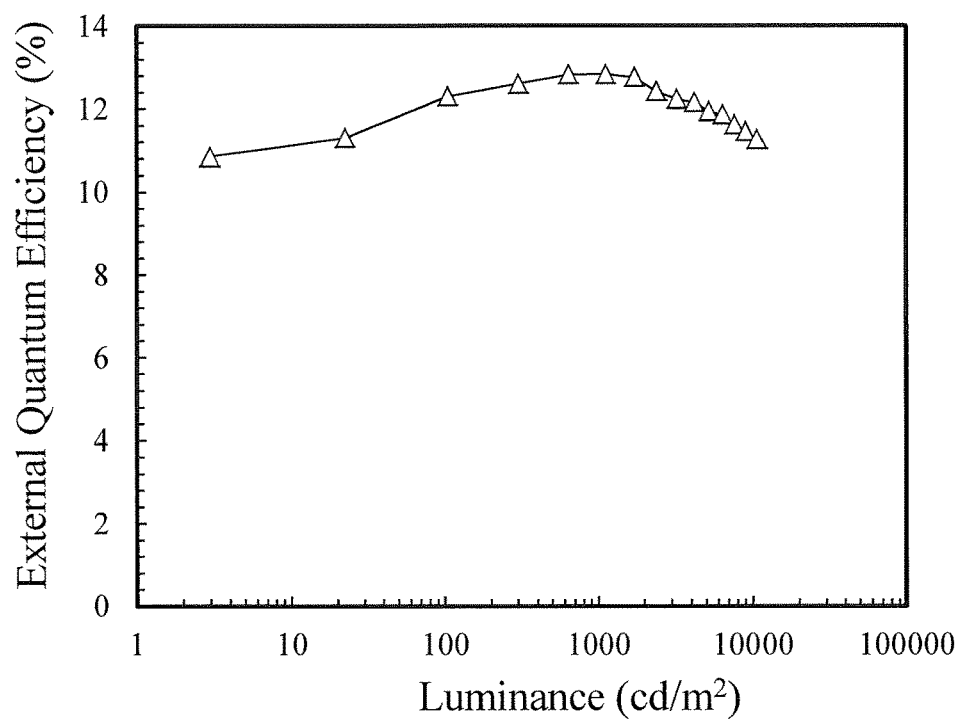
FIG. 29 shows the external quantum efficiency-luminance characteristics of Light-emitting Element 4.
Figure 30:
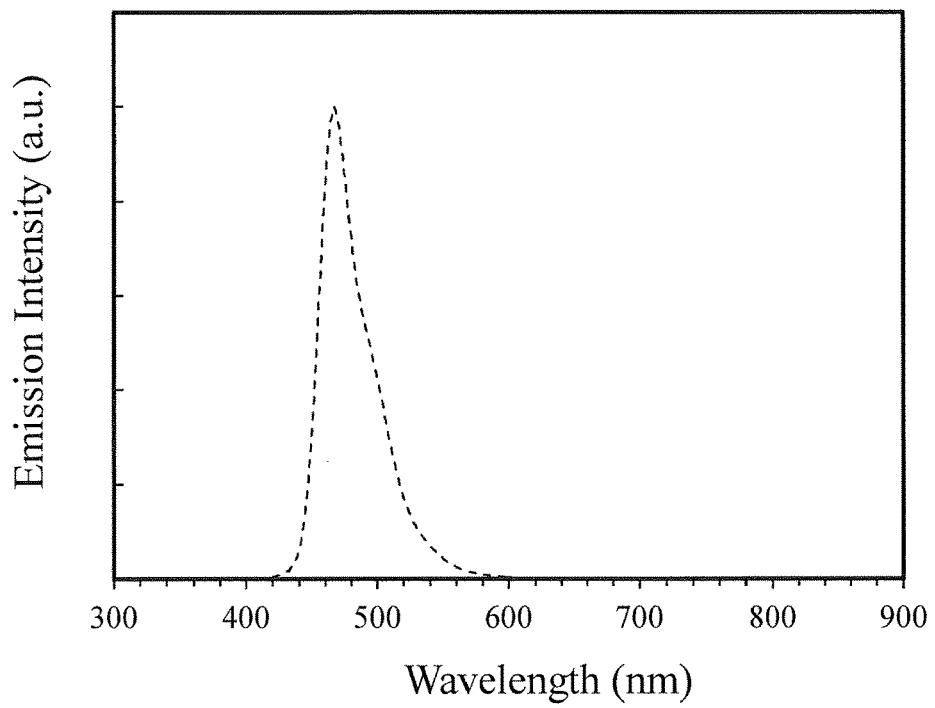
FIG. 30 shows the emission spectrum of Light-emitting Element 4.

FIG. 25 shows the luminance-current density characteristics of Light-emitting Element 4, FIG. 26 shows the current efficiency-luminance characteristics thereof, FIG. 27 shows the luminance-voltage characteristics thereof, FIG. 28 shows the current-voltage characteristics thereof, FIG. 29 shows the external quantum efficiency-luminance characteristics thereof, and FIG. 30 shows the emission spectrum thereof. Table 7 shows the main characteristics of Light-emitting Element 4 at a luminance of about 1000 cd/m².

TABLE 7

| Voltage (V) | Current (mA) | Current density (mA/cm²) | chromaticity x | chromaticity y | Current Efficiency (cd/A) | External Quantum Efficiency (%) |
|---|---|---|---|---|---|---|
| 3.1 | 0.28 | 7.1 | 0.14 | 0.18 | 15.9 | 12.8 |

From FIG. 25 to FIG. 30 and Table 7, it was found that Light-emitting Element 4 was a blue light-emitting element with favorable characteristics.

Figure 31:
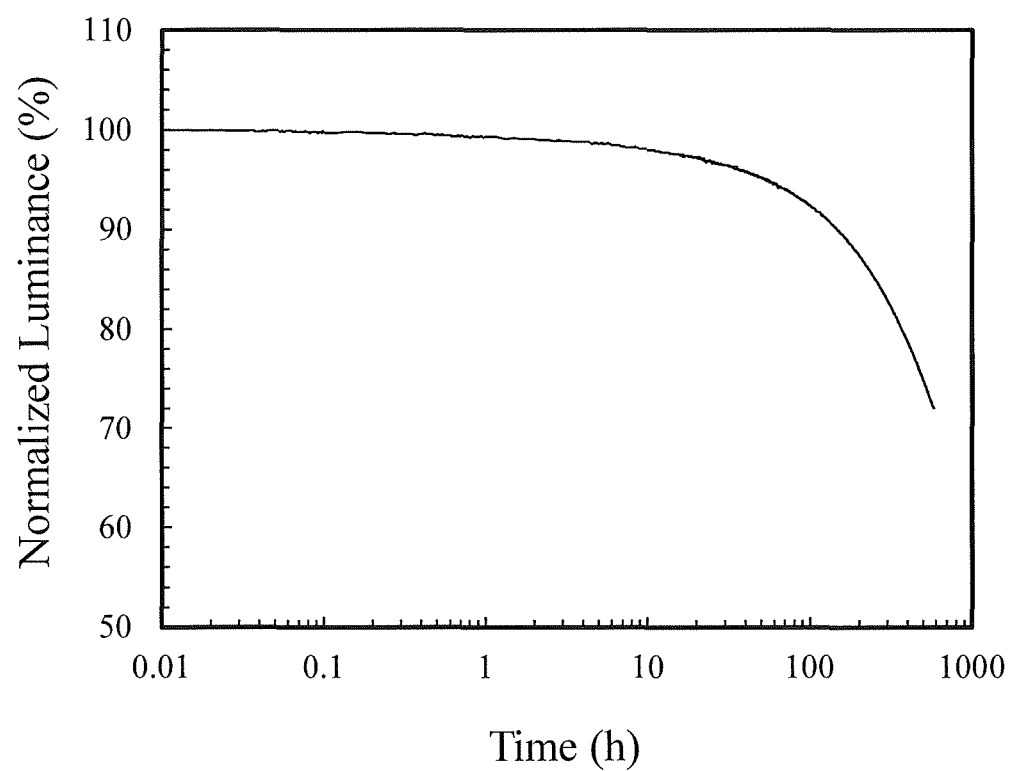
FIG. 31 shows the time dependence of normalized luminance of Light-emitting Element 4.

FIG. 31 shows driving time-dependent change in luminance under the conditions where the current value was set to 2 mA and the current density was constant. As shown in FIG. 31, Light-emitting Element 4 of one embodiment of the present invention was found to be a long-lifetime light-emitting element with a small reduction in luminance over driving time.

Also in Light-emitting Element 4, a decrease in luminance in the high-luminance region was found to be small. In other words, the light-emitting element in this example has a structure that allows reducing of a roll-off of the efficiency at a high-luminance side and accordingly allows emitting of high-luminance light while maintaining a high efficiency.

Table 8 shows the HOMO levels of the first to third hole-transport materials, the host material, and the light-emitting material of Light-emitting Element 4 in this example. Note that the HOMO level and the LUMO level were obtained through a cyclic voltammetry (CV) measurement. A calculation method is similar to that in Example 1.

TABLE 8

| material | Hole-transport layer | | | Light-emitting layer | | Electron-transport layer | |
|---|---|---|---|---|---|---|---|
| | first NPB | second BBAβNB | third βNPβNC | host cgDBCzPA | light-emitting 1,6mMemFLPAPrn | first 2mDBTBPDBq-II | second NBPhen |
| HOMO level (eV) | −5.38 | −5.47 | −5.77 | −5.69 | −5.40 | — | — |
| LUMO level (eV) | — | — | — | −2.74 | — | −2.94 | −2.83 |

As shown in the above table, as for the materials used in Light-emitting Element 4, the HOMO level of the second hole-transport material is deeper than the HOMO level of the first hole-transport material, the HOMO level of the host material is deeper than the HOMO level of the second hole-transport material, and the HOMO level of the third hole-transport material is deeper than the HOMO level of the host material. Furthermore, the HOMO level of the light-emitting material is shallower than the HOMO level of the host material.

The HOMO level of NPB, which is the first hole-transport material, is as shallow as −5.38 eV and can easily cause charge separation by interacting with the LUMO level (−4.41 eV) of HAT-CN.

Here, the HOMO level of cgDBCzPA, which is the host material, is −5.69 eV and its difference from the HOMO level of NPB is 0.31 eV. On the other hand, the HOMO level of 1,6mMemFLPAPrn, which is the light-emitting material, is −5.40 eV and its difference from the HOMO level of NPB is 0.02 eV. Since the difference in HOMO level between the light-emitting material and the first hole-transport material is small, holes are probably injected to the light-emitting material easily when the light-emitting element has a structure in which the first hole-transport layer 112-1 is in contact with the light-emitting layer 113. When the holes are directly injected to the light-emitting material, the holes are trapped at the interface between the first hole-transport layer 112-1 and the light-emitting layer by the light-emitting material, whereby the light-emitting region might be localized to promote deterioration. Furthermore, holes of the hole-transport material of the first hole-transport layer 112-1 are less likely to enter the host material of the light-emitting layer. Therefore, holes and electrons are accumulated in the hole-transport material and the host material, respectively. Accordingly, an exciplex with lower energy than the light-emitting material might be formed between the hole-transport material and the host material, which tends to cause disadvantages such as reduction in emission efficiency.

In Light-emitting Element 4, the second hole-transport material whose HOMO level is shallower than the HOMO level of the host material but deeper than the HOMO level of the first hole-transport material is used for the second hole-transport layer 112-2, whereby holes are first injected from the first hole-transport layer 112-1 to the second hole-transport layer 112-2. The HOMO level of the second hole-transport material, BBAβNB, is −5.47 eV, and its difference from the HOMO level of the first hole-transport material, NPB, is as small as 0.09 eV. Accordingly, holes are smoothly injected from the first hole-transport layer 112-1 to the second hole-transport layer 112-2.

Here, on the assumption that the light-emitting element has a structure in which the second hole-transport layer 112-2 is in contact with the light-emitting layer 113, when holes are injected from the second hole-transport layer 112-2 to the light-emitting layer 113, a barrier of approximately 0.22 eV exists between the second hole-transport material and the host material. With such a difference, holes are usually injected without problems. Meanwhile, the HOMO level of the light-emitting material included in the light-emitting layer 113 is −5.40 eV, and thus a barrier to hole injection from the second hole-transport material to the light-emitting material does not exist. Therefore, holes are preferentially injected to the light-emitting material than to the host material eventually. As described above, direct injection of holes to the light-emitting material is likely to cause disadvantages such as acceleration of deterioration and reduction in emission efficiency.

Thus, in Light-emitting Element 4 of one embodiment of the present invention, the third hole-transport layer 112-3 was further provided between the second hole-transport layer 112-2 and the light-emitting layer 113. The HOMO level of βNPβNC, which is the third hole-transport material included in the third hole-transport layer 112-3, is −5.77 eV and deeper than the HOMO level of the host material. Therefore, holes are injected from the second hole-transport material to the third hole-transport material without problems. In addition, holes are preferentially injected to the host material because there is no barrier to hole injection from the third hole-transport material to the host material and also because of the mixing ratio between the host material and the light-emitting material. Hence, few holes are injected to the light-emitting material directly. Note that the difference in HOMO level between the second hole-transport material and the third hole-transport material is 0.30 eV (less than or equal to 0.3 eV with one significant figure), and thus, holes are injected from the second hole-transport material to the third hole-transport material without problems.

Although the holes injected to the host material are partly trapped in the light-emitting material, they can be moved toward the second electrode while being trapped moderately, and the host material is an anthracene compound, which also has an electron-transport property; accordingly, the driving voltage does not increase. In addition, the light-emitting region extends over the light-emitting layer 113 without being localized, and deterioration is not promoted.

Moreover, the light-emitting element of this example includes cgDBCzPA as the host material, 2mDBIBPDBq-II as the first electron-transport material, and NBPhen as the second electron-transport material, the LUMO levels of which are estimated to −2.74 eV, −2.94 eV, and −2.83 eV, respectively. With this structure, the light-emitting element is not prone to have excessive electrons and can have a longer lifetime and a higher external quantum efficiency.

From the above, Light-emitting Element 4 of this example was found to have highly favorable characteristics, i.e., a long lifetime, a high emission efficiency, and only a slight decrease in efficiency at a high-luminance side.

EXAMPLE 3

In this example, Light-emitting Element 5 of one embodiment of the present invention, which is described in the embodiment, is described. Structural formulae of organic compounds used in Light-emitting Element 5 are shown below.

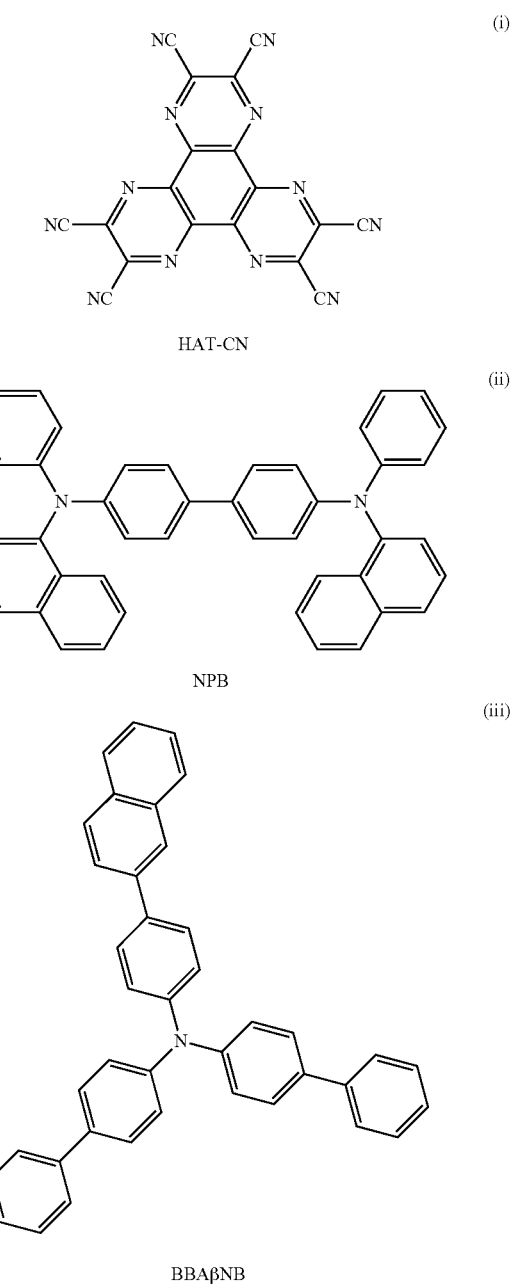

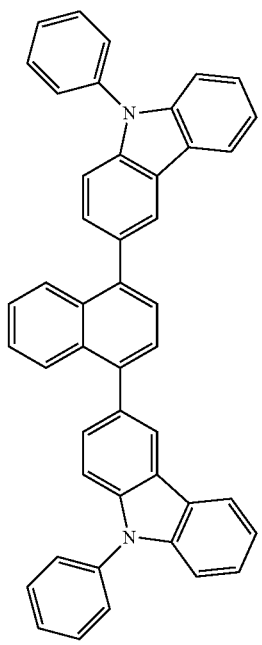

PCzN2

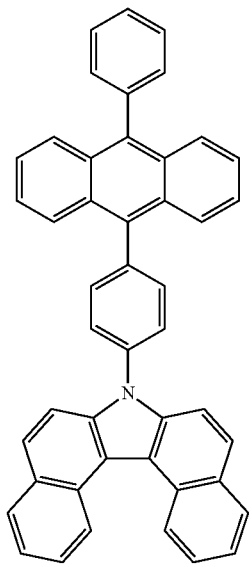

cgDBCzPA

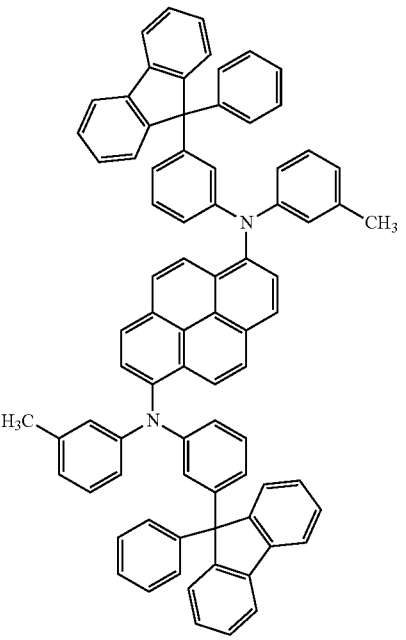

1,6mMemFLPAPm

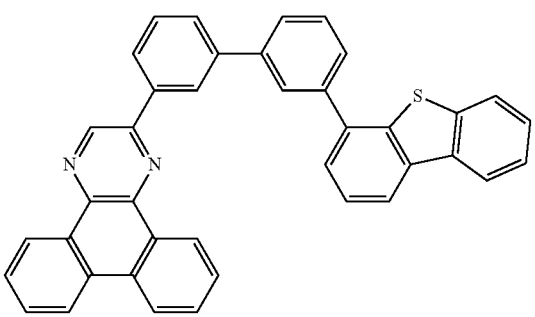

2mDBTBPDBq-II

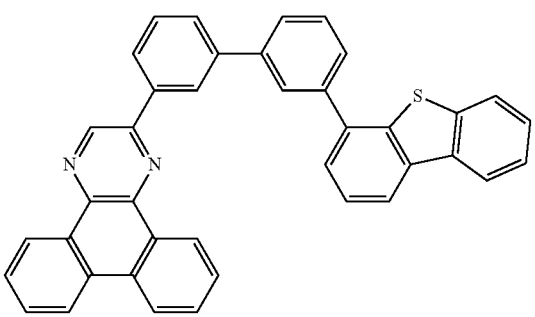

NBPhen (Fabrication Method of Light-Emitting Element 5)

First, a film of indium tin oxide containing silicon oxide (ITSO) was formed over a glass substrate by a sputtering method, so that the first electrode 101 was formed. The thickness of the first electrode 101 was 70 nm and the electrode area was 4 mm² (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 2,3,6,7,10,11-hexacyano-1,4,5,8,9,12-hexaazatriphenylene (abbreviation: HAT-CN) represented by Structural Formula (i) was deposited by evaporation to a thickness of 5 nm by an evaporation method using resistance heating, so that the hole-injection layer 111 was formed.

Next, a film of 4,4'-bis[N-(1-naphthyl)-N-phenylamino] biphenyl (abbreviation: NPB) represented by Structural Formula (ii) was formed by evaporation to a thickness of 10 nm on the hole-injection layer 111 to form the first hole-transport layer 112-1; a film of 4-(2-naphthyl)-4',4"-diphenyltriphenylamine (abbreviation: BBAβNB) represented by Structural Formula (iii) was formed by evaporation to a thickness of 10 nm on the first hole-transport layer 112-1 to form the second hole-transport layer 112-2; and a film of 3,3'-(naphthalen-1,4-diyl)bis(9-phenyl-9H-carbazole) (abbreviation: PCzN2) represented by Structural Formula (xii) was formed by evaporation to a thickness of 10 nm on the second hole-transport layer 112-2 to form the third hole-transport layer 112-3.

After that, the light-emitting layer 113 was formed by co-evaporation of 7-[4-(10-phenyl-9-anthryl)phenyl]-7H-dibenzo[c,g]carbazole (abbreviation: cgDBCzPA) represented by Structural Formula (v) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (vi) at a weight ratio of 1:0.03 (=cgDBCzPA: 1,6mMemFLPAPrn) to a thickness of 25 nm.

Then, over the light-emitting layer 113, a film of 2-[3'-(dibenzothiophen-4-yl)biphenyl-3-yl]dibenzo[f,h]quinoxaline (abbreviation: 2mDBTBPDBq-II), which is represented by Structural Formula (vii), was formed by evaporation to a thickness of 10 nm, and a film of 2,9-bis(naphthalen-2-yl)-4,7-diphenyl-1,10-phenanthroline (abbreviation: NBPhen) represented by Structural Formula (viii) was formed by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, Light-emitting Element 5 of this example was fabricated.

The element structure of Light-emitting Element 5 is shown in the following table.

Light-emitting Element 5 was sealed using a glass substrate in a glove box containing a nitrogen atmosphere so as not to be exposed to the air (specifically, a sealant was applied to surround the element and UV treatment and heat treatment at 80° C. for 1 hour were performed at the time of sealing). Then, the initial characteristics and reliability of Light-emitting Element 5 were measured. Note that the measurement was carried out at room temperature (in an atmosphere kept at 25° C.).

Figure 37:
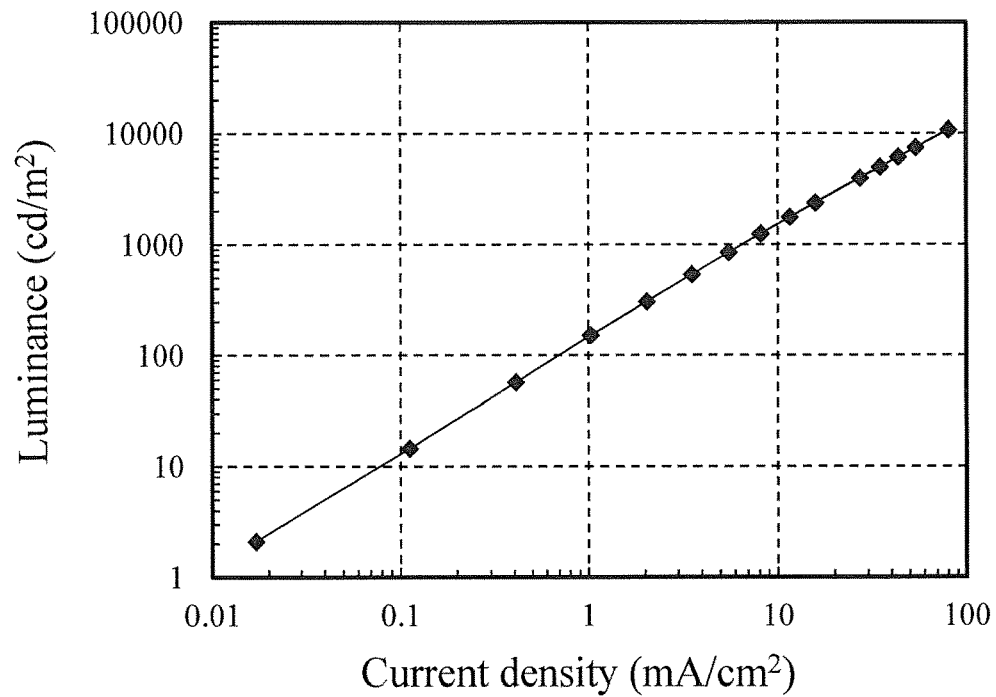
FIG. 37 shows the luminance-current density characteristics of Light-emitting Element 5.
Figure 38:
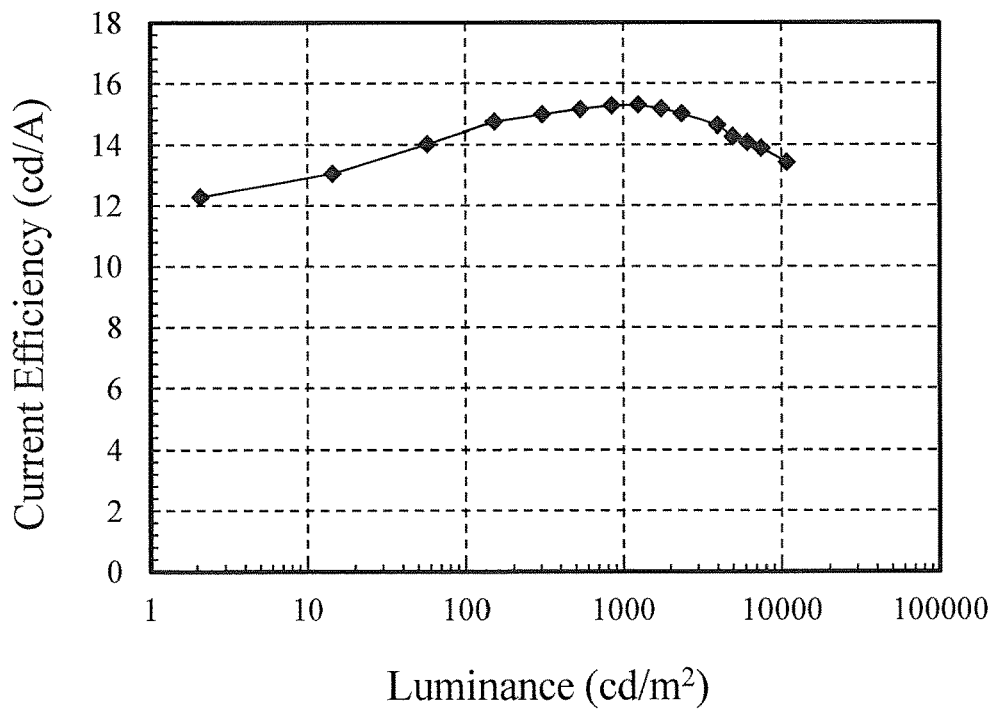
FIG. 38 shows the current efficiency-luminance characteristics of Light-emitting Element 5.
Figure 39:
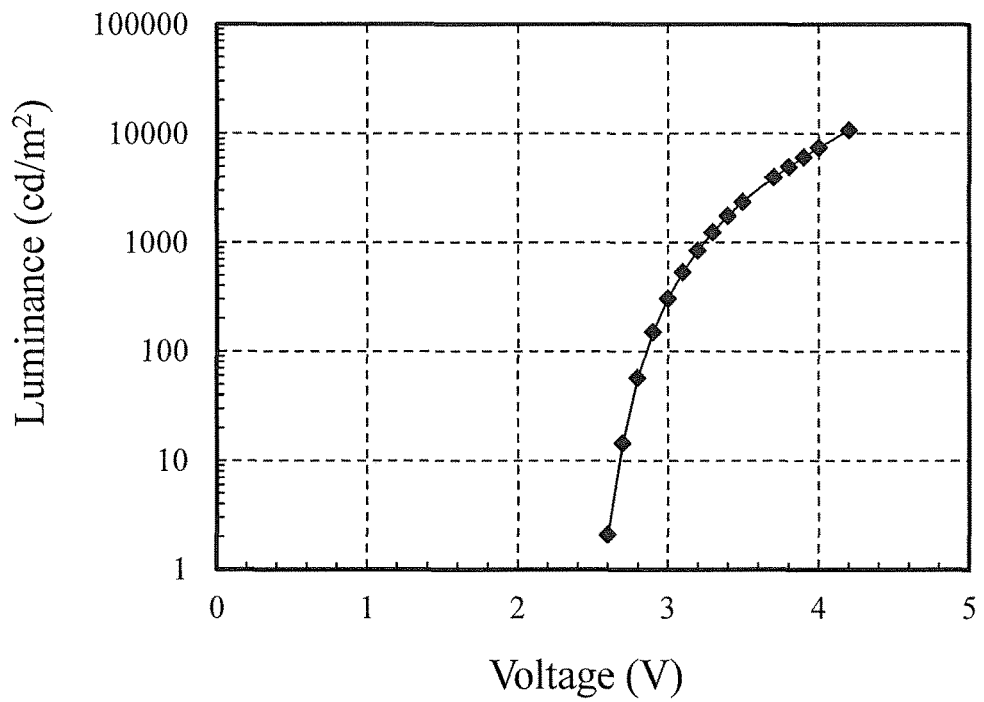
FIG. 39 shows the luminance-voltage characteristics of Light-emitting Element 5.
Figure 40:
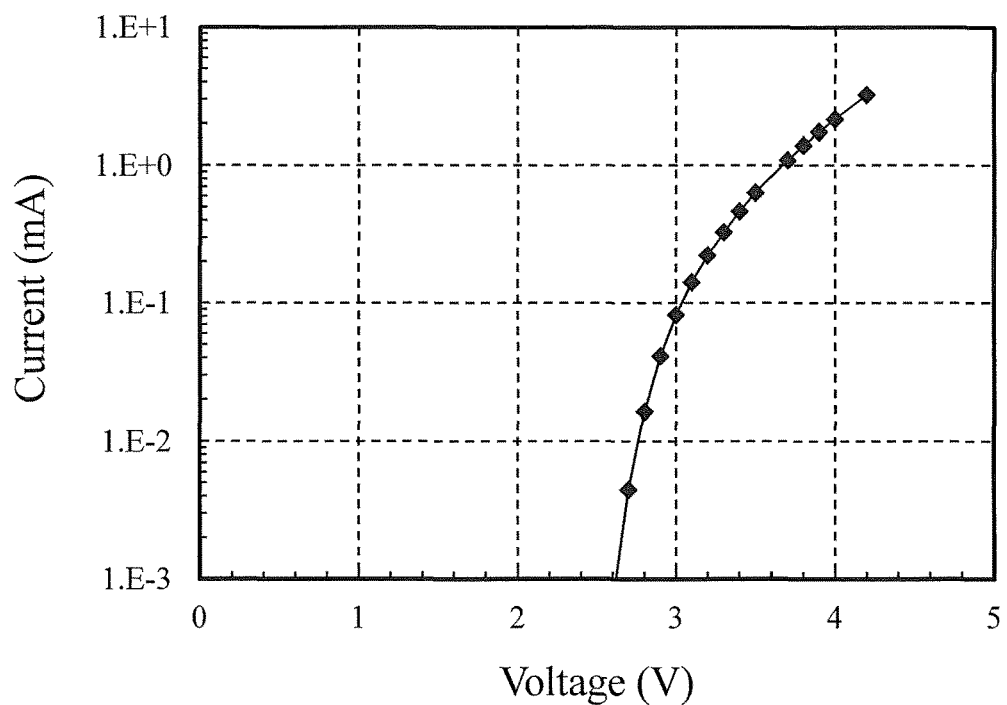
FIG. 40 shows the current-voltage characteristics of Light-emitting Element 5.
Figure 41:
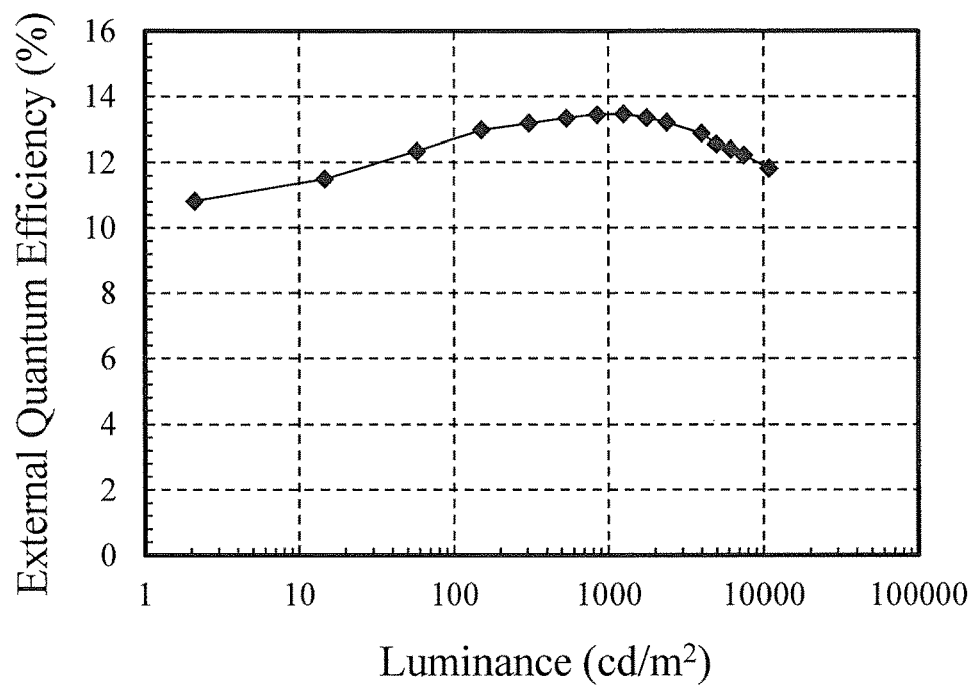
FIG. 41 shows the external quantum efficiency-luminance characteristics of Light-emitting Element 5.
Figure 42:
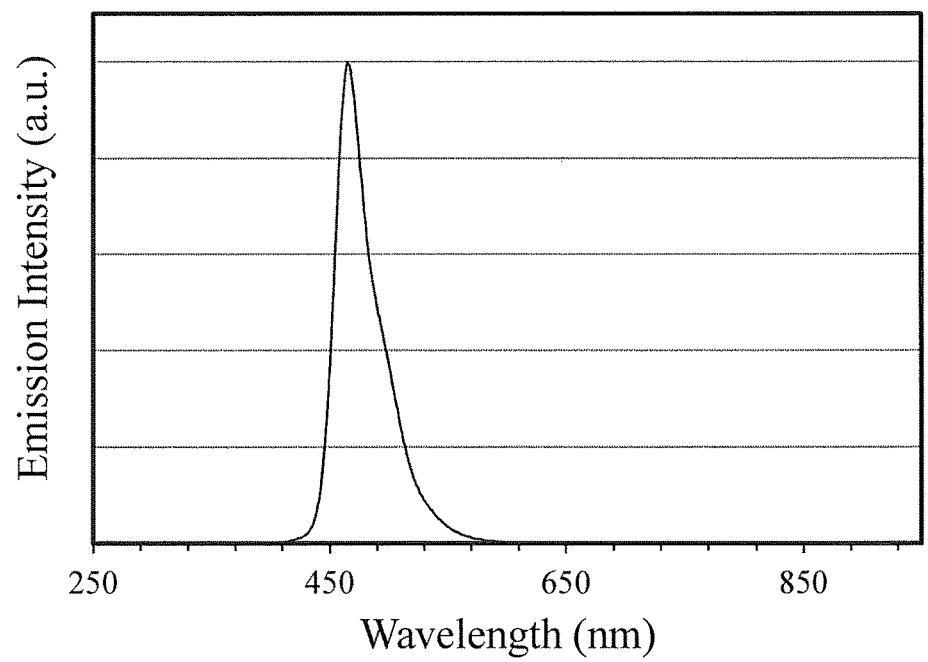
FIG. 42 shows the emission spectrum of Light-emitting Element 5.

FIG. 37 shows the luminance-current density characteristics of Light-emitting Element 5, FIG. 38 shows the current efficiency-luminance characteristics thereof, FIG. 39 shows the luminance-voltage characteristics thereof, FIG. 40 shows the current-voltage characteristics thereof, FIG. 41 shows the external quantum efficiency-luminance characteristics thereof, and FIG. 42 shows the emission spectrum thereof. Table 10 shows the main characteristics of Light-emitting Element 5 at a luminance of about 1000 cd/m².

TABLE 10

| Voltage (V) | Current (mA) | Current density (mA/cm²) | chromaticity x | chromaticity y | Current Efficiency (cd/A) | External Quantum Efficiency (%) |
|---|---|---|---|---|---|---|
| 3.2 | 0.22 | 5.6 | 0.14 | 0.16 | 15.3 | 13.4 |

From FIG. 37 to FIG. 42 and Table 10, it was found that Light-emitting Element 5 was a blue light-emitting element with favorable characteristics.

Figure 43:
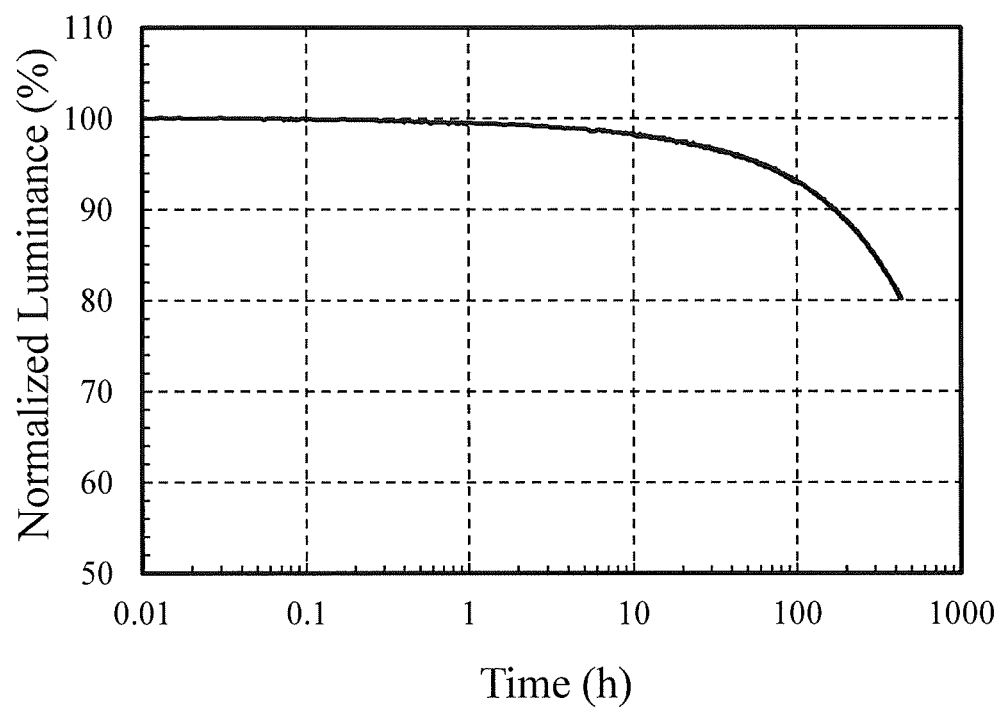
FIG. 43 shows the time dependence of normalized luminance of Light-emitting Element 5.

FIG. 43 shows driving time-dependent change in luminance under the conditions where the current value was set to 2 mA and the current density was constant. As shown in FIG. 43, Light-emitting Element 5 of one embodiment of the present invention was found to be a long-lifetime light-emitting element with a small reduction in luminance over driving time.

Also in Light-emitting Element 5, a decrease in luminance in the high-luminance region was found to be small. In other words, the light-emitting element in this example has a structure that allows reducing of a roll-off of the efficiency at a high-luminance side and accordingly allows emitting of high-luminance light while maintaining a high efficiency.

Table 11 shows the HOMO levels of the first to third hole-transport materials, the host material, and the light-emitting material of Light-emitting Element 5 in this example. Note that the HOMO level and the LUMO level were obtained through a cyclic voltammetry (CV) measurement. A calculation method is similar to that in Example 1.

TABLE 9

| Hole-injection layer | Hole-transport layer | | | Light-emitting layer | Electron-transport layer | | Electron-injection layer |
|---|---|---|---|---|---|---|---|
| | 1 | 2 | 3 | | | | |
| 5 nm | 10 nm | 10 nm | 10 nm | 25 nm | 10 nm | 15 nm | 1 nm |
| HAT-CN | NPB | BBAβNB | PCzN2 | cgDBCzPA:1,6mMemFLPAPrn (1:0.03) | 2mDBTBPDBq-II | NBPhen | LiF |

TABLE 11

| material | Hole-transport layer | | | Light-emitting layer | | Electron-transport layer | |
|---|---|---|---|---|---|---|---|
| | first NPB | second BBAβNB | third PCzN2 | host cgDBCzPA | light-emitting 1,6mMemFLPAPrn | first 2mDBTBPDBq-II | second NBPhen |
| HOMO level (eV) | −5.38 | −5.47 | −5.71 | −5.69 | −5.40 | — | — |
| LUMO level (eV) | — | — | — | −2.74 | — | −2.94 | −2.83 |

As shown in the above table, as for the materials used in Light-emitting Element 5, the HOMO level of the second hole-transport material is deeper than the HOMO level of the first hole-transport material, the HOMO level of the host material is deeper than the HOMO level of the second hole-transport material, and the HOMO level of the third hole-transport material is deeper than the HOMO level of the host material. Furthermore, the HOMO level of the light-emitting material is shallower than the HOMO level of the host material.

The HOMO level of NPB, which is the first hole-transport material, is as shallow as −5.38 eV and can easily cause charge separation by interacting with the LUMO level (−4.41 eV) of HAT-CN.

Here, the HOMO level of cgDBCzPA, which is the host material, is −5.69 eV and its difference from the HOMO level of NPB is 0.31 eV. On the other hand, the HOMO level of 1,6mMemFLPAPrn, which is the light-emitting material, is −5.40 eV and its difference from the HOMO level of NPB is 0.02 eV. Since the difference in HOMO level between the light-emitting material and the first hole-transport material is small, holes are probably injected to the light-emitting material easily when the light-emitting element has a structure in which the first hole-transport layer 112-1 is in contact with the light-emitting layer 113. When the holes are directly injected to the light-emitting material, the holes are trapped at the interface between the first hole-transport layer 112-1 and the light-emitting layer by the light-emitting material, whereby the light-emitting region might be localized to promote deterioration. Furthermore, holes of the hole-transport material of the first hole-transport layer 112-1 are less likely to enter the host material of the light-emitting layer. Therefore, holes and electrons are accumulated in the hole-transport material and the host material, respectively. Accordingly, an exciplex with lower energy than the light-emitting material might be formed between the hole-transport material and the host material, which tends to cause disadvantages such as reduction in emission efficiency.

In Light-emitting Element 5, the second hole-transport material whose HOMO level is shallower than the HOMO level of the host material but deeper than the HOMO level of the first hole-transport material is used for the second hole-transport layer 112-2, whereby holes are first injected from the first hole-transport layer 112-1 to the second hole-transport layer 112-2. The HOMO level of the second hole-transport material, BBAβNB, is −5.47 eV, and its difference from the HOMO level of the first hole-transport material, NPB, is as small as 0.09 eV. Accordingly, holes are smoothly injected from the first hole-transport layer 112-1 to the second hole-transport layer 112-2.

Here, on the assumption that the light-emitting element has a structure in which the second hole-transport layer 112-2 is in contact with the light-emitting layer 113, when holes are injected from the second hole-transport layer 112-2 to the light-emitting layer 113, a barrier of approximately 0.22 eV exists between the second hole-transport material and the host material. With such a difference, holes are usually injected without problems. Meanwhile, the HOMO level of the light-emitting material included in the light-emitting layer 113 is −5.40 eV, and thus a barrier to hole injection from the second hole-transport material to the light-emitting material does not exist. Therefore, holes are preferentially injected to the light-emitting material than to the host material eventually. As described above, direct injection of holes to the light-emitting material is likely to cause disadvantages such as acceleration of deterioration and reduction in emission efficiency.

Thus, in Light-emitting Element 5 of one embodiment of the present invention, the third hole-transport layer 112-3 was further provided between the second hole-transport layer 112-2 and the light-emitting layer 113. The HOMO level of PCzN2, which is the third hole-transport material included in the third hole-transport layer 112-3, is −5.71 eV that is similar to but slightly deeper than the HOMO level of the host material. Therefore, holes are injected from the second hole-transport material to the third hole-transport material without problems. In addition, holes are probably injected to the host material because there is no barrier to hole injection from the third hole-transport material to the host material and also because of the mixing ratio between the host material and the light-emitting material. Hence, few holes are injected to the light-emitting material directly. Note that the difference in HOMO level between the second hole-transport material and the third hole-transport material is 0.24 eV (less than or equal to 0.3 eV with one significant figure), and thus, holes are injected from the second hole-transport material to the third hole-transport material without problems.

Although the holes injected to the host material are partly trapped in the light-emitting material, they can be moved toward the second electrode while being trapped moderately, and the host material is an anthracene compound, which also has an electron-transport property; accordingly, the driving voltage does not increase. In addition, the light-emitting region extends over the light-emitting layer 113 without being localized, and deterioration is not promoted.

Moreover, the light-emitting element of this example includes cgDBCzPA as the host material, 2mDB IBPDBq-II as the first electron-transport material, and NBPhen as the second electron-transport material, the LUMO levels of which are estimated to −2.74 eV, −2.94 eV, and −2.83 eV, respectively. With this structure, the light-emitting element is not prone to have excessive electrons and can have a longer lifetime and a higher external quantum efficiency.

From the above, Light-emitting Element 5 of this example was found to have highly favorable characteristics, i.e., a long lifetime, a high emission efficiency, and only a slight decrease in efficiency at a high-luminance side.

REFERENCE EXAMPLE 1

In this reference example, a method for synthesizing 4-naphthyl-4',4''-diphenyltriphenylamine (abbreviation:

BBAβNB), which was used in Light-emitting Elements 1 and 4, is described. The structural formula of BBAβNB is shown below.

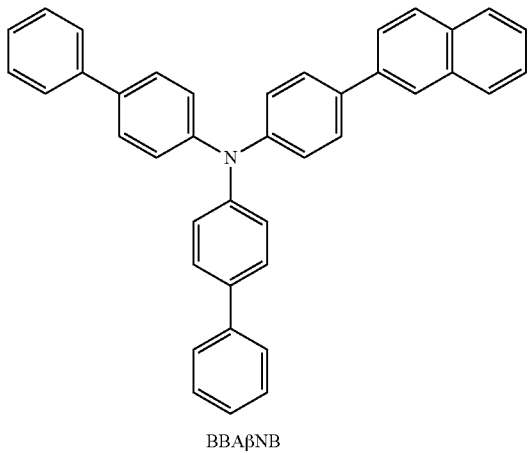 [SMILES: c1ccc(-c2ccc(N(c3ccc(-c4ccccc4)cc3)c3ccc(-c4ccc5ccccc5c4)cc3)cc2)cc1]

BBAβNB

Into a 200 mL three-neck flask were put 2.3 g (7.1 mmol) of bis(4-biphenylyl)amine, 2.0 g (7.1 mmol) of 2-(4-bromophenyl)naphthalene, 1.5 g (15 mmol) of sodium tert-butoxide (abbreviation: tert-BuONa), and 0.16 g (0.40 mmol) of 2-dicyclohexylphosphino-2',6'-dimethoxy-1,1'-biphenyl (abbreviation: SPhos). The air in the flask was replaced with nitrogen, and then 35 mL of xylene was added. After this mixture was degassed under reduced pressure, stirring was performed at 60° C. under a nitrogen stream, 0.12 g (0.20 mmol) of bis(dibenzylideneacetone)palladium (0) was added, and this mixture was stirred at 120° C. for 7 hours. After the stirring, the obtained mixture was washed with water and a saturated aqueous solution of sodium chloride, and the organic layer was washed with magnesium sulfate. After the magnesium sulfate was removed by gravity filtration, the obtained filtrate was concentrated to give a brown solid. The brown solid was purified by high performance liquid chromatography (mobile phase: chloroform) to give 3.5 g of an objective light yellow solid in a yield of 93%. The synthesis scheme of this reaction is shown below.

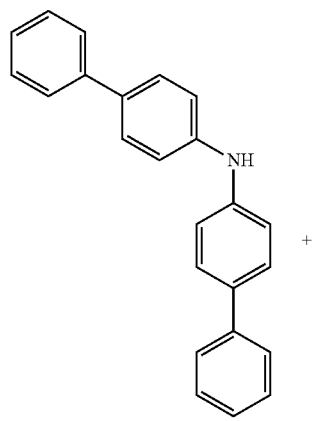

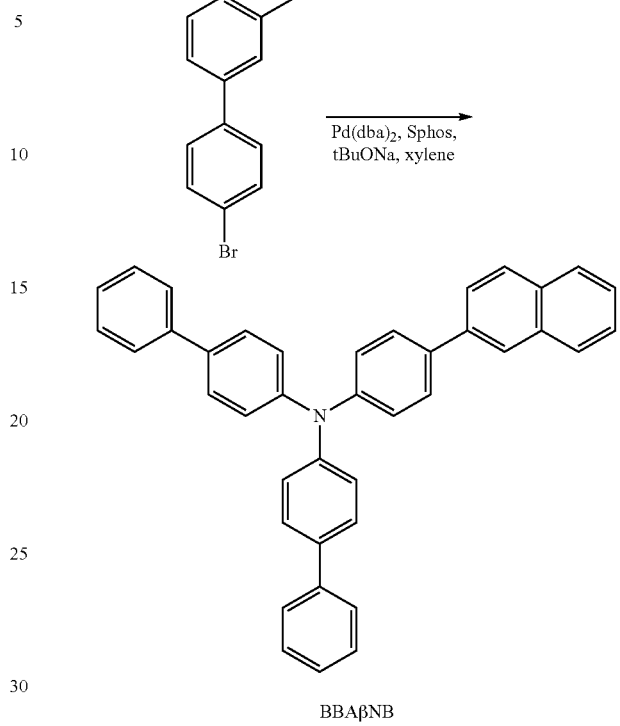

BBAβNB $^1$H NMR data of the obtained white solid are shown below.

$^1$H NMR (dichloromethane-d2, 500 MHz): δ=7.24 (d, J=9.0 Hz, 4H), 7.26(d, J=8.5 Hz, 2H), 7.31 (d, J=7.5 Hz, 2H), 7.42 (d, J=7.5 Hz, 4H), 7.45-7.50 (m, 2H), 7.55 (d, J=8.5 Hz, 4H), 7.60 (d, J=7.5 Hz, 4H), 7.68 (d, J=8.5 Hz, 2H), 7.76 (dd, J$_1$=2.0 Hz, J$_2$=8.5 Hz, 1H), 7.85 (d, J=8.0 Hz, 1H), 7.90 (t, J=8.05 Hz, 2H), 8.05 (s, 1H).

Figure 32A:
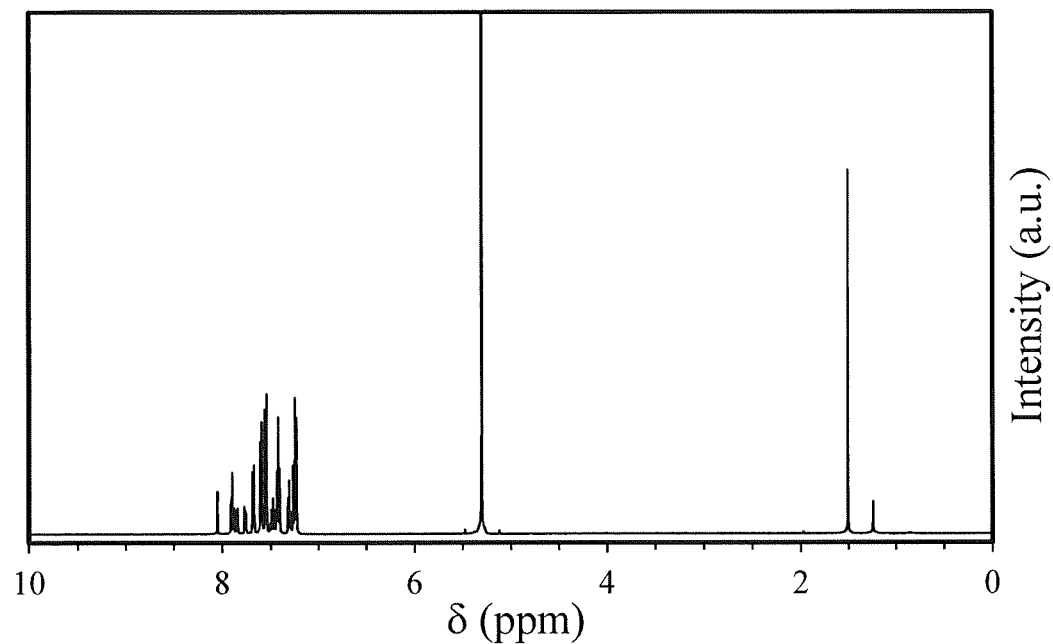
FIGS. 32A and 32B show $^1$H-NMR charts of BBAβNB.
Figure 32B:
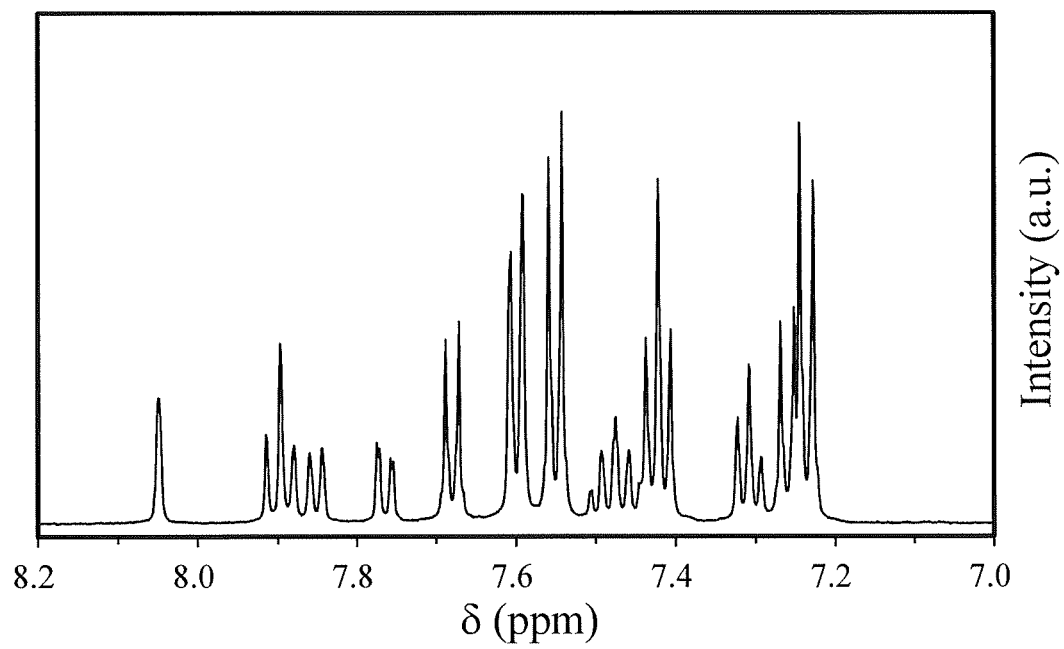

The $^1$H-NMR charts are shown in FIGS. 32A and 32B. Note that FIG. 32B is an enlarged chart of a part in the range from 7.00 ppm to 8.20 ppm of FIG. 32A. The results indicate that BBAβNB was obtained by the synthesis reaction.

By train sublimation, 3.5 g of the obtained white solid (BBAβNB) was purified. The purification by sublimation was carried out under a pressure of 3.4 Pa, with a flow rate of argon gas of 15 mL/min, at a heating temperature of 265° C., and for 16 hours. After the sublimation purification, 2.8 g of a pale yellow glassy solid of a target substance was obtained at a collection rate of 81%.

The HOMO level and the LUMO level of BBAβNB were obtained through a cyclic voltammetry (CV) measurement. A calculation method is shown below.

An electrochemical analyzer (ALS model 600A or 600C, manufactured by BAS Inc.) was used as a measurement apparatus. As for a solution used for the CV measurement, dehydrated dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Furthermore, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag+ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was set to 0.1 V/sec, and an oxidation potential Ea [V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be −4.94 [eV], and thus, the HOMO level and the LUMO level can be obtained from the following formula: HOMO level [eV]=−4.94−Ea and LUMO level [eV]=−4.94−Ec. Furthermore, the CV measurement was repeated 100 times, and the oxidation-reduction wave at the hundredth cycle and the oxidation-reduction wave at the first cycle were compared with each other to examine the electric stability of the compound.

As a result, the HOMO level of BBAβNB was found to be −5.47 eV. In contrast, the LUMO level was found to be −2.28 eV. When the oxidation-reduction wave was repeatedly measured, in the Ea measurement, the peak intensity of the oxidation-reduction wave after the hundredth cycle was maintained to be 83% of that of the oxidation-reduction wave at the first cycle, and in the Ec measurement, the peak intensity of the oxidation-reduction wave after the hundredth cycle was maintained to be 92% of that of the oxidation-reduction wave at the first cycle; thus, resistance to oxidation and reduction of BBAβNB was found to be extremely high.

Further, differential scanning calorimetry (DSC measurement) of BBAβNB was performed by Pyris1DSC manufactured by PerkinElmer, Inc. In the differential scanning calorimetry, after the temperature was raised from −10° C. to 300° C. at a temperature rising rate of 40° C./min, the temperature was held for a minute and then cooled to −10° C. at a temperature decreasing rate of 40° C./min. This operation was repeated twice successively. The DSC measurement result of a second cycle showed that the glass transition point of BBAβNB was 81° C. In addition, the result of the first cycle showed that the melting point of BBAβNB was 241° C.

The thermogravimetry-differential thermal analysis (TG-DTA) of BBAβNB was performed. The measurement was conducted by using a high vacuum differential type differential thermal balance (TG/DTA 2410SA, manufactured by Bruker AXS K.K.). The measurement was performed under atmospheric pressure at a temperature rising rate of 10° C./min under a nitrogen stream (a flow rate of 200 mL/min). In the thermogravimetry-differential thermal analysis, the temperature (decomposition temperature) at which the weight obtained by thermogravimetry was reduced by 5% of the weight at the beginning of the measurement was found to be 412° C., which shows that BBAβNB is a substance with high heat resistance.

REFERENCE EXAMPLE 2

In this reference example, a method for synthesizing 3,6-bis[4-(2-naphthyl)phenyl]-9-phenyl-9H-carbazole (abbreviation: βNP2PC), which was used in Light-emitting Elements 1 to 3, is described. The structural formula of βNP2PC is shown below.

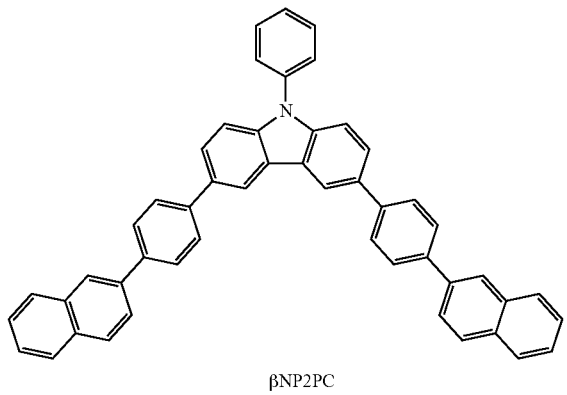 [SMILES: c1ccc(-n2c3ccc(-c4ccc(-c5ccc6ccccc6c5)cc4)cc3c3cc(-c4ccc(-c5ccc6ccccc6c5)cc4)ccc32)cc1]

βNP2PC

Into a 200 mL three-neck flask were put 1.9 g (4.8 mmol) of 3,6-dibromo-9-phenyl-9H-carbazole, 2.4 g (9.7 mol) of 4-(2-naphthyl)phenylboronic acid, 0.12 g (0.40 mmol) of tri(o-tolyl)phosphine, and 2.7 g (19 mmol) of potassium carbonate. The air in the flask was replaced with nitrogen, and then 40 mL of toluene, 10 mL of ethanol, and 10 mL of water were added to the mixture. This mixture was degassed by being stirred while the pressure was reduced. After the degassing, 22 mg (0.10 mmol) of palladium(II) acetate was added to this mixture. This mixture was stirred at 80° C. for 4 hours under a nitrogen stream, so that a solid was precipitated. The precipitated solid was collected by suction filtration. The collected solid was dissolved in approximately 750 mL of hot toluene, and this solution was suction-filtered through Celite (Catalog No. 537-02305, produced by Wako Pure Chemical Industries, Ltd.), alumina, and Florisil (Catalog No. 066-05265, produced by Wako Pure Chemical Industries, Ltd.). The resulting filtrate was concentrated to give a solid. The solid was washed with toluene to give 2.6 g of a target white powder in a yield of 99%.

The synthesis scheme of this reaction is shown below.

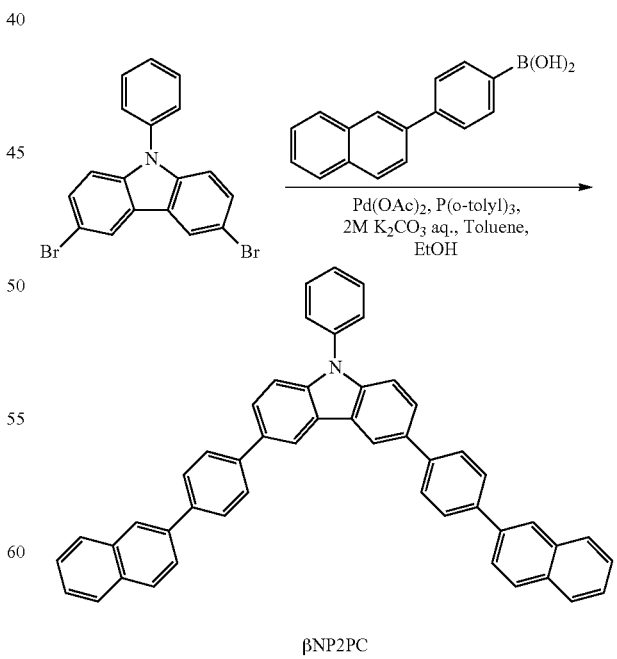

βNP2PC

By a train sublimation method, 2.6 g of the obtained white powder was purified. In the purification by sublimation, the white powder was heated at 350° C. under a pressure of 3.0 Pa with a flow rate of argon gas of 5.0 mL/min. After the purification by sublimation, 2.0 g of a white solid was obtained at a collection rate of 77%.

The obtained substance was analyzed by $^1$H NMR. The measurement data are shown below.

$^1$H NMR (CDCl$_3$, 300 MHz): δ=7.47-7.55 (m, 7H), 7.65 (s, 2H), 7.67 (d, J=2.4 Hz, 2H), 7.76 (dd, J$_1$=8.4 Hz, J$_2$=1.8 Hz, 2H), 7.75-7.97 (m, 16H), 8.14 (d, J=1.8 Hz, 2H), 8.51 (d, J=1.5 Hz, 2H).

Figure 33A:
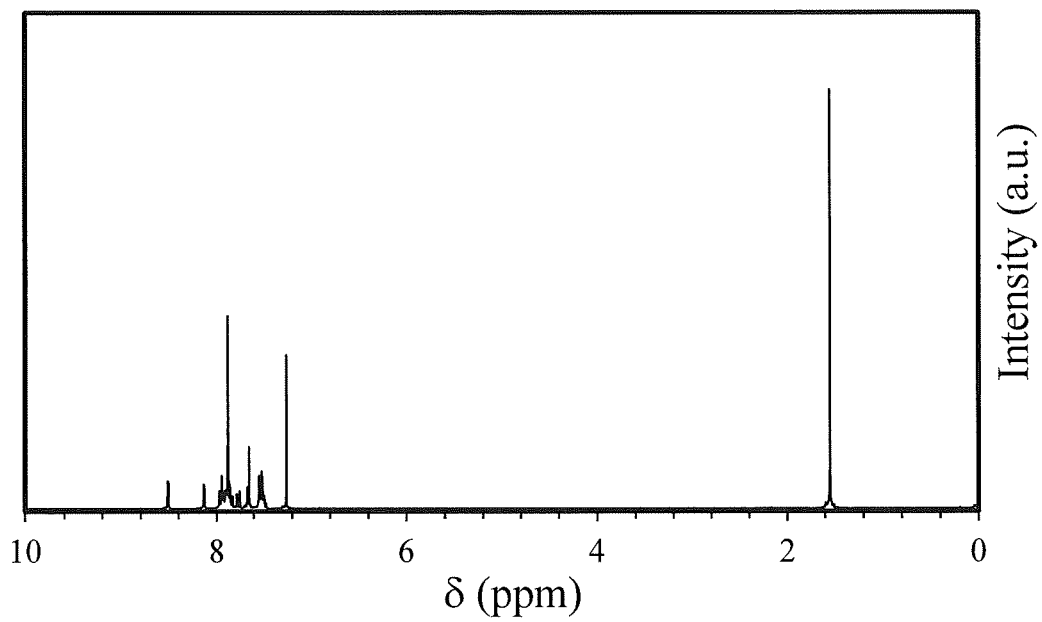
FIGS. 33A and 33B show $^1$H-NMR charts of βNP2PC.
Figure 33B:
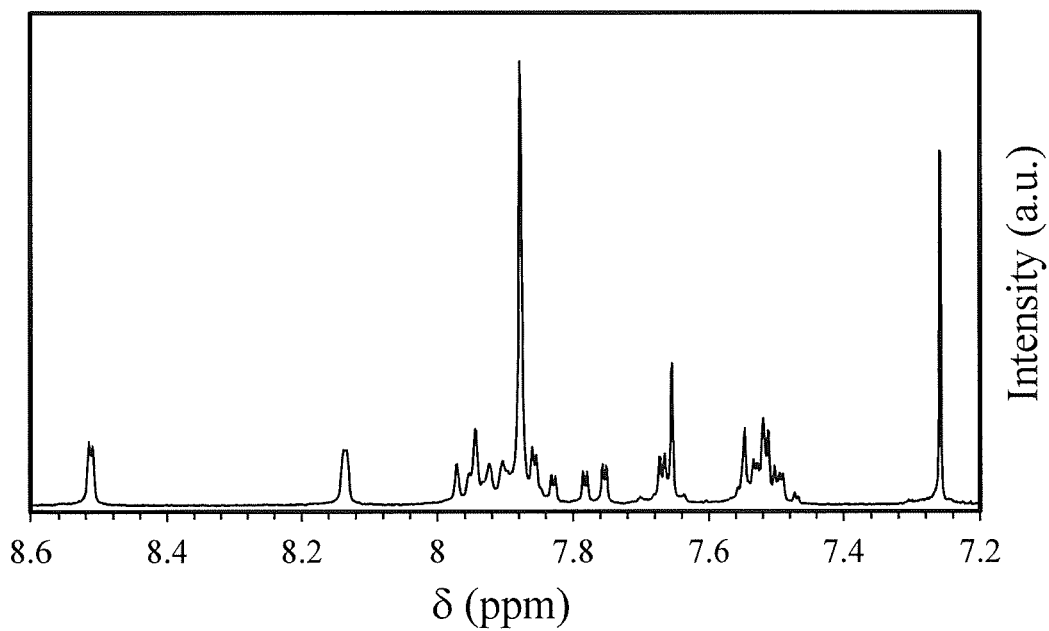

FIGS. 33A and 33B show the $^1$H-NMR charts. Note that FIG. 33B is an enlarged chart of a part in the range of 7.20 ppm to 8.60 ppm in FIG. 33A. The results indicate that βNP2PC was obtained by the synthesis reaction.

The thermogravimetry-differential thermal analysis (TG-DTA) of βNP2PC was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature of βNP2PC is higher than or equal to 500° C. The result showed that βNP2PC had favorable heat resistance.

REFERENCE EXAMPLE 3

In this reference example, a method for synthesizing 4-(1-naphthyl)-4',4"-diphenyltriphenylamine (abbreviation: BBAαNB), which was used in Light-emitting Element 2, is described. The structural formula of BBAαNB is shown below.

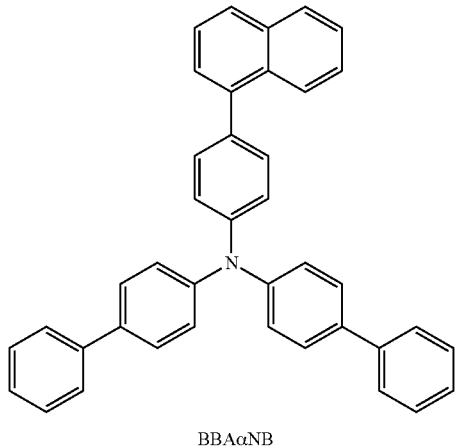 [SMILES: c1ccc(-c2ccc(N(c3ccc(-c4ccccc4)cc3)c3ccc(-c4cccc5ccccc45)cc3)cc2)cc1]

BBAαNB

Into a 200 mL three-neck flask were put 4.8 g (10 mmol) of 4-bromo-4',4"-diphenyltriphenylamine, 1.8 g (10 mmol) of 2-naphthylboronic acid, 0.31 g (1.0 mmol) of tris(2-methylphenyl)phosphine, 40 mL of toluene, 10 mL of ethanol, and 10 mL (2.0 mol/L) of a potassium carbonate solution. The mixture was degassed by being stirred while the pressure in the flask was reduced. After the degassing, the atmosphere in the flask was replaced with nitrogen, and this mixture was heated to 60° C. After the heating, 0.12 g (0.5 mmol) of palladium(II) acetate was added to this mixture, and the resulting mixture was stirred at 80° C. for 1.5 hours. After the stirring, the mixture was cooled down to room temperature, and an organic layer of the mixture was washed with water, the obtained aqueous layer was subjected to extraction with toluene. The extracted solution and the organic layer were combined, and the mixture was washed with saturated saline. Then, magnesium sulfate is added for drying. This mixture was gravity-filtered, and the obtained filtrate was concentrated to give a target brown solid. The obtained solid was dissolved in chloroform, and the resulting solution was purified by high performance liquid chromatography (recycling preparative HPLC using LC-SakuraNEXT manufactured by Japan Analytical Industry Co., Ltd., developing solvent: chloroform) to obtain 3.9 g of a target white solid at a yield of 75%. The synthesis scheme of this reaction is shown below.

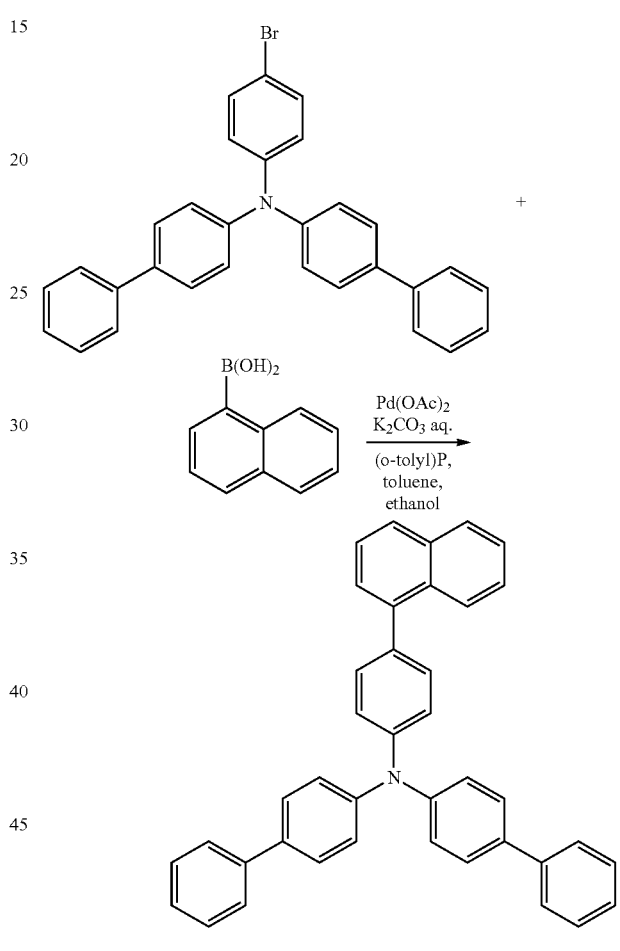

BBAαNB $^1$H NMR data of the obtained pale yellow solid were measured. The obtained data are shown below.

$^1$H NMR (dichloromethane-d$_2$, 500 MHz): δ=7.26-7.29 (m, 6H), 7.31 (t, J=7.0 Hz, 2H), 7.41-7.54 (m, 10H), 7.56 (d, J=8.5 Hz, 4H), 7.60 (d, J=7.0 Hz, 4H), 7.84 (d, J=8.0 Hz, 1H), 7.90 (d, J=7.0 Hz, 1H), 8.03 (d, J=9.0 Hz, 1H).

Figure 34A:
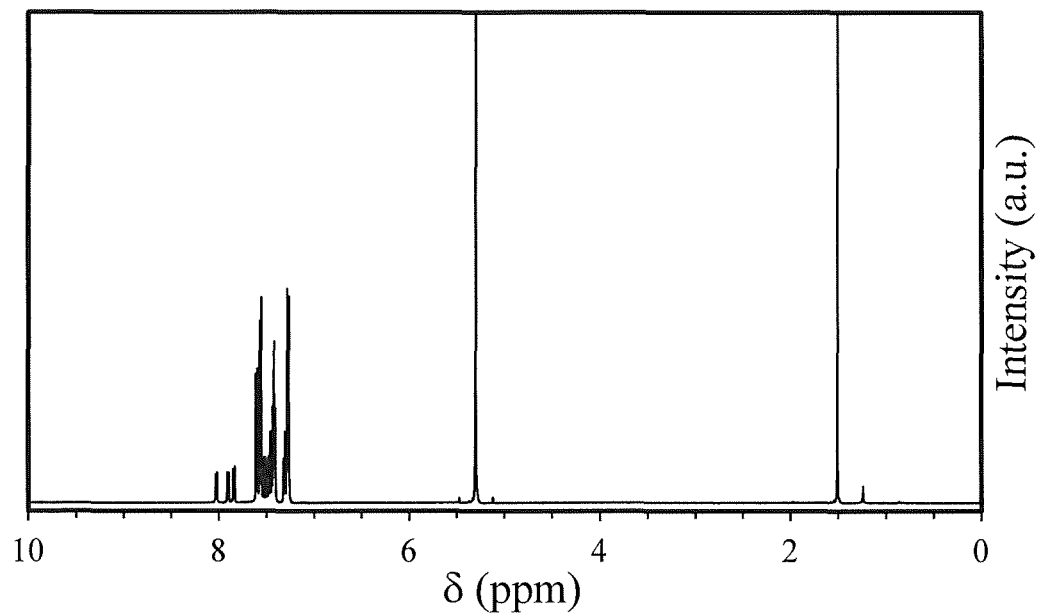
FIGS. 34A and 34B show $^1$H-NMR charts of BBAαNB.
Figure 34B:
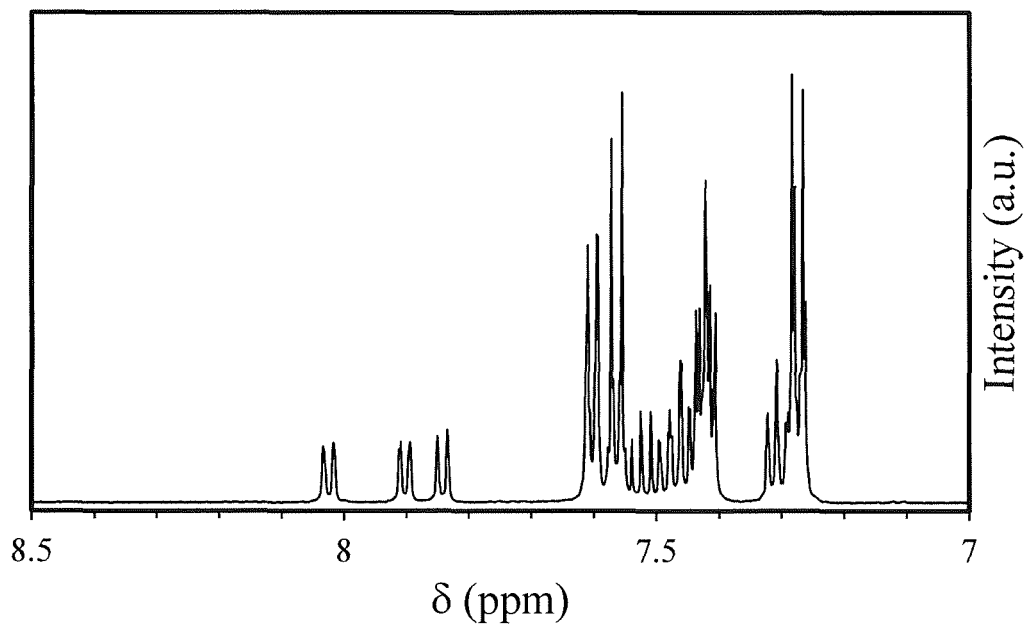

The $^1$H-NMR charts are shown in FIGS. 34A and 34B. Note that FIG. 34B is an enlarged chart of a part in the range of 7.0 ppm to 8.5 ppm in FIG. 34A. The results indicate that BBAαNB was obtained by the synthesis.

Then, 3.9 g of the obtained solid (BBAαNB) was purified by a train sublimation method. In the purification, the solid was heated at 250° C. under a pressure of 3.4 Pa for 16 hours with a flow rate of argon of 15 mL/min to give 2.4 g of a target solid at a correction rate of 62%.

The HOMO level and the LUMO level of BBAαNB were obtained through a cyclic voltammetry (CV) measurement. A calculation method is shown below.

An electrochemical analyzer (ALS model 600A or 600C, manufactured by BAS Inc.) was used as a measurement apparatus. As for a solution used in the CV measurement, dehydrated dimethylformamide (DMF) (manufactured by Aldrich, 99.8%, catalog number: 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was also dissolved in the solvent such that the concentration thereof was 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at room temperature (20° C. to 25° C.). In addition, the scan speed at the CV measurement was set to 0.1 V/sec, and an oxidation potential Ea [V] and a reduction potential Ec [V] with respect to the reference electrode were measured. Note that Ea represents an intermediate potential of an oxidation-reduction wave, and Ec represents an intermediate potential of a reduction-oxidation wave. Here, the potential energy of the reference electrode used in this example with respect to the vacuum level is found to be −4.94 [eV], and thus, the HOMO level and the LUMO level can be obtained from the following formula: HOMO level [eV]=−4.94−Ea and LUMO level [eV]=−4.94−Ec. Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of BBAαNB, the HOMO level was found to be −5.49 eV. Meanwhile, the LUMO level was found to be −2.24 eV. When the oxidation-reduction wave was repeatedly measured, in the Ea measurement, the peak intensity of the oxidation-reduction wave after the hundredth cycle was maintained to be 93% of that of the oxidation-reduction wave at the first cycle, and in the Ec measurement, the peak intensity of the oxidation-reduction wave after the hundredth cycle was maintained to be 92% of that of the oxidation-reduction wave at the first cycle; thus, resistance to oxidation and reduction of BBAαNB was found to be extremely high.

Differential scanning calorimetry (DSC measurement) of BBAαNB was performed by Pyris1DSC manufactured by PerkinElmer, Inc. In the differential scanning calorimetry, after the temperature was raised from −10° C. to 270° C. at a temperature rising rate of 40° C./min, the temperature was held for a minute and then cooled to −10° C. at a temperature decreasing rate of 40° C./min. This operation was repeated twice successively and the second measurement result was employed. The DSC measurement showed that the glass transition point of BBAαNB was 84° C.

REFERENCE EXAMPLE 4

In this reference example, a method for synthesizing 4-[4-(2-naphthyl)phenyl]-4',4''-diphenyltriphenylamine (abbreviation: BBAβNBi), which was used in Light-emitting Element 3, is described. The structural formula of BBAβNBi is shown below.

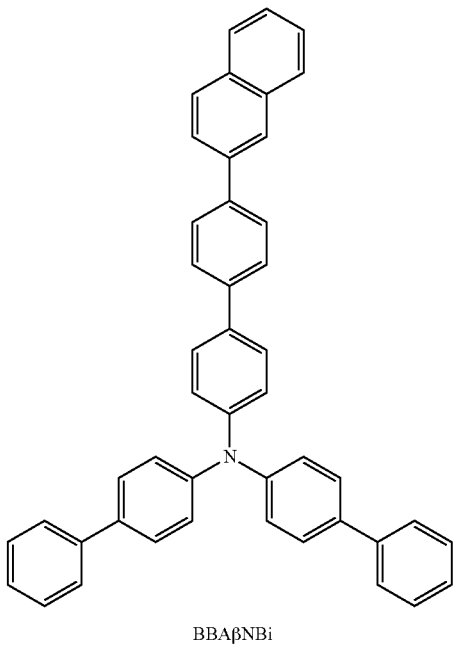 [SMILES: c1ccc(-c2ccc(N(c3ccc(-c4ccccc4)cc3)c3ccc(-c4ccc(-c5ccc6ccccc6c5)cc4)cc3)cc2)cc1]

BBAβNBi

Into a 200 mL three-neck flask were put 4.8 g (10 mmol) of 4-bromo-4',4''-diphenyltriphenylamine, 2.5 g (10 mmol) of 4-(2-naphthyl)phenylboronic acid, 0.31 g (0.50 mmol) of tris(2-methylphenyl)phosphine, 40 mL of toluene, 10 mL of ethanol, and 10 mL (2.0 mol/L) of a potassium carbonate solution. The mixture was degassed by being stirred while the pressure in the flask was reduced. After the degassing, the atmosphere in the flask was replaced with nitrogen, and this mixture was heated to 60° C. After the heating, 0.11 g (0.5 mmol) of palladium(II) acetate was added, and the resulting mixture was stirred at 80° C. for 1.5 hours. After the stirring, the mixture was cooled down to room temperature, and a precipitated solid was collected by suction filtration and washed with toluene, ethanol, and water. The obtained solid was washed with chloroform and collected by suction filtration, whereby 2.9 g of a target brown solid was obtained at a yield of 49%. A reaction scheme of this synthesis reaction is shown below.

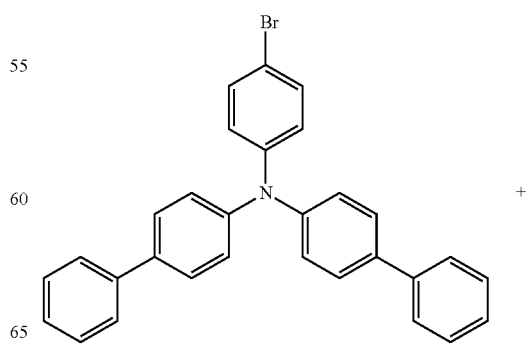

-continued

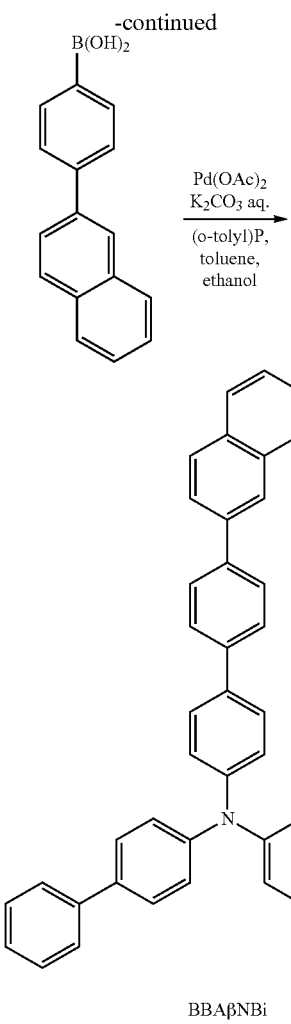

BBAβNBi $^1$H NMR data of the obtained pale yellow solid were measured. The obtained data are shown below.

$^1$H NMR (dichloromethane-$d_2$, 500 MHz, 500 MHz): δ=7.22-7.25 (m, 6H), 7.31 (t, J=7.3 Hz, 2H), 7.42 (t, J=7.8 Hz, 4H), 7.46-7.52 (m, 2H), 7.55 (d, J=7.5 Hz, 4H), 7.59-7.63 (m, 6H), 7.74 (d, J=8.0 Hz, 2H), 7.18-7.83 (m, 3H), 7.87 (d, J=7.5 Hz, 1H), 7.93 (t, J=8.7, 2H), 8.11 (s, 1H).

Figure 35A:
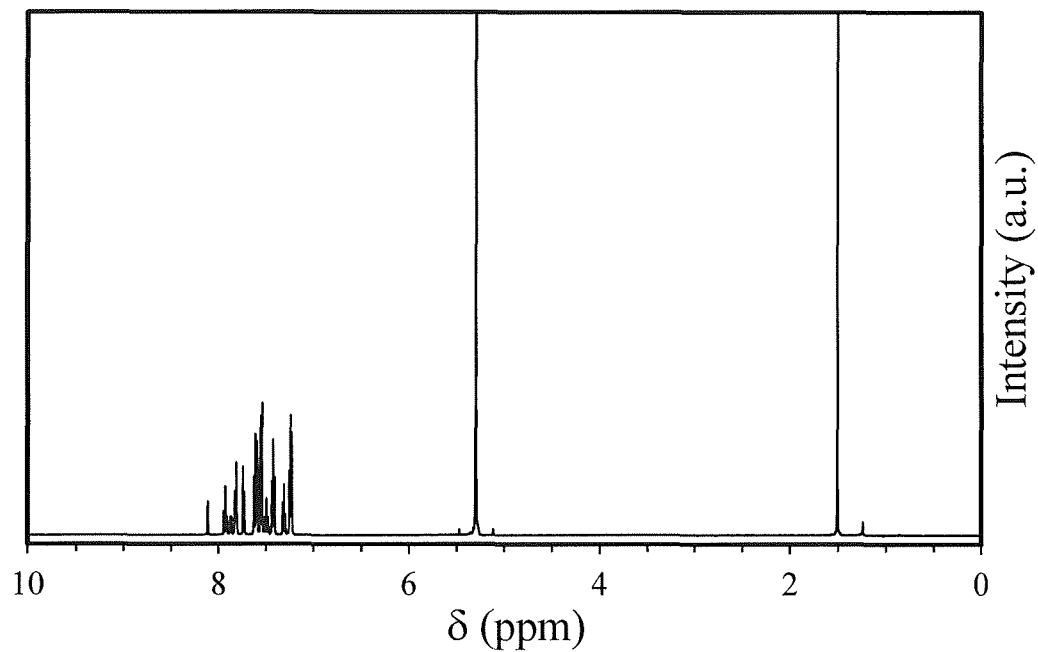
FIGS. 35A and 35B show $^1$H-NMR charts of BBAβNBi.
Figure 35B:
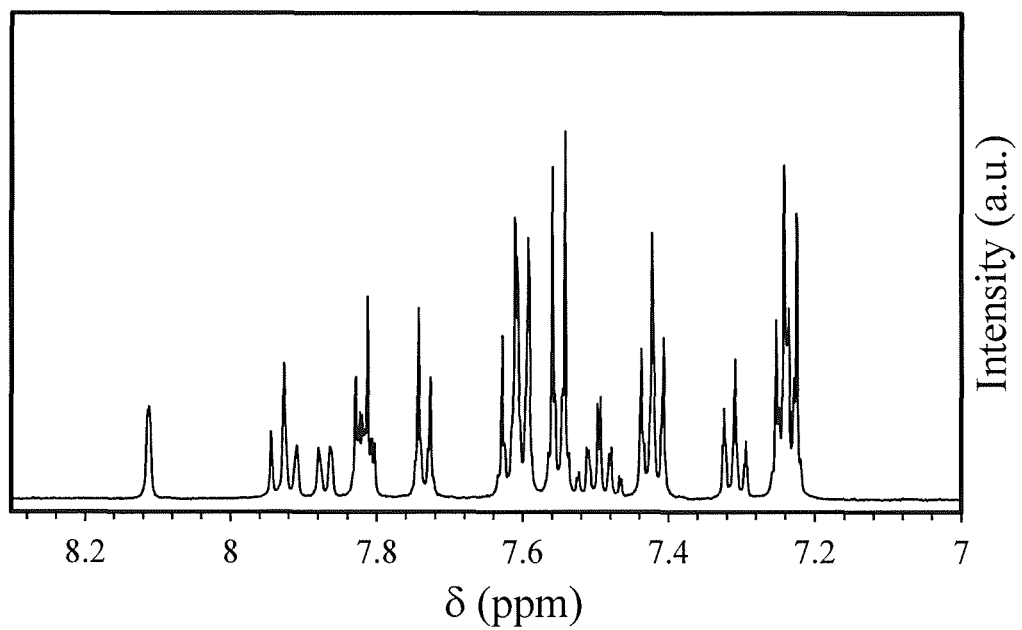

The $^1$H-NMR charts are shown in FIGS. 35A and 35B. Note that FIG. 35B is an enlarged chart of a part in the range of 7.0 ppm to 8.3 ppm in FIG. 35A. The results indicate that BBAβNBi was obtained by the synthesis reaction.

Then, 2.9 g of the obtained solid (BBAβNBi) was purified by a train sublimation method. In the purification, the solid was heated at 300° C. under a pressure of 4.0 Pa for 16 hours with a flow rate of argon of 15 mL/min to give 1.9 g of a target white solid at a correction rate of 65%.

The HOMO level and the LUMO level of BBAβNBi were obtained through a cyclic voltammetry (CV) measurement. A calculation method is similar to that in Reference Example 3.

As a result, in the measurement of an oxidation potential Ea [V] of BBAβNBi, the HOMO level was found to be −5.47 eV. Meanwhile, the LUMO level was found to be −2.38 eV. When the oxidation-reduction wave was repeatedly measured, in the Ea measurement, the peak intensity of the oxidation-reduction wave after the hundredth cycle was maintained to be 82% of that of the oxidation-reduction wave at the first cycle, and in the Ec measurement, the peak intensity of the oxidation-reduction wave after the hundredth cycle was maintained to be 67% of that of the oxidation-reduction wave at the first cycle; thus, resistance to oxidation and reduction of BBAβNBi was found to be extremely high.

Differential scanning calorimetry (DSC measurement) of BBAβNBi was performed by Pyris1DSC manufactured by PerkinElmer, Inc. In the differential scanning calorimetry, after the temperature was raised from −10° C. to 270° C. at a temperature rising rate of 40° C./min, the temperature was held for a minute and then cooled to −10° C. at a temperature decreasing rate of 40° C./min. This operation was repeated twice successively and the second measurement result was employed. The DSC measurement showed that the glass transition point of BBAβNBi was 97° C., which revealed that BBAβNBi is a compound with favorable heat resistance.

REFERENCE EXAMPLE 5

In this reference example, a method for synthesizing 3-[4-(2-naphthyl)phenyl]-9-(2-naphthyl)-9H-carbazole (abbreviation: βNPβNC), which was used in Light-emitting Element 4, is described. A structural formula of βNPβNC is shown below.

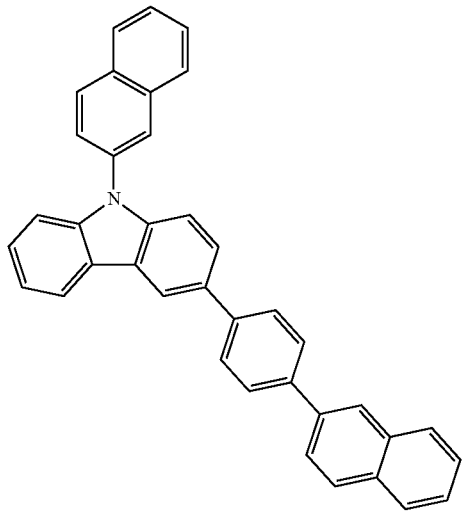

βNPβNC

Into a 200 mL three-neck flask were put 2.3 g (8.1 mmol) of 2-(4-bromophenyl)naphthalene, 3.4 g (8.1 mmol) of 4,4,5,5-tetramethyl-2-[9-(2-naphthyl)-9H-carbazol-3-yl]-1,3,2-dioxaborolane, 50 mg (0.16 mmol) of tri(o-tolyl)phosphine, and 2.2 g (16 mmol) of potassium carbonate. The air in the flask was replaced with nitrogen, and then 30 mL of toluene, 10 mL of ethanol, and 8.0 mL of water were added to the mixture. This mixture was degassed by being stirred while the pressure was reduced. After the degassing, 18 mg (0.081 mmol) of palladium(II) acetate was added to the mixture. This mixture was stirred at 80° C. for 4 hours under a nitrogen stream, so that a solid was precipitated. The precipitated solid was collected by suction filtration. The aqueous layer of the obtained filtrate was subjected to extraction with toluene, and the extracted solution and the organic layer were combined and washed with saturated brine. The organic layer was dried with magnesium sulfate, and this mixture was gravity-filtered. A solid obtained by concentrating the resulting filtrate and the collected solid were dissolved in approximately 200 mL of heated toluene. This solution was suction-filtered through Celite (Catalog No. 537-02305, produced by Wako Pure Chemical Industries, Ltd.), alumina, and Florisil (Catalog No. 066-05265, produced by Wako Pure Chemical Industries, Ltd.). The resulting filtrate was concentrated to give a solid. The solid was recrystallized with toluene to give 2.9 g of a target white powder in a yield of 72%. A reaction scheme of this synthesis reaction is shown below.

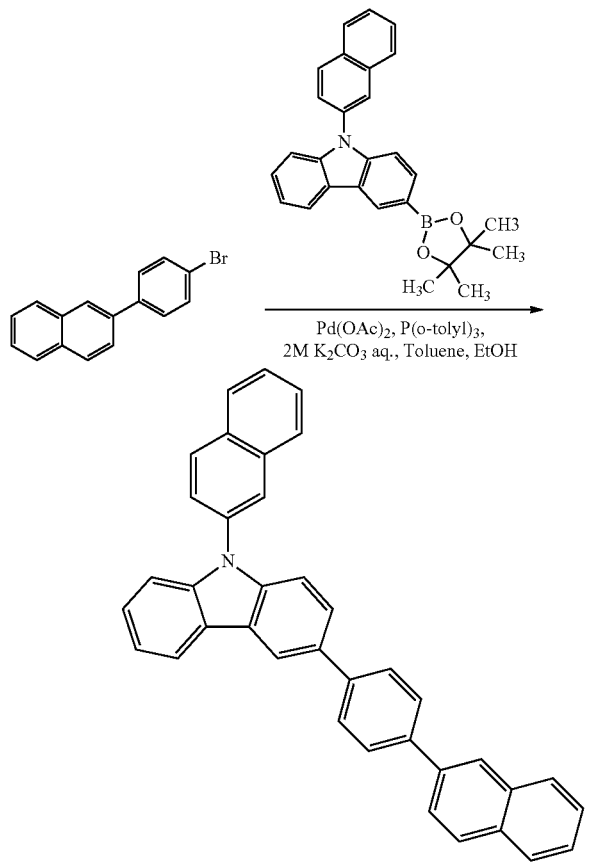

By a train sublimation method, 2.9 g of the obtained white powder was purified. In the purification, the white powder was heated at 280° C. under a pressure of 3.9 Pa with a flow rate of argon gas of 5.0 mL/min. After the purification by sublimation, 2.1 g of a white solid of βNPβNC was obtained at a collection rate of 72%.

The obtained substance was analyzed by $^1$H NMR. The measurement data are shown below.

$^1$H NMR (CDCl$_3$, 300 MHz): δ=7.35 (ddd, J$_1$=6.6 Hz, J$_2$=1.2 Hz, 1H), 7.42-7.63 (m, 5H), 7.60 (dd, J$_1$=9.6 Hz, J$_2$=6.3 Hz, 2H), 7.69-7.76 (m, 2H), 7.82-8.01 (m, 10H), 8.08-8.13 (m, 3H), 8.25 (d, J=7.8 Hz, 1H), 8.46 (d, J=1.5 Hz, 1H).

Figure 36A:
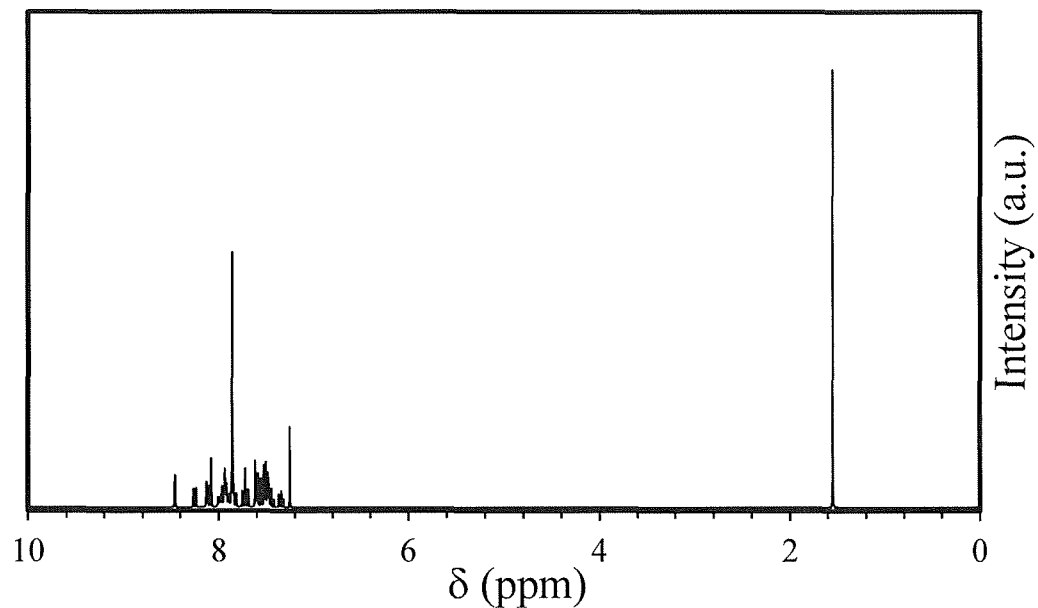
FIGS. 36A and 36B show $^1$H-NMR charts of βNPβNC.
Figure 36B:
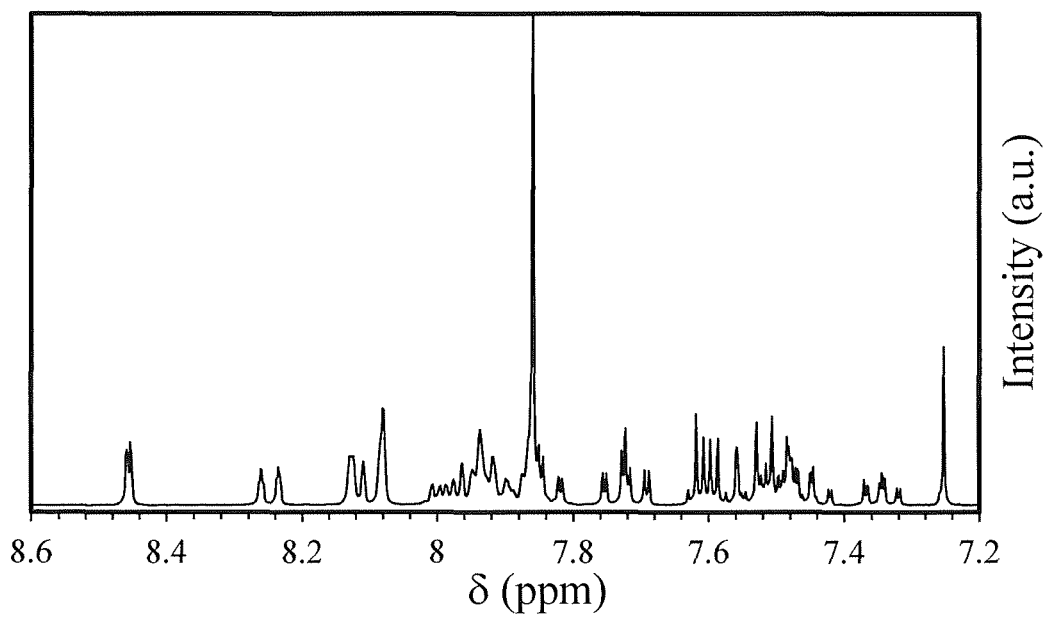

The $^1$H-NMR charts are shown in FIGS. 36A and 36B. Note that FIG. 36B is an enlarged chart of a part in the range of 7.20 ppm to 8.60 ppm in FIG. 36A. The results indicate that βNPβNC was obtained by the synthesis reaction.

The thermogravimetry-differential thermal analysis (TG-DTA) of βNPβNC was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature of βNPβNC is 431° C. The result showed that βNPβNC had favorable heat resistance.

This application is based on Japanese Patent Application Serial No. 2016-148511 filed with Japan Patent Office on Jul. 28, 2016, the entire contents of which are hereby incorporated by reference.

What is claimed is:
1. A light-emitting element comprising:
a first electrode;
an EL layer over the first electrode, the EL layer comprising:
a hole-injection layer being in contact with the first electrode;
a first hole-transport layer being in contact with the hole-injection layer;
a second hole-transport layer over the first hole-transport layer;
a third hole-transport layer;
a light-emitting layer being in contact with the third hole-transport layer;
a first electron-transport layer over and in contact with the light-emitting layer; and
a second electron-transport layer being in contact with the first electron-transport layer; and
a second electrode over the EL layer,
wherein the hole-injection layer, the first hole-transport layer, the second hole-transport layer and the third hole-transport layer are positioned between the first electrode and the light-emitting layer,
wherein the second hole-transport layer is positioned between the first hole-transport layer and the third hole-transport layer,
wherein the first electron-transport layer and the second electron-transport layer are positioned between the light-emitting layer and the second electrode,
wherein the hole-injection layer comprises an organic acceptor,
wherein the first hole-transport layer comprises a first hole-transport material,
wherein the second hole-transport layer comprises a second hole-transport material,
wherein the third hole-transport layer comprises a third hole-transport material,
wherein the light-emitting layer comprises a host material and a light-emitting material,
wherein the first electron-transport layer comprises a first electron-transport material,
wherein the second electron-transport layer comprises a second electron-transport material,
wherein a difference between a LUMO level of the organic acceptor and a HOMO level of the first hole-transport material is less than or equal to 1 eV,
wherein a HOMO level of the second hole-transport material is lower than the HOMO level of the first hole-transport material,
wherein a HOMO level of the host material is lower than the HOMO level of the second hole-transport material,
wherein a HOMO level of the third hole-transport material is lower than or equal to the HOMO level of the host material, wherein a difference between the HOMO level of the second hole-transport material and the HOMO level of the third hole-transport material is less than or equal to 0.3 eV, wherein a LUMO level of the host material is higher than a LUMO level of the first electron-transport material, wherein a LUMO level of the second electron-transport material is higher than the LUMO level of the first electron-transport material, wherein the host material is a substance including a condensed aromatic ring skeleton including 3 to 6 rings, wherein the first electron-transport material is a substance having a first heteroaromatic ring skeleton, wherein the second electron-transport material is a substance having a second heteroaromatic ring skeleton, and wherein the first heteroaromatic ring skeleton and the second heteroaromatic ring skeleton are different from each other.

2. The light-emitting element according to claim 1, wherein the light-emitting material is a fluorescent material.

3. The light-emitting element according to claim 1, wherein the light-emitting material is a condensed aromatic diamine compound.

4. The light-emitting element according to claim 1, wherein the organic acceptor is 2,3,6,7,10,11-hexacyano-1,4,5,8,9,12-hexaazatriphenylene.

5. The light-emitting element according to claim 1, wherein the host material has an anthracene skeleton.

6. The light-emitting element according to claim 1, wherein the substance including the first heteroaromatic ring skeleton is a substance including a condensed heteroaromatic ring skeleton.

7. The light-emitting element according to claim 1, wherein the substance including the first heteroaromatic ring skeleton is a substance including a pyrazine skeleton or a pyrimidine skeleton.

8. The light-emitting element according to claim 1, wherein the substance including the first heteroaromatic ring skeleton is a substance including a dibenzoquinoxaline skeleton.

9. A light-emitting device comprising:
the light-emitting element according to claim 1; and
a transistor or a substrate.

10. An electronic device comprising:
the light-emitting device according to claim 9; and
one selected from a sensor, an operation button, a speaker and a microphone.

11. A light-emitting element comprising:
a first electrode;
a hole-injection layer over the first electrode, the hole-injection layer comprising an organic acceptor;
a hole-transport layer over the hole-injection layer, the hole-transport layer comprising a hole-transport material;
a light-emitting layer over the hole-transport layer, the light-emitting layer comprising a host material and a light-emitting material;
a first electron-transport layer over the light-emitting layer, the first electron-transport layer comprising a first electron-transport material;
a second electron-transport layer over the first electron-transport layer, the second electron-transport layer comprising a second electron-transport material; and
a second electrode over the second electron-transport layer, wherein a difference between a LUMO level of the organic acceptor and a HOMO level of the hole-transport material is less than or equal to 1 eV, wherein a LUMO level of the host material is higher than a LUMO level of the first electron-transport material, wherein a LUMO level of the second electron-transport material is higher than the LUMO level of the first electron-transport material, wherein the host material has a condensed aromatic ring skeleton including 3 to 6 rings, wherein the first electron-transport material has a first heteroaromatic ring skeleton, wherein the second electron-transport material has a second heteroaromatic ring skeleton, and wherein the first heteroaromatic ring skeleton and the second heteroaromatic ring skeleton are different from each other.

12. The light-emitting element according to claim 11, wherein the light-emitting material is a fluorescent material.

13. The light-emitting element according to claim 11, wherein the light-emitting material is a condensed aromatic diamine compound.

14. The light-emitting element according to claim 11, wherein the organic acceptor is 2,3,6,7,10,11-hexacyano-1,4,5,8,9,12-hexaazatriphenylene.

15. The light-emitting element according to claim 11, wherein the host material has an anthracene skeleton.

16. The light-emitting element according to claim 11, wherein the first heteroaromatic ring skeleton is a condensed heteroaromatic ring skeleton.

17. The light-emitting element according to claim 11, wherein the first heteroaromatic ring skeleton is a pyrazine skeleton or a pyrimidine skeleton.

18. The light-emitting element according to claim 11, wherein the first heteroaromatic ring skeleton is a dibenzoquinoxaline skeleton.

19. The light-emitting element according to claim 11,
wherein the first heteroaromatic ring skeleton is a condensed heteroaromatic ring skeleton including a diazine skeleton or a triazine skeleton, and
wherein the second heteroaromatic ring skeleton comprises one of a pyridine skeleton and a bipyridine.

20. The light-emitting element according to claim 19, wherein the second heteroaromatic ring skeleton is a phenanthroline skeleton.

21. A light-emitting device comprising:
the light-emitting element according to claim 11; and
a transistor electrically connected to the light-emitting element.

22. An electronic device comprising:
the light-emitting device according to claim 21,
wherein the electronic device is any one of a television device, a monitor, a digital camera, a digital video camera, a digital photo frame, a mobile phone, a portable game console, a portable information terminal, an audio reproducing device, and a game machine.

* * * * *